US012733854B2

(12) United States Patent
Fukushima et al.

(10) Patent No.: US 12,733,854 B2
(45) Date of Patent: Sep. 15, 2026

(54) STRATIFICATION METHOD AND STRATIFICATION DEVICE

(71) Applicant: Medical Research and Development Corporation, Aichi (JP)

(72) Inventors: Masanori Fukushima, Aichi (JP); Bin Zhou, Aichi (JP); Zhen Hong, Shanghai (CN); Qianhua Zhao, Shanghai (CN)

(73) Assignee: Medical Research and Development Corporation, Aichi (JP)

( * ) Notice: Subject to any disclaimer, the term of this patent is extended or adjusted under 35 U.S.C. 154(b) by 159 days.

(21) Appl. No.: 18/689,257

(22) PCT Filed: Dec. 16, 2022

(86) PCT No.: PCT/JP2022/046352
§ 371 (c)(1),
(2) Date: Mar. 5, 2024

(87) PCT Pub. No.: WO2023/157447
PCT Pub. Date: Aug. 24, 2023

(65) Prior Publication Data

US 2024/0366132 A1 Nov. 7, 2024

(30) Foreign Application Priority Data

Feb. 18, 2022 (CN) ........................ 202210149360.2

(51) Int. Cl.
*A61B 5/00* (2006.01)
*A61B 5/16* (2006.01)
(Continued)

(52) U.S. Cl.
CPC ............ *A61B 5/165* (2013.01); *A61B 5/4088* (2013.01); *A61B 5/7264* (2013.01); *G16H 50/20* (2018.01); *G16H 50/30* (2018.01)

(58) Field of Classification Search
CPC ........ G16H 50/30; G16H 50/50; A61B 5/055; A61B 5/165; A61B 5/00; A61B 5/16;
(Continued)

(56) References Cited

U.S. PATENT DOCUMENTS

2013/0253367 A1 9/2013 Newman et al.
2019/0021674 A1 1/2019 Brewer, Jr. et al.
(Continued)

FOREIGN PATENT DOCUMENTS

CN 111247595 6/2020
JP 2020-509036 3/2020
(Continued)

OTHER PUBLICATIONS

Extended European Search Report issued Aug. 18, 2025 in corresponding European Patent Application No. 22926346.2.
(Continued)

*Primary Examiner* — Robert L Nasser
(74) *Attorney, Agent, or Firm* — Wenderoth, Lind & Ponack, L.L.P.

(57) ABSTRACT

A stratification method includes: obtaining, for each of a plurality of subjects with mild cognitive impairment, a score of a result of a clinical psychological test performed on the subject and a hippocampus volume of the subject; classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying.

26 Claims, 45 Drawing Sheets

| Factor | Category or unit | No. of cases | Event count | Multivariate (full model) | | | | Multivariate (STEPWISE) | | | |
|---|---|---|---|---|---|---|---|---|---|---|---|
| | | | | Hazard ratio | 95% CI | Wald test | | Hazard ratio | 95% CI | Wald test | |
| Age (years old) | 1 | 244 | 77 | 0.983 | (0.945, 1.023) | 0.4014 | | | | | |
| Smoking Status | Never | 198 | 63 | 1.000 | - | 0.0078 | * | 1.000 | - | 0.0108 | * |
| | Former | 33 | 10 | 1.462 | (0.698, 3.064) | | | 1.364 | (0.663, 2.806) | | |
| | Current | 13 | 4 | 6.248 | (1.933, 20.189) | | | 5.805 | (1.819,18.525) | | |
| Total education years / (years) | 1 | 244 | 77 | 1.125 | (1.014, 1.247) | 0.0266 | * | 1.086 | (0.989, 1.193) | 0.0835 | ** |
| Antidiabetic usages | No | 213 | 68 | 1.000 | - | 0.6844 | | | | | |
| | Yes | 31 | 9 | 1.185 | (0.523, 2.682) | | | | | | |
| Lipid lowering usages | No | 217 | 71 | 1.000 | - | 0.7064 | | | | | |
| | Yes | 27 | 6 | 0.837 | (0.331, 2.114) | | | | | | |
| MMSE : Total MMSE | 1 | 244 | 77 | 0.803 | (0.687, 0.938) | 0.0057 | * | 0.810 | (0.698, 0.940) | 0.0054 | * |
| CDR : Total score | 1 | 244 | 77 | 1.252 | (1.014, 1.547) | 0.0367 | * | 1.251 | (1.014, 1.544) | 0.0369 | * |
| ADAS-RC : Delayed Word-recall task | 1 | 244 | 77 | 0.965 | (0.539, 1.729) | 0.9050 | | | | | |
| ADAS-RC : Total ADAS-RC (11) | 1 | 244 | 77 | 0.926 | (0.536, 1.600) | 0.7839 | | | | | |
| ADAS-RC : Total ADAS-RC (13) | 1 | 244 | 77 | 1.139 | (0.662, 1.959) | 0.6387 | | 1.060 | (1.014, 1.107) | 0.0095 | * |
| Whole Brain Volume ($cm^3$) | 1 | 244 | 77 | 0.999 | (0.995, 1.003) | 0.5120 | | | | | |
| Hippocampus Volume Right ($cm^3$) | 1 | 244 | 77 | 0.710 | (0.353, 1.425) | 0.3353 | | 0.517 | (0.318, 0.841) | 0.0078 | * |
| Hippocampus Volume Left ($cm^3$) | 1 | 244 | 77 | 0.619 | (0.303, 1.263) | 0.1875 | ** | | | | |
| Temporal Lobe Volume Right ($cm^3$) | 1 | 244 | 77 | 0.952 | (0.849, 1.068) | 0.4012 | | | | | |
| Temporal Lobe Volume Left ($cm^3$) | 1 | 244 | 77 | 0.998 | (0.891, 1.119) | 0.9790 | | 0.941 | (0.892, 0.993) | 0.0265 | * |
| ApoE | 0 | 165 | 39 | 1.000 | - | < 0.0001 | * | 1.000 | - | < 0.0001 | * |
| | 1 ≤ | 79 | 38 | 2.670 | (1.632, 4.369) | | | 2.624 | (1.622, 4.248) | | |

*:$p < 0.05$ **:$p < 0.20$

(51) Int. Cl.
*G16H 50/20* (2018.01)
*G16H 50/30* (2018.01)

(58) Field of Classification Search
CPC ................ A61B 5/4088; A61B 5/7264; G06V 2201/03; G06F 18/24317; G06F 18/24
See application file for complete search history.

(56) References Cited

U.S. PATENT DOCUMENTS

| | | | |
|---|---|---|---|
| 2020/0258629 A1 | 8/2020 | Ahmad et al. |
| 2020/0271673 A1 | 8/2020 | Greenfield et al. |
| 2023/0024950 A1 | 1/2023 | Abushakra et al. |
| 2023/0260629 A1 | 8/2023 | Li et al. |

FOREIGN PATENT DOCUMENTS

| | | |
|---|---|---|
| JP | 2021-97988 | 7/2021 |
| WO | 2018/160868 | 9/2018 |
| WO | 2020/257159 | 12/2020 |
| WO | 2022/071158 | 4/2022 |

OTHER PUBLICATIONS

M. Lehtovirta, et al. "Volumes of Hippocampus, Amygdala and Frontal Lobe in Alzheimer Patients With Different Apolipoprotein E Genotypes", Neuroscience, Jul. 1995, vol. 67, No. 1, pp. 65-72.
International Search Report (ISR) issued on Jan. 31, 2023 in International (PCT) Application No. PCT/JP2022/046352.
Bin Zhou et al., "Protective Factors Modulate the Risk of Beta Amyloid in Alzheimer's Disease," Behavioral Neurology, Oct. 2020, vol. 2020, Article ID 7029642, pp. 1-8.
Shi Feng, et al., "Hippocampal Volume and Asymmetry in Mild Cognitive Impairment and Alzheimer's Disease: Meta-Analyses of MRI Studies," Hippocampus, Mar. 2009, vol. 19, Issue 11, pp. 1055-1064.
Zhang Wen, et al., "Morphometric Analysis of Hippocampus and Lateral Ventricle Reveals Regional Difference between Cognitively Stable and Declining Persons," Proceedings IEEE International Symposium on Biomedical Imaging, Aug. 2016, pp. 14-18.

FIG. 1

| Factor | Category or unit | No. of cases | Event count | Multivariate (full model) | | | | Multivariate (STEPWISE) | | | |
|---|---|---|---|---|---|---|---|---|---|---|---|
| | | | | Hazard ratio | 95% CI | Wald test | | Hazard ratio | 95% CI | Wald test | |
| Age (years old) | 1 | 244 | 77 | 0.983 | (0.945, 1.023) | 0.4014 | | | | | |
| Smoking Status | Never | 198 | 63 | 1.000 | - | 0.0078 | * | 1.000 | - | 0.0108 | * |
| | Former | 33 | 10 | 1.462 | (0.698, 3.064) | | | 1.364 | (0.663, 2.806) | | |
| | Current | 13 | 4 | 6.248 | (1.933, 20.189) | | | 5.805 | (1.819,18.525) | | |
| Total education years / (years) | 1 | 244 | 77 | 1.125 | (1.014, 1.247) | 0.0266 | * | 1.086 | (0.989, 1.193) | 0.0835 | ** |
| Antidiabetic usages | No | 213 | 68 | 1.000 | - | 0.6844 | | | | | |
| | Yes | 31 | 9 | 1.185 | (0.523, 2.682) | | | | | | |
| Lipid lowering usages | No | 217 | 71 | 1.000 | - | 0.7064 | | | | | |
| | Yes | 27 | 6 | 0.837 | (0.331, 2.114) | | | | | | |
| MMSE : Total MMSE | 1 | 244 | 77 | 0.803 | (0.687, 0.938) | 0.0057 | * | 0.810 | (0.698, 0.940) | 0.0054 | * |
| CDR : Total score | 1 | 244 | 77 | 1.252 | (1.014, 1.547) | 0.0367 | * | 1.251 | (1.014, 1.544) | 0.0369 | * |
| ADAS-RC : Delayed Word-recall task | 1 | 244 | 77 | 0.965 | (0.539, 1.729) | 0.9050 | | | | | |
| ADAS-RC : Total ADAS-RC (11) | 1 | 244 | 77 | 0.926 | (0.536, 1.600) | 0.7839 | | | | | |
| ADAS-RC : Total ADAS-RC (13) | 1 | 244 | 77 | 1.139 | (0.662, 1.959) | 0.6387 | | 1.060 | (1.014, 1.107) | 0.0095 | * |
| Whole Brain Volume ($cm^3$) | 1 | 244 | 77 | 0.999 | (0.995, 1.003) | 0.5120 | | | | | |
| Hippocampus Volume Right ($cm^3$) | 1 | 244 | 77 | 0.710 | (0.353, 1.425) | 0.3353 | | 0.517 | (0.318, 0.841) | 0.0078 | * |
| Hippocampus Volume Left ($cm^3$) | 1 | 244 | 77 | 0.619 | (0.303, 1.263) | 0.1875 | ** | | | | |
| Temporal Lobe Volume Right ($cm^3$) | 1 | 244 | 77 | 0.952 | (0.849, 1.068) | 0.4012 | | | | | |
| Temporal Lobe Volume Left ($cm^3$) | 1 | 244 | 77 | 0.998 | (0.891, 1.119) | 0.9790 | | 0.941 | (0.892, 0.993) | 0.0265 | * |
| ApoE | 0 | 165 | 39 | 1.000 | - | < 0.0001 | * | 1.000 | - | < 0.0001 | * |
| | 1 < = | 79 | 38 | 2.670 | (1.632, 4.369) | | | 2.624 | (1.622, 4.248) | | |

*: $p < 0.05$ **: $p < 0.20$

| Analysis Value (year) | Cumulative conversion rate | 95% CI | At Risk | Cumulative event count |
|---|---|---|---|---|
| 0 | 0 | (0.0, 0.0) | 325 | 0 |
| 0.5 | 0 | (0.0, 0.0) | 325 | 0 |
| 1 | 5.5 | (3.4, 8.6) | 288 | 17 |
| 1.5 | 13.8 | (10.4, 18.2) | 245 | 42 |
| 2 | 15.6 | (12.0, 20.2) | 232 | 47 |
| 2.5 | 22.5 | (18.1, 27.8) | 191 | 65 |
| 3 | 29.6 | (24.5, 35.5) | 157 | 82 |
| 3.5 | 35.4 | (29.6, 41.9) | 79 | 92 |
| 4 | 47.1 | (38.5, 56.5) | 14 | 101 |
| 4.5 | 69.1 | (47.9, 87.9) | 3 | 104 |
| 5 | 69.1 | (47.9, 87.9) | 1 | 104 |

FIG. 17

| | Total | Conversion to AD | Stable MCI |
|---|---|---|---|
| Number of cases | 220 | 70 | 150 |
| Age (y) (SD) | 72.9 (6.5) | 73.6 (6.4) | 72.6 (6.5) |
| Education (y) (SD) | 16.06 (2.83) | 16.2 (2.59) | 16.0 (2.95) |
| Gender (male) (%) | 116 | 42 (60.87) | 74 (52.11) |
| Apoe4_non_carrier (%) | 64 | 12 (17.4) | 52 (36.7) |
| MMSE (SD) | 27.65 (1.81) | 27.02 (1.75) | 27.91 (1.8) |
| ADAS-RC:Total ADAS-RC (13) (SD) | 16.86 (6.89) | 22.1 (6.9) | 14.5 (5.4) |
| PET amyloid AV45 (SD) | 1.38 (0.17) | 1.46 (0.17) | 1.35 (0.16) |
| Left hippocampus volume ($mm^3$) (SD) | 3387.47 (540.4) | 3105.8 (426.8) | 3514.7 (539.3) |
| Average follow-up time (y) (SD) | 2.27 (1.13) | 1.71 (1.04) | 2.53 (1.049) |

PET amyloid AV45 > 1.11

| Group | | Hippocampus Volume Left ($mm^3$) | |
|---|---|---|---|
| | | < 3459 | 3459 < = |
| Total ADAS-RC (13) | < 14.0 | C | A |
| | 14.0 < = | B | D |

The number of conversion and non-conversion in MCIs with elevated PET beta amyloid

| Stratify | group | Tot. | conversion | non-conversion | non-conversion rate (%) |
|---|---|---|---|---|---|
| 1 | A | 101 | 51 | 50 | 49.5 |
| 2 | B | 41 | 0 | 41 | 100.00 |
| 3 | C | 30 | 7 | 23 | 76.67 |
| 4 | D | 48 | 12 | 36 | 75.00 |
| Total | | 220 | 70 | 150 | 68.18 |

| Group | | Hippocampus Volume Left ($mm^3$) | |
|---|---|---|---|
| | | < 3737 | 3737 < = |
| Total ADAS-RC (13) | < 12.0 | C | A |
| | 12.0 < = | B | D |

| The number of conversion and non-conversion in MCIs with elevated PET beta amyloid | | | | | |
|---|---|---|---|---|---|
| Stratify | group | Tot. | conversion | non-conversion | non-conversion rate (%) |
| 1 | A | 136 | 62 | 74 | 54.41 |
| 2 | B | 22 | 0 | 22 | 100.00 |
| 3 | C | 28 | 3 | 25 | 89.29 |
| 4 | D | 34 | 5 | 29 | 85.29 |
| Total | | 220 | 70 | 150 | 68.18 |

Kaplan-Meier curve for first diagnosed with AD

| Group | | Hippocampus Volume Left ($mm^3$) | |
|---|---|---|---|
| | | < 3080 | 3080 < = |
| Total ADAS-RC (13) | < 21.0 | C | A |
| | 21.0 < = | B | D |

The number of conversion and non-conversion in MCIs with elevated PET beta amyloid

| Stratify | group | Tot. | conversion | non-conversion | non-conversion rate (%) |
|---|---|---|---|---|---|
| 1 | A | 24 | 19 | 5 | 20.83 |
| 2 | B | 132 | 23 | 109 | 82.58 |
| 3 | C | 30 | 12 | 18 | 60.00 |
| 4 | D | 34 | 16 | 18 | 52.94 |
| Total | | 220 | 70 | 150 | 68.18 |

| Group | | Hippocampus Volume Left ($mm^3$) | |
|---|---|---|---|
| | | < 2751 | 2751 < = |
| Total ADAS-RC (13) | < 24.0 | C | A |
| | 24.0 < = | B | D |

The number of conversion and non-conversion in MCIs with elevated PET beta amyloid

| Stratify | group | Tot. | conversion | non-conversion | non-conversion rate (%) |
|---|---|---|---|---|---|
| 1 | A | 11 | 10 | 1 | 9.09 |
| 2 | B | 168 | 36 | 132 | 78.57 |
| 3 | C | 13 | 4 | 9 | 69.23 |
| 4 | D | 28 | 20 | 8 | 28.57 |
| Total | | 220 | 70 | 150 | 68.18 |

Kaplan-Meier curve for first diagnosed with AD

FIG. 31

| Group | MCI with elevated beta amyloid | | All MCI | |
|---|---|---|---|---|
| | Conversion to AD | Stable MCI | Conversion to AD | Stable MCI |
| Cog_Vol < 101 | 16 (94.12%) | 1 (5.88%)* | 17 (77.27%) | 5 (22.23%) |
| 101 < = Cog_Vol < = 250 | 48 (39.02%) | 75 (60.98%) | 53 (29.94%) | 124 (70.06%) |
| Cog_Vol > 250 | 6 (7.06%) | 79 (92.94%) | 8 (3.86%) | 199 (96.14%) |
| Total | 70 | 155 | 78 | 328 |

*The subject was followed-up for 1 year.

FIG. 33

| Group | MCI with elevated beta amyloid (N = 220) | | |
|---|---|---|---|
| | Conversion to AD | Stable MCI | Conversion rate (%) |
| Cog_Vol < 101 | 16 | 1 | 94.1 |
| 101 < = Cog_Vol < = 142 | 18 | 12 | 60.0 |
| 142 < Cog_Vol < = 266 | 33 | 68 | 32.6 |
| 266 < Cog_Vol < = 340 | 3 | 27 | 10.4 |
| Cog_Vol > 340 | 0 | 42 | 0 |
| Total | 70 | 150 | |

FIG. 35

Cog_Vol and subjects with elevated beta amyloid

| Cog_Vol | Year | Conversion to AD | Stable MCI | Conversion rate (%) |
|---|---|---|---|---|
| < 101 | 1 | 12 | 0 | 70.5 |
| | 2 | 3 | 1 | 88.2 |
| | 3 | 1 | 0 | 94.1 |
| | Total | 16 | 1 | 94.1 |
| 101 ~ 142 | 1 | 3 | 3 | 10.0 |
| | 2 | 5 | 5 | 26.6 |
| | 3 | 10 | 3 | 60.0 |
| | 4 | 0 | 1 | 60.0 |
| | Total | 18 | 12 | 60.0 |
| 142 ~ 266 | 1 | 6 | 12 | 5.9 |
| | 2 | 8 | 18 | 13.9 |
| | 3 | 15 | 17 | 28.7 |
| | 4 | 4 | 21 | 32.7 |
| | Total | 33 | 68 | 32.7 |
| = > 266 | 1 | 1 | 2 | 1.4 |
| | 2 | 0 | 11 | 1.4 |
| | 3 | 0 | 22 | 1.4 |
| | 4 | 2 | 34 | 4.16 |
| | Total | 3 | 69 | 4.16 |

FIG. 36

| Group | MCI (N = 843) | | |
|---|---|---|---|
| | Conversion to AD | Stable MCI | Conversion rate (%) |
| Cog_Vol < 101 | 50 | 14 | 78.1 |
| 101 < = Cog_Vol < = 142 | 82 | 54 | 60.3 |
| 142 < Cog_Vol < = 266 | 125 | 235 | 34.6 |
| 266 < Cog_Vol < = 340 | 10 | 87 | 10.3 |
| Cog_Vol > 340 | 6 | 180 | 3.2 |
| Total | 273 | 570 | |

FIG. 38

Conversion rate by Cog_Vol in all MIC subjects covering positive, negative, and unknown beta amyloid information

| Cog_Vol_ab | Year | Conversion to AD | Stable MCI | Conversion rate (%) |
|---|---|---|---|---|
| < 101 | 1 | 22 | 3 | 34.9 |
| | 2 | 13 | 3 | 55.5 |
| | 3 | 3 | 5 | 60.3 |
| | 4 | 2 | 1 | 63.5 |
| | 5 | 3 | 0 | 68.3 |
| | 6 | 7 | 1 | 79.4 |
| | Total | 50 | 13 | 79.4 |
| 102 – 142 | 1 | 20 | 11 | 15.0 |
| | 2 | 20 | 12 | 30.1 |
| | 3 | 21 | 11 | 45.9 |
| | 4 | 10 | 9 | 53.4 |
| | 5 | 2 | 2 | 54.9 |
| | 6 | 9 | 6 | 61.6 |
| | Total | 82 | 51 | 61.6 |
| 142 – 266 | 1 | 22 | 26 | 6.4 |
| | 2 | 33 | 32 | 16.0 |
| | 3 | 32 | 51 | 25.4 |
| | 4 | 13 | 50 | 29.2 |
| | 5 | 8 | 16 | 31.5 |
| | 6 | 17 | 43 | 36.4 |
| | Total | 125 | 218 | 36.4 |
| 266 – 340 | 1 | 3 | 4 | 3.2 |
| | 2 | 2 | 10 | 5.4 |
| | 3 | 1 | 26 | 6.5 |
| | 4 | 1 | 21 | 7.6 |
| | 5 | 1 | 8 | 8.7 |
| | 6 | 2 | 13 | 10.8 |
| | Total | 10 | 82 | 10.8 |
| = > 340 | 1 | 0 | 4 | 0 |
| | 2 | 0 | 13 | 0 |
| | 3 | 1 | 51 | 0.6 |
| | 4 | 0 | 54 | 0.6 |
| | 5 | 2 | 25 | 1.7 |
| | 6 | 3 | 22 | 3.4 |
| | Total | 6 | 169 | 3.4 |

FIG. 39

Cog_Vol_ab in subjects who have beta amyloid data (including positive and negative)

| Cog_Vol_ab | Year | Conversion to AD | Stable MCI | Conversion rate (%) |
|---|---|---|---|---|
| < 67 | 1 | 11 | 1 | 64.7 |
| | 2 | 3 | 0 | 82.4 |
| | 3 | 1 | 0 | 88.2 |
| | 6 | 1 | 0 | 94.1 |
| | Total | 16 | 1 | 94.1 |
| 68 − 135 | 1 | 10 | 8 | 11.1 |
| | 2 | 2 | 11 | 13.3 |
| | 3 | 19 | 16 | 34.4 |
| | 4 | 4 | 7 | 38.8 |
| | 5 | 0 | 5 | 38.8 |
| | 6 | 4 | 4 | 43.3 |
| | Total | 39 | 51 | 43.3 |
| 136 − 177 | 1 | 4 | 7 | 7.4 |
| | 2 | 3 | 10 | 13.0 |
| | 3 | 6 | 10 | 24.0 |
| | 4 | 1 | 10 | 25.9 |
| | 5 | 0 | 10 | 25.9 |
| | 6 | 1 | 2 | 27.8 |
| | Total | 15 | 39 | 27.8 |
| 178 − 392 | 1 | 2 | 4 | 1.3 |
| | 2 | 2 | 22 | 2.5 |
| | 3 | 1 | 58 | 3.2 |
| | 4 | 2 | 61 | 3.2 |
| | 5 | 1 | 22 | 3.8 |
| | 6 | 2 | 5 | 5.1 |
| | Total | 8 | 150 | 5.1 |
| = > 393 | 1 | 0 | 3 | 0 |
| | 2 | 0 | 2 | 0 |
| | 3 | 0 | 20 | 0 |
| | 4 | 0 | 29 | 0 |
| | 5 | 0 | 13 | 0 |
| | 6 | 0 | 5 | 0 |
| | Total | 0 | 72 | 0 |

STRATIFICATION METHOD AND STRATIFICATION DEVICE

TECHNICAL FIELD

The present invention relates to a stratification method for accurately stratifying a plurality of subjects with mild cognitive impairment (MCI) according to their degree of risk of progressing to Alzheimer's disease in the future.

BACKGROUND ART

Some groups of individuals with mild cognitive impairment will progress to Alzheimer's disease in the future, while others will not.

If prevention trials, etc., can be conducted on individuals with a relatively high risk of progressing to Alzheimer's disease in the future among the groups of individuals with mild cognitive impairment, such prevention trials, etc., can be conducted effectively.

Conventionally, the technique described in Non Patent Literature (NPL) 1, for example, is known as a technique for classifying each of a plurality of subjects suffering from mild cognitive impairment into one of a plurality of groups according to the risk of progressing to Alzheimer's disease in the future.

CITATION LIST

Non Patent Literature

[NPL 1] Bin Zhou et. al, Protective Factors Modulate the Risk of Beta Amyloid in Alzheimer's Disease, Behavioral Neurology, Volume 2020, Article ID 7029642

SUMMARY OF INVENTION

Technical Problem

The conventional technique described in NPL 1 uses the results of beta-amyloid brain PET scans to make the above classification.

This beta-amyloid brain PET scan is a relatively expensive test. It is therefore difficult to widely disseminate the above classification using the conventional techniques described in NPL 1 to the general public. In addition, only about 41% of those with abnormal beta-amyloid brain PET scans progress to Alzheimer's disease at an average follow-up study of 26 months.

Therefore, the present invention was made in view of the above problem, and has an object to provide a stratification method, etc., in which each group of individuals suffering from mild cognitive impairment is classified into an appropriate group according to the degree of risk of progressing to Alzheimer's disease in the future, in a manner different from conventional techniques that use beta-amyloid brain PET scan results.

Solution to Problem

A stratification method according to one aspect of the present invention includes: obtaining, for each of a plurality of subjects with mild cognitive impairment, a score of a clinical psychological test performed on the subject and a hippocampus volume of the subject; classifying each of the plurality of subjects into one of a plurality of groups based on the Alzheimer's disease assessment scale-cognitive subscale score of the subject and the hippocampus volume of the subject, the plurality of groups including at least a first group at a relatively high risk of future progression to Alzheimer's disease and a second group at a relatively low risk of future progression to Alzheimer's disease; and outputting a stratification result of the stratifying.

A stratification device according to one aspect of the present invention includes: an obtainment unit configured to obtain, for each of a plurality of subjects with mild cognitive impairment, a result of a clinical psychological test performed on the individual, and a hippocampus volume; a classification unit configured to classify each of the plurality of subjects into one of a plurality of groups based on the score of the subject and the hippocampus volume of the subject, the plurality of groups including at least a high-risk group at a relatively high risk of future progression to Alzheimer's disease and a low-risk group at a relatively low risk of future progression to Alzheimer's disease; and an output unit configured to output a classification result obtained via the above steps.

Advantageous Effects of Invention

With the stratification method, etc., according to one aspect of the present invention, each of a plurality of subjects with mild cognitive impairment can be classified into one of a plurality of groups according to the risk of progressing to Alzheimer's disease in the future, in a manner different from conventional techniques.

BRIEF DESCRIPTION OF DRAWINGS

FIG. 1 is a schematic diagram illustrating one example of the content of a risk assessment conducted by the inventors for various factors.

FIG. 17 is a schematic diagram illustrating one example of the content of a risk assessment conducted by the inventors for various factors, further performed for individuals with a positive beta-amyloid brain PET scan.

FIG. 31 is a correspondence table showing the relationship between volume score values (Cog_Vol) and the number of subjects who progressed from mild cognitive impairment to Alzheimer's disease.

FIG. 33 is a correspondence table showing the relationship between volume score values (Cog_Vol), a plurality of thresholds, and the number of subjects who progressed from mild cognitive impairment to Alzheimer's disease.

FIG. 35 is a correspondence table showing the relationship between volume score values (Cog_Vol), a plurality of thresholds, and a change in the ratio of subjects who progressed from mild cognitive impairment to Alzheimer's disease.

FIG. 36 is a correspondence table showing the relationship between volume score values (Cog_Vol), a plurality of thresholds, and the number of subjects who progressed from mild cognitive impairment to Alzheimer's disease.

FIG. 38 is a correspondence table showing the relationship between volume score values (Cog_Vol), a plurality of thresholds, and a change in the ratio of subjects who progressed from mild cognitive impairment to Alzheimer's disease.

FIG. 39 is a correspondence table showing the relationship between volume score values (Cog_Vol_ab), a plurality of thresholds, and a change in the ratio of subjects who progressed from mild cognitive impairment to Alzheimer's disease.

Figure 2:
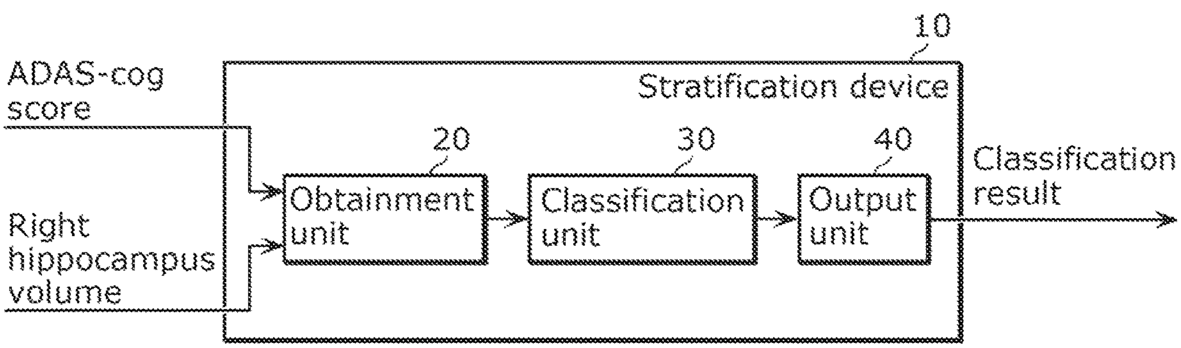
FIG. 2 is a block diagram illustrating one example of the configuration of the stratification method according to Embodiment 1.

DESCRIPTION OF EMBODIMENTS (Circumstances Leading to an Aspect of the Present Invention)

In order to find a stratification method that would classify, with relative accuracy, each of a plurality of subjects with mild cognitive impairment into one of a plurality of groups according to their risk of progressing to Alzheimer's disease in the future, the inventors assessed the risk of progressing from mild cognitive impairment to Alzheimer's disease for various factors.

FIG. 1 is a schematic diagram illustrating one example of the content of a risk assessment conducted by the inventors for various factors.

In the process of conducting a risk assessment for various factors, the inventors found that the risk of progressing from mild cognitive impairment to Alzheimer's disease can be assessed with relatively high accuracy by using an index that combines the result obtained from a clinical psychological test of the subject and the hippocampus volume of the subject.

The inventors investigated further based on this finding and devised the following stratification method and the like.

A stratification method according to one aspect of the present invention includes: obtaining, for each of a plurality of subjects with mild cognitive impairment, a score of a result of a clinical psychological test performed on the subject and a hippocampus volume of the subject; classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying.

With the above stratification method, each of a plurality of subjects with mild cognitive impairment can be classified into one of a plurality of groups according to the risk of progressing to Alzheimer's disease in the future, in a manner different from conventional techniques that use beta-amyloid brain PET scan results.

The hippocampus volume of each of the plurality of subjects may be a right hippocampus volume of each of the plurality of subjects.

The clinical psychological test may be an Alzheimer's disease assessment scale-cognitive subscale test.

In the classifying, for each of the plurality of subjects, the subject may be classified into the first group if the score of the subject is greater than a first threshold and the right hippocampus volume of the subject is less than a second threshold, and classified into the second group if the score of the subject is less than the first threshold and the right hippocampus volume of the subject is greater than the second threshold.

The first threshold may be 20.0, and the second threshold may be 3.651 [$cm^3$].

The clinical psychological test may be a preclinical Alzheimer's cognitive composite test.

In the classifying, for each of the plurality of subjects, the subject may be classified into the first group if the score of the subject is less than a third threshold and the right hippocampus volume of the subject is less than a fourth threshold, and classified into the second group if the score of the subject is greater than the third threshold and the right hippocampus volume of the subject is greater than the fourth threshold.

The third threshold may be 0.111, and the fourth threshold may be 3.651 [$cm^3$].

The obtaining may include further obtaining, for each of the plurality of subjects, information indicating whether the subject is an apolipoprotein Eε4 gene carrier, and in the classifying, each of the plurality of subjects may be classified into one of the plurality of groups further based on the information.

The clinical psychological test may include an Alzheimer's disease assessment scale-cognitive subscale test and a preclinical Alzheimer's cognitive composite test, the obtaining may include further obtaining, for each of the plurality of subjects, information indicating whether the subject is an apolipoprotein Eε4 gene carrier, and in the classifying, for each of the plurality of subjects, the subject may be classified into the first group in any of the following cases: (1) if a first score obtained as a result of the Alzheimer's disease assessment scale-cognitive subscale test performed on the subject is less than a fifth threshold, the right hippocampus volume of the subject is greater than a sixth threshold, the information indicates the subject is an apolipoprotein Eε4 gene carrier, and a second score obtained as a result of the preclinical Alzheimer's cognitive composite test performed on the subject is less than a seventh threshold, the first score being the score; (2) if the first score of the subject is greater than the fifth threshold, the right hippocampus volume of the subject is greater than the sixth threshold, the information indicates the subject is an apolipoprotein Eε4 gene carrier, and the second score of the subject is less than the seventh threshold; (3) if the first score of the subject is greater than the fifth threshold and the right hippocampus volume of the subject is less than the sixth threshold; or (4) if the first score of the subject is less than the fifth threshold, the right hippocampus volume of the subject is less than the sixth threshold, the information indicates the subject is an apolipoprotein Eε4 gene carrier, and the second score of the subject is less than the seventh threshold, and classified into the second group in any of the following cases: (5) if the first score of the subject is less than the fifth threshold, the right hippocampus volume of the subject is greater than the sixth threshold, the information indicates the subject is an apolipoprotein Eε4 gene carrier, and the second score of the subject is greater than the seventh threshold; (6) if the first score of the subject is greater than the fifth threshold, the right hippocampus volume of the subject is greater than the sixth threshold, the information indicates the subject is an apolipoprotein Eε4 gene carrier, and the second score of the subject is greater than the seventh threshold; or (7) if the first score of the subject is less than the fifth threshold, the right hippocampus volume of the subject is greater than the sixth threshold, and the information indicates the subject is not an apolipoprotein Eε4 gene carrier.

The fifth threshold may be 20.0, the sixth threshold may be 3.651 [$cm^3$], and the seventh threshold may be 0.111.

Each of the plurality of subjects may have a positive beta-amyloid brain PET scan, the hippocampus volume of each of the plurality of subjects may be a left hippocampus volume of each of the plurality of subjects, and the clinical psychological test may be an Alzheimer's disease assessment scale-cognitive subscale test.

In the classifying, for each of the plurality of subjects, the subject may be classified into the first group if the score of the subject is greater than a first threshold and the left hippocampus volume of the subject is less than a second threshold, and classified into the second group if the score of the subject is less than the first threshold and the left hippocampus volume of the subject is greater than the second threshold.

The first threshold may be 14.0, and the second threshold may be 3.459 [$cm^3$].

The first threshold may be 12.0, and the second threshold may be 3.737 [$cm^3$].

The first threshold may be 21.0, and the second threshold may be 3.080 [$cm^3$].

The first threshold may be 24.0, and the second threshold may be 2.751 [$cm^3$].

In the classifying, for each of the plurality of subjects, a volume score value indicating a ratio between the left hippocampus volume of the subject and the score of the subject may be calculated, and each of the plurality of subjects may be classified into one of the plurality of groups based on the calculated volume score value.

The volume score value may be a ratio of the left hippocampus volume [$mm^3$] to the score, and in the classifying, for each of the plurality of subjects, the subject may be classified into the first group if the volume score value of the subject is less than 101.

The hippocampus volume of each of the plurality of subjects may be a left hippocampus volume of each of the plurality of subjects, the clinical psychological test may be an Alzheimer's disease assessment scale-cognitive subscale test, and in the classifying, for each of the plurality of subjects, a volume score value indicating a ratio between the left hippocampus volume of the subject and the score of the subject may be calculated, and each of the plurality of subjects may be classified into one of the plurality of groups based on the calculated volume score value.

The volume score value may be a ratio of the left hippocampus volume [$mm^3$] to the score, and in the classifying, for each of the plurality of subjects, the subject may be classified into the first group if the volume score value of the subject is less than 101.

A stratification device according to one aspect of the present invention includes: an obtainment unit configured to obtain, for each of a plurality of subjects with mild cognitive impairment, a score of a result of a clinical psychological test performed on the subject and a hippocampus volume of the subject; a classification unit configured to classify each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and an output unit configured to output a classification result of the classifying.

With the above stratification device, each of a plurality of subjects with mild cognitive impairment can be classified into one of a plurality of groups according to the risk of progressing to Alzheimer's disease in the future, in a manner different from conventional techniques that use beta-amyloid brain PET scan results.

Hereinafter, specific examples of the stratification method, etc., according to one aspect of the present invention will be described with reference to the drawings.

Each of the following embodiments is merely one specific example of the present invention. The values, shapes, elements, the arrangement and connection of the elements, the steps, and the order of the steps, etc., in the following embodiments are mere examples, and therefore do not limit the scope of the present invention. Moreover, the figures are schematic diagrams and are not necessarily precise illustrations. In each figure, elements that are essentially the same have the same reference signs, and repeated description thereof will be omitted or simplified.

In the present specification, the "stratification method" may also be referred to as a "classification method", and the "stratification device" may also be referred to as a "classification device".

Embodiment 1

Hereinafter, the stratification device according to Embodiment 1 that executes the stratification method according to Embodiment 1 will be described. This stratification device is a device that classifies each of a plurality of subjects with mild cognitive impairment into one of a plurality of groups according to the risk of progressing to Alzheimer's disease in the future. The plurality of groups include at least a first group, which is a high-risk group with a relatively high risk of progressing to Alzheimer's disease in the future, and a second group, which is a low-risk group with a relatively low risk of progressing to Alzheimer's disease in the future.

The stratification device that executes the above stratification method is one example of a device that executes a classification process that reflects findings by the inventors from a cohort study of a plurality of subjects with mild cognitive impairment.

<Configuration>

FIG. 2 is a block diagram illustrating one example of the configuration of stratification device 10 that executes the stratification method according to Embodiment 1.

Stratification device 10 is realized, for example, by a computer device. In this case, stratification device 10 is realized, for example, by a processor in the computer device executing a program stored in memory in the computer device.

As illustrated in FIG. 2, stratification device 10 includes obtainment unit 20, classification unit 30, and output unit 40.

For each of a plurality of subjects with mild cognitive impairment, obtainment unit 20 obtains a score obtained as a result of a clinical psychological test performed on the subject and the right hippocampus volume of the subject. The right hippocampus volume can be measured, for example, by performing an MRI test on the subject and performing image processing on the MRI image of the head obtained as a result of the MRI test.

In Embodiment 1, it is assumed that the clinical psychological test administered to the subjects is the Alzheimer's disease assessment scale-cognitive subscale (ADAS-cog) test.

Obtainment unit 20 may, for example, include a communication interface and obtain, from an external device via the communication interface, a score obtained as a result of performing the Alzheimer's disease assessment scale-cognitive subscale test on the subject (hereinafter also referred to as the "Alzheimer's disease assessment scale-cognitive subscale score") and the right hippocampus volume of the subject. Alternatively, obtainment unit may include a memory interface for reading data from portable memory (for example, USB memory) and obtain, from the portable memory via the memory interface, the Alzheimer's disease assessment scale-cognitive subscale score and the right hippocampus volume. Alternatively, obtainment unit 20 may include an input/output interface for receiving operations from a user using stratification device 10, and receive data input operations from the user via the input/output interface to obtain the Alzheimer's disease assessment scale-cognitive subscale score and the right hippocampus volume.

Classification unit 30 classifies the subjects into one of a plurality of groups including at least a first group at a relatively high risk of progressing to Alzheimer's disease in the future and a second group at a relatively low risk of progressing to Alzheimer's disease in the future, based on the Alzheimer's disease assessment scale-cognitive subscale score and the right hippocampus volume for each of the plurality of subjects. In Embodiment 1, the plurality of groups are exemplified as four groups including a first group, a second group, and further a third group and a fourth group.

Classification unit 30 performs the above classification based on the inventors' findings from a cohort study of a plurality of subjects with mild cognitive impairment.

More specifically, classification unit 30 classifies each of the plurality of subjects into (1) the first group if the Alzheimer's disease assessment scale-cognitive subscale score is greater than a first threshold and the right hippocampus volume is less than a second threshold, (2) the second group if the Alzheimer's disease assessment scale-cognitive subscale score is less than the first threshold and the right hippocampus volume is greater than the second threshold, (3) the third group if the Alzheimer's disease assessment scale-cognitive subscale score is greater than the first threshold and the right hippocampus volume is greater than the second threshold, and (4) the fourth group if the Alzheimer's disease assessment scale-cognitive subscale score is less than the first threshold and the right hippocampus volume is less than the second threshold. Here, classification unit 30 performs the above classification with the first threshold set at 20.0 and the second threshold set at 3.651 [$cm^3$].

Hereinafter, the findings from a cohort study of a plurality of subjects with mild cognitive impairment performed by the inventors will be described.

In the cohort study, the inventors conducted a follow-up study on a plurality of subjects with mild cognitive impairment for progression from mild cognitive impairment to Alzheimer's disease.

Figure 3:
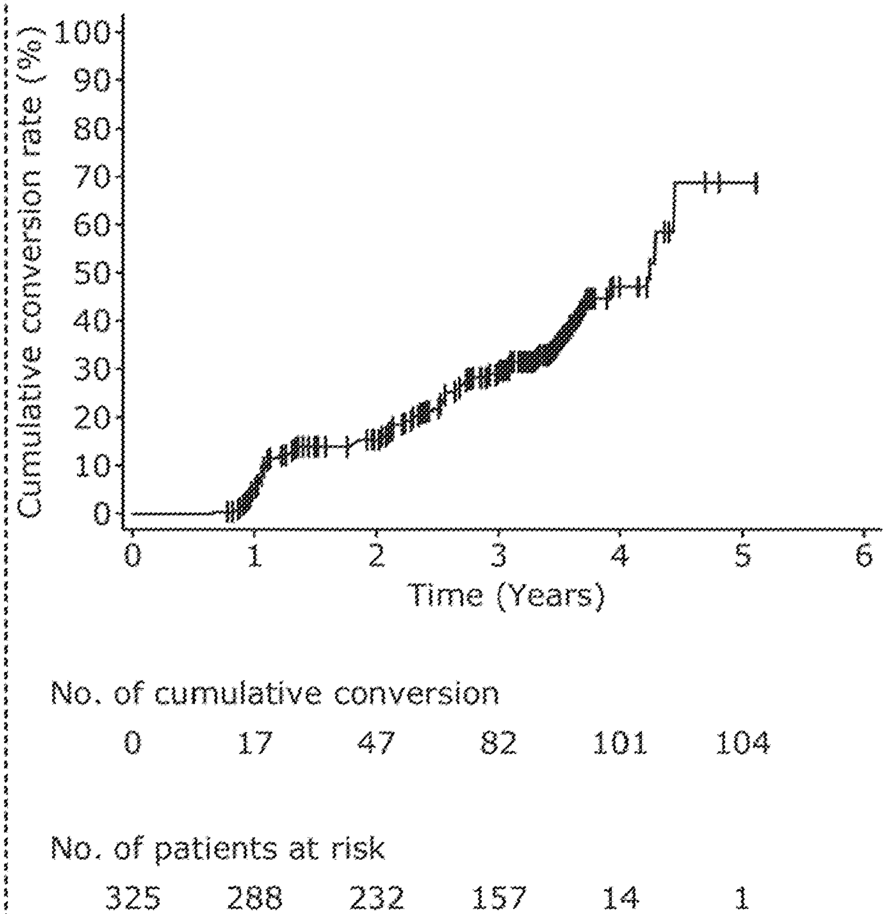
FIG. 3 illustrates a Kaplan-Meier curve showing the results of a follow-up study conducted by the inventors.

FIG. 3 illustrates a Kaplan-Meier curve showing the results of a follow-up study conducted by the inventors in a cohort study.

In the Kaplan-Meier curve illustrated in FIG. 3, the horizontal axis is the time [years] elapsed since the start of the follow-up study and the vertical axis is the cumulative conversion rate [%] of subjects who progressed from mild cognitive impairment to Alzheimer's disease.

As illustrated in FIG. 3, in the cohort study, the inventors conducted a follow-up study on 325 subjects with mild cognitive impairment for approximately five years regarding progression from mild cognitive impairment to Alzheimer's disease. During this approximately five-year period, 104 subjects progressed from mild cognitive impairment to Alzheimer's disease.

In a cohort study, the inventors classified each of the plurality of subjects at the start of the follow-up study into (1) group C (corresponding to the first group) of subjects with an Alzheimer's disease assessment scale-cognitive subscale score greater than a first threshold and a right hippocampus volume less than a second threshold, (2) group B (corresponding to the second group) of subjects with an Alzheimer's disease assessment scale-cognitive subscale score less than the first threshold and a right hippocampus volume greater than the second threshold, (3) group D (corresponding to the third group) of subjects with an Alzheimer's disease assessment scale-cognitive subscale score greater than the first threshold and a right hippocampus volume greater than the second threshold, or (4) group A (corresponding to the fourth group) of subjects with an Alzheimer's disease assessment scale-cognitive subscale score less than the first threshold and a right hippocampus volume less than the second threshold. They then evaluated the Kaplan-Meier curve showing the follow-up results per-group after classification.

Figure 4:
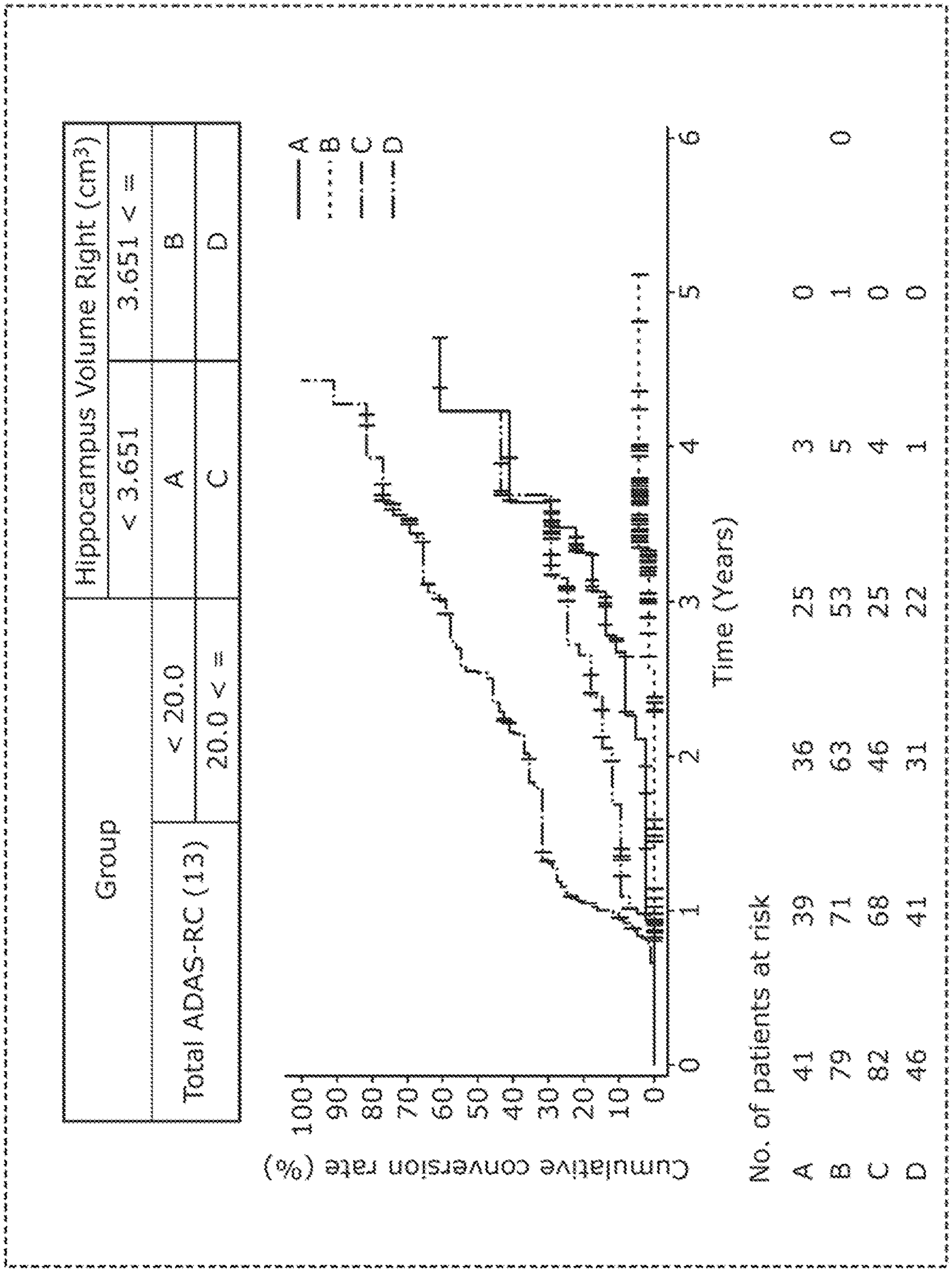
FIG. 4 illustrates Kaplan-Meier curves showing the results of a follow-up study conducted per group by the inventors.

FIG. 4 illustrates Kaplan-Meier curves showing the results of a follow-up study conducted per-group by the inventors in a cohort study.

In the Kaplan-Meier curves illustrated in FIG. 4, the horizontal axis is the time [years] elapsed since the start of the follow-up study and the vertical axis is the cumulative conversion rate [%] of subjects who progressed from mild cognitive impairment to Alzheimer's disease.

The Kaplan-Meier curves illustrated in FIG. 4 indicate that, of the first to fourth groups, the first group is at a relatively high risk of progressing to Alzheimer's disease in the future at the start of the follow-up study, and the second group is at a relatively low risk of progressing to Alzheimer's disease in the future at the start of the follow-up study.

In this way, through a cohort study, the inventors found that by classifying each of the plurality of subjects with mild cognitive impairment into (1) the first group if the Alzheimer's disease assessment scale-cognitive subscale score is greater than a first threshold and the right hippocampus volume is less than a second threshold, (2) the second group if the Alzheimer's disease assessment scale-cognitive subscale score is less than the first threshold and the right hippocampus volume is greater than the second threshold, (3) the third group if the Alzheimer's disease assessment scale-cognitive subscale score is greater than the first threshold and the right hippocampus volume is greater than the second threshold, and (4) the fourth group if the Alzheimer's disease assessment scale-cognitive subscale score is less than the first threshold and the right hippocampus volume is less than the second threshold, it is possible to classify the plurality of subjects with mild cognitive impairment into a plurality of groups (in this case, four groups) including a first group at a relatively high risk of progressing to Alzheimer's disease in the future and a second group at a relatively low risk of progressing to Alzheimer's disease in the future.

The inventors also found through the cohort study that in the above classification, a first threshold value of 20.0±1 SD is preferable and a second threshold value of 3.651±1 SD [$cm^3$] is preferable. Here, the 1 SD of the first threshold is 6.3 and the 1 SD of the second threshold is 0.653 [$cm^3$].

Next, returning again to FIG. 2, the description of stratification device 10 will continue.

Output unit 40 outputs the classification result by classification unit 30.

Output unit 40 may, for example, include an output port, and output a display control signal including the classification result to display an image showing the classification result on an external display device via the output port. Alternatively, output unit 40 may, for example, include a communication interface, and transmit the classification result information including the classification result to an external device via the communication interface.

<Operations>

Hereinafter, operations performed by stratification device 10 configured as described above will be described with reference to the drawings.

Figure 5:
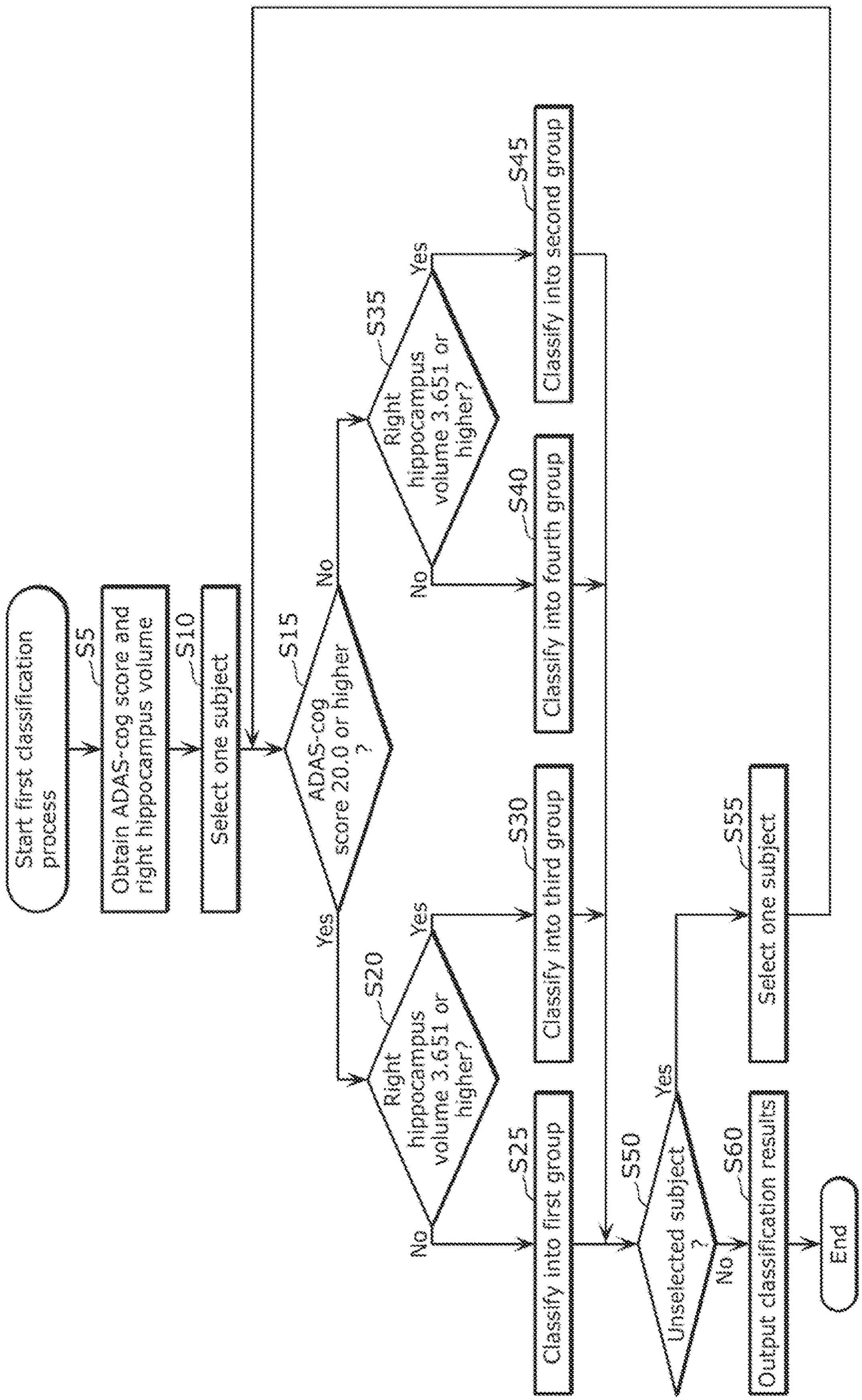
FIG. 5 is a flowchart of the first classification process according to Embodiment 1.

FIG. 5 is a flowchart of the first classification process performed by stratification device 10. This first classification process classifies the subjects into one of four groups that include at least a first group at a relatively high risk of progressing to Alzheimer's disease in the future and a second group at a relatively low risk of progressing to Alzheimer's disease in the future, based on the Alzheimer's disease assessment scale-cognitive subscale score and the right hippocampus volume for each of the plurality of subjects.

The first classification process is initiated, for example, when a user of stratification device 10 performs an operation on stratification device 10 to initiate the first classification process.

Once the first classification process is initiated, obtainment unit 20 obtains, for each of the plurality of subjects with mild cognitive impairment, the score obtained as a result of performing the Alzheimer's disease assessment scale-cognitive subscale (ADAS-cog) test on the subject (hereinafter also referred to as "ADAS-cog score") and the right hippocampus volume of the subject (step S5).

Once the ADAS-cog scores and right hippocampus volumes of the plurality of subjects are obtained, classification unit 30 selects one subject from the plurality of subjects (step S10). Classification unit 30 then checks whether the ADAS-cog score of the selected subject is 20.0 or higher (step S15).

If the ADAS-cog score is 20.0 or higher in step S15 (step S15: Yes), classification unit 30 checks whether the right hippocampus volume of the selected subject is 3.651 or higher (step S20).

If the right hippocampus volume is not 3.651 or higher in the process of step S20 (step S20: No), classification unit 30 classifies the selected subject into the first group (step S25).

If the right hippocampus volume is 3.651 or higher in the process of step S20 (step S20: Yes), classification unit 30 classifies the selected subject into the third group (step S30).

If the ADAS-cog score is not 20.0 or higher in step S15 (step S15: No), classification unit 30 checks whether the right hippocampus volume of the selected subject is 3.651 or higher (step S35).

If the right hippocampus volume is not 3.651 or higher in the process of step S35 (step S35: No), classification unit 30 classifies the selected subject into the fourth group (step S40).

If the right hippocampus volume is 3.651 or higher in the process of step S35 (step S35: Yes), classification unit 30 classifies the selected subject into the second group (step S45).

When the processing of step S25 is completed, when the processing of step S30 is completed, when the processing of step S40 is completed, and when the processing of step S45 is completed, classification unit 30 checks whether there is an unselected subject among the plurality of subjects (step S50). Here, "unselected subject" means a subject who has not yet been selected in the processing of step S10 and has not yet been selected in the processing of step S55 (to be described later) in the loop process that proceeds from the processing of step S15 through the processing of step S50: Yes, and back to the processing of step S15.

If there is an unselected subject in the process of step S50 (step S50: Yes), classification unit 30 selects one subject from the unselected subjects (step S55).

After the processing of step S55 is completed, processing proceeds to step S15.

If there are no unselected subjects in the process of step S50 (step S50: No), output unit 40 outputs the classification results that classification unit 30 has performed for each of the plurality of subjects (step S60).

After the process of step S60 is completed, stratification device 10 completes its first classification process.

<Observations>

With stratification device 10 configured as described above, a plurality of subjects with mild cognitive impairment can be classified into one of a plurality of groups including a first group at a relatively high risk of progressing to Alzheimer's disease in the future and a second group at a relatively low risk of progressing to Alzheimer's disease in the future.

Accordingly, by using stratification device 10 to pre-classify a plurality of subjects with mild cognitive impairment, it is possible to effectively conduct prevention trials, etc., for individuals who progress from mild cognitive impairment to Alzheimer's disease.

With stratification device 10 configured as described above, the above classification can be performed in a manner different from conventional techniques. Stated differently, with stratification device 10, the above classification does not use the results of beta-amyloid brain PET scans, a relatively expensive test required by conventional techniques.

Accordingly, by using stratification device 10, the above classification can be performed at a lower cost and more efficiently than when using conventional techniques.

Embodiment 2

Hereinafter, the stratification device according to Embodiment 2 that executes the stratification method according to Embodiment 1 will be described. Embodiment 2 is equivalent to Embodiment 1 with some changes in the functions of stratification device 10. As described in Embodiment 1, stratification device 10 classifies a plurality of subjects with mild cognitive impairment based on their scores obtained as a result of performing the Alzheimer's disease assessment scale-cognitive subscale test and their right hippocampus volumes. In contrast, the stratification device according to Embodiment 2 classifies a plurality of subjects with mild cognitive impairment based on their scores obtained as a result of performing the Alzheimer's disease assessment scale-cognitive subscale test, their right hippocampus volumes, and additionally, whether they are an apolipoprotein Eε4 gene carrier. The following description of the stratification device according to Embodiment 2 will focus on the differences from stratification device 10, omitting detailed descriptions of the same elements as those in stratification device 10, as they have already been described.

<Configuration>

Figure 6:
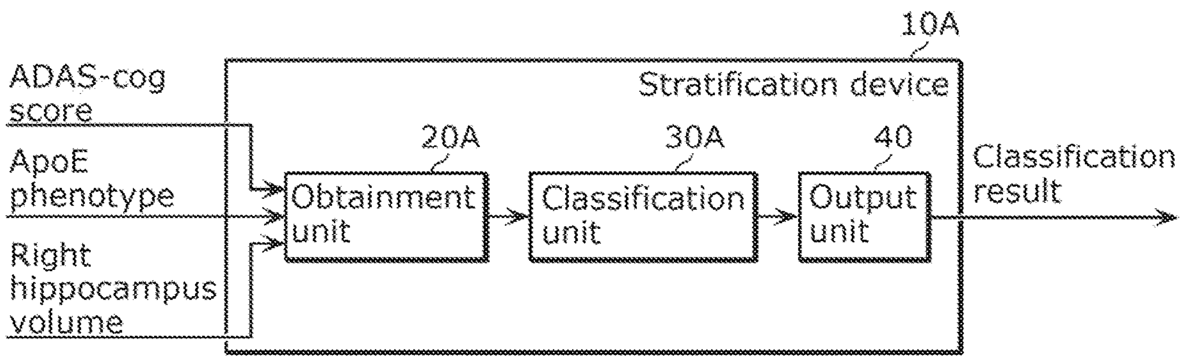
FIG. 6 is a block diagram illustrating one example of the configuration of the stratification method according to Embodiment 2.

FIG. 6 is a block diagram illustrating one example of the configuration of stratification device 10A that executes the stratification method according to Embodiment 2.

As illustrated in FIG. 6, stratification device 10A differs from stratification device 10 according to Embodiment 1 in that obtainment unit 20 has been changed to obtainment unit 20A and classification unit 30 has been changed to classification unit 30A.

For each of a plurality of subjects with mild cognitive impairment, obtainment unit 20A obtains, in addition to the score obtained as a result of performing the Alzheimer's disease assessment scale-cognitive subscale test on the subject and the right hippocampus volume of the subject, information indicating whether subject is an apolipoprotein Eε4 gene carrier (hereinafter also referred to as "ApoE phenotype").

Classification unit 30A classifies the subjects into one of a plurality of groups including at least a first group at a relatively high risk of progressing to Alzheimer's disease in the future and a second group at a relatively low risk of progressing to Alzheimer's disease in the future, based on the Alzheimer's disease assessment scale-cognitive subscale score, the right hippocampus volume, and the ApoE phenotype for each of the plurality of subjects. In Embodiment 2, the plurality of groups are exemplified as eight groups including a first group, a second group, and further a third group, a fourth group, a fifth group, a sixth group, a seventh group, and an eighth group.

Classification unit 30A performs the above classification based on the inventors' findings from a cohort study of a plurality of subjects with mild cognitive impairment.

More specifically, classification unit 30A classifies each of the plurality of subjects into (1) the first group if the ApoE phenotype indicates that the subject is an apolipoprotein Eε4 gene carrier (hereinafter also referred to as "ApoE positive"), the Alzheimer's disease assessment scale-cognitive subscale score is greater than a first threshold, and the right hippocampus volume is less than a second threshold, (2) the second group if the ApoE phenotype indicates ApoE positive, the Alzheimer's disease assessment scale-cognitive subscale score is less than the first threshold, and the right hippocampus volume is greater than the second threshold, (3) the third group if the ApoE phenotype indicates ApoE positive, the Alzheimer's disease assessment scale-cognitive subscale score is greater than the first threshold, and the right hippocampus volume is greater than the second threshold, (4) the fourth group if the ApoE phenotype indicates ApoE positive, the Alzheimer's disease assessment scale-cognitive subscale score is less than the first threshold, and the right hippocampus volume is less than the second threshold, (5)

the fifth group if the ApoE phenotype indicates that the subject is not an apolipoprotein Eε4 gene carrier (hereinafter also referred to as "ApoE negative"), the Alzheimer's disease assessment scale-cognitive subscale score is greater than the first threshold, and the right hippocampus volume is less than the second threshold, (6) the sixth group if the ApoE phenotype indicates ApoE negative, the Alzheimer's disease assessment scale-cognitive subscale score is less than the first threshold, and the right hippocampus volume is greater than the second threshold, (7) the seventh group if the ApoE phenotype indicates ApoE negative, the Alzheimer's disease assessment scale-cognitive subscale score is greater than the first threshold, and the right hippocampus volume is greater than the second threshold, and (8) the eighth group if the ApoE phenotype indicates ApoE negative, the Alzheimer's disease assessment scale-cognitive subscale score is less than the first threshold, and the right hippocampus volume is less than the second threshold.

Here, classification unit 30A performs the above classification with the first threshold set at 20.0 and the second threshold set at 3.651 [$cm^3$].

Hereinafter, the findings from a cohort study of a plurality of subjects with mild cognitive impairment performed by the inventors will be described.

In the cohort study, at the start of the follow-up study, the inventors first classified the subjects into two groups: (A) group α of subjects who are not apolipoprotein Eε4 gene carriers and (B) group β of subjects who are apolipoprotein Eε4 gene carriers. Then, as the second-stage classification, for each of group α and group β, (1) subjects with an Alzheimer's disease assessment scale-cognitive subscale score greater than the first threshold and a right hippocampus volume less than the second threshold were classified into group C (corresponding to the first group in group α, the fifth group in group β), (2) subjects with an Alzheimer's disease assessment scale-cognitive subscale score less than the first threshold and a right hippocampus volume greater than the second threshold were classified into group β (corresponding to the second group in group α, the sixth group in group β), (3) subjects with an Alzheimer's disease assessment scale-cognitive subscale score greater than the first threshold and a right hippocampus volume greater than the second threshold were classified into group D (corresponding to the third group in group α, the seventh group in group β), and (4) subjects with an Alzheimer's disease assessment scale-cognitive subscale score less than the first threshold and a right hippocampus volume less than the second threshold were classified into group A (corresponding to the fourth group in group α, the eighth group in group β). They then evaluated the Kaplan-Meier curves showing the follow-up study results per-group after classification.

Figure 7A:
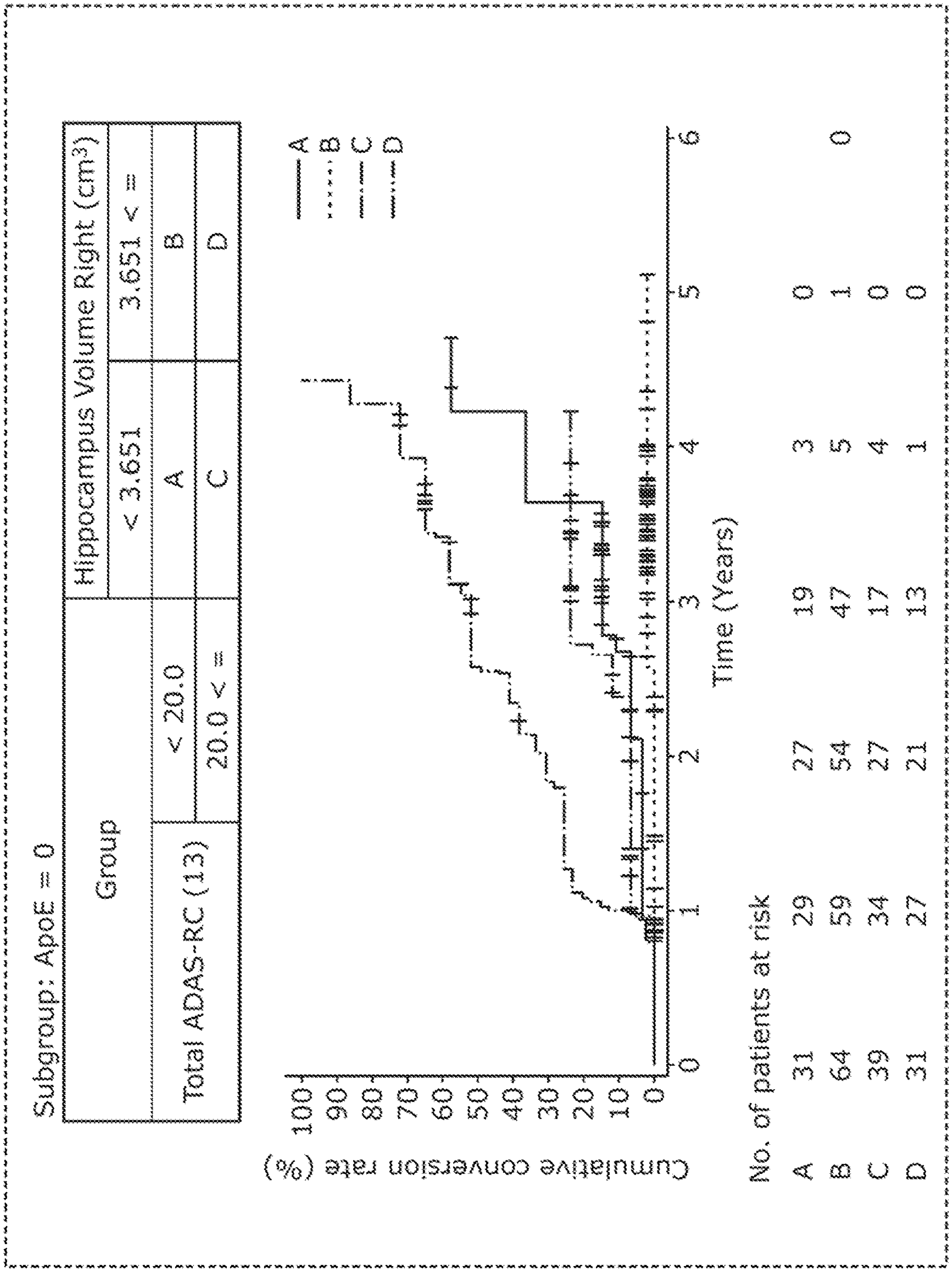
FIG. 7A illustrates Kaplan-Meier curves showing the results of a follow-up study conducted per group by the inventors.
Figure 7B:
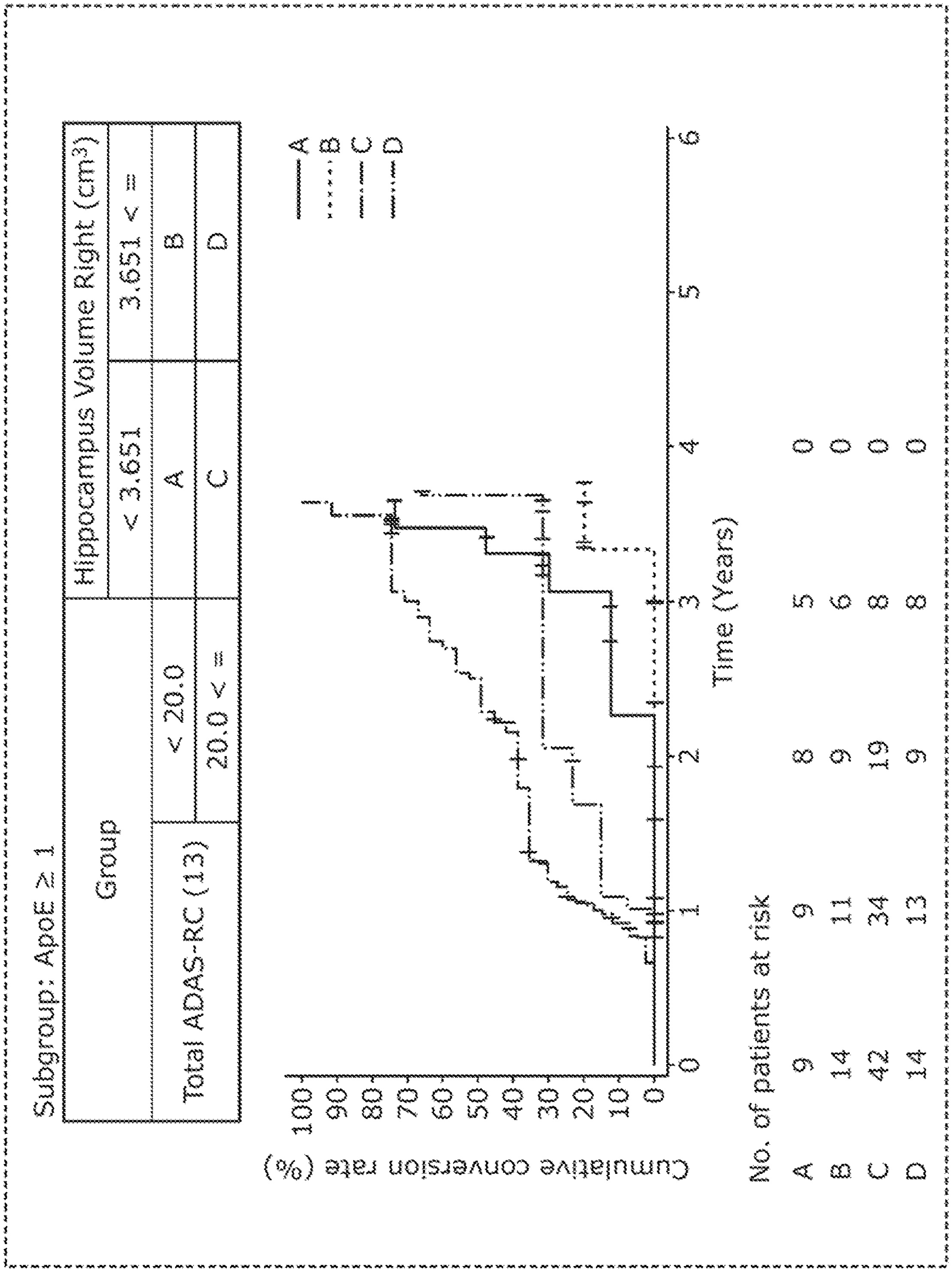
FIG. 7B illustrates Kaplan-Meier curves showing the results of a follow-up study conducted per group by the inventors.

FIG. 7A and FIG. 7B illustrate Kaplan-Meier curves showing the results of a follow-up study conducted per-group by the inventors in a cohort study.

FIG. 7A illustrates Kaplan-Meier curves showing the results of per-group follow-up studies conducted on group α, and FIG. 7B illustrates Kaplan-Meier curves showing the results of per-group follow-up studies conducted on group β.

In the Kaplan-Meier curves illustrated in FIG. 7A and FIG. 7B, the horizontal axis is the time [years] elapsed since the start of the follow-up study and the vertical axis is the cumulative conversion rate [%] of subjects who progressed from mild cognitive impairment to Alzheimer's disease.

The Kaplan-Meier curves illustrated in FIG. 7A and FIG. 7B indicate that, of the first to eighth groups, the first group is at a relatively high risk of progressing to Alzheimer's disease in the future at the start of the follow-up study, and the second group is at a relatively low risk of progressing to Alzheimer's disease in the future at the start of the follow-up study.

In this way, through a cohort study, the inventors found that by classifying each of the plurality of subjects with mild cognitive impairment into (1) the first group if the ApoE phenotype indicates ApoE positive, the Alzheimer's disease assessment scale-cognitive subscale score is greater than a first threshold, and the right hippocampus volume is less than a second threshold, (2) the second group if the ApoE phenotype indicates ApoE positive, the Alzheimer's disease assessment scale-cognitive subscale score is less than the first threshold, and the right hippocampus volume is greater than the second threshold, (3) the third group if the ApoE phenotype indicates ApoE positive, the Alzheimer's disease assessment scale-cognitive subscale score is greater than the first threshold, and the right hippocampus volume is greater than the second threshold, (4) the fourth group if the ApoE phenotype indicates ApoE positive, the Alzheimer's disease assessment scale-cognitive subscale score is less than the first threshold, and the right hippocampus volume is less than the second threshold, (5) the fifth group if the ApoE phenotype indicates that the subject is not an apolipoprotein Eε4 gene carrier (hereinafter also referred to as "ApoE negative"), the Alzheimer's disease assessment scale-cognitive subscale score is greater than the first threshold, and the right hippocampus volume is less than the second threshold, (6) the sixth group if the ApoE phenotype indicates ApoE negative, the Alzheimer's disease assessment scale-cognitive subscale score is less than the first threshold, and the right hippocampus volume is greater than the second threshold, (7) the seventh group if the ApoE phenotype indicates ApoE negative, the Alzheimer's disease assessment scale-cognitive subscale score is greater than the first threshold, and the right hippocampus volume is greater than the second threshold, and (8) the eighth group if the ApoE phenotype indicates ApoE negative, the Alzheimer's disease assessment scale-cognitive subscale score is less than the first threshold, and the right hippocampus volume is less than the second threshold, it is possible to classify the plurality of subjects with mild cognitive impairment into a plurality of groups (in this case, eight groups) including a first group at a relatively high risk of progressing to Alzheimer's disease in the future and a second group at a relatively low risk of progressing to Alzheimer's disease in the future.

Based on the Kaplan-Meier curves illustrated in FIG. 7A and FIG. 7B, the classification results of the second-stage classification for group α, which consists of subjects who are not apolipoprotein Eε4 gene carriers, are more accurate than the classification results of the second-stage classification for group β, which consists of subjects who are apolipoprotein Eε4 gene carriers. The results show that it is possible to classify subjects with mild cognitive impairment into one of a plurality of groups including a group at a relatively high risk of progressing to Alzheimer's disease in the future and a group at a relatively low risk of progressing to Alzheimer's disease in the future.

Thus, through a cohort study, the inventors have found that, based on the Alzheimer's disease assessment scale-cognitive subscale score, the right hippocampus volume, and additionally the ApoE phenotype, subjects can be more accurately classified into one of a plurality of groups including at least a first group at a relatively high risk of progressing to Alzheimer's disease in the future and a second group at a relatively low risk of progressing to Alzheimer's disease in the future.

<Operations>

Hereinafter, operations performed by stratification device 10A configured as described above will be described with reference to the drawings.

Stratification device 10A performs a second classification process, some of which has been modified from the first classification process performed by stratification device 10.

Figure 8A:
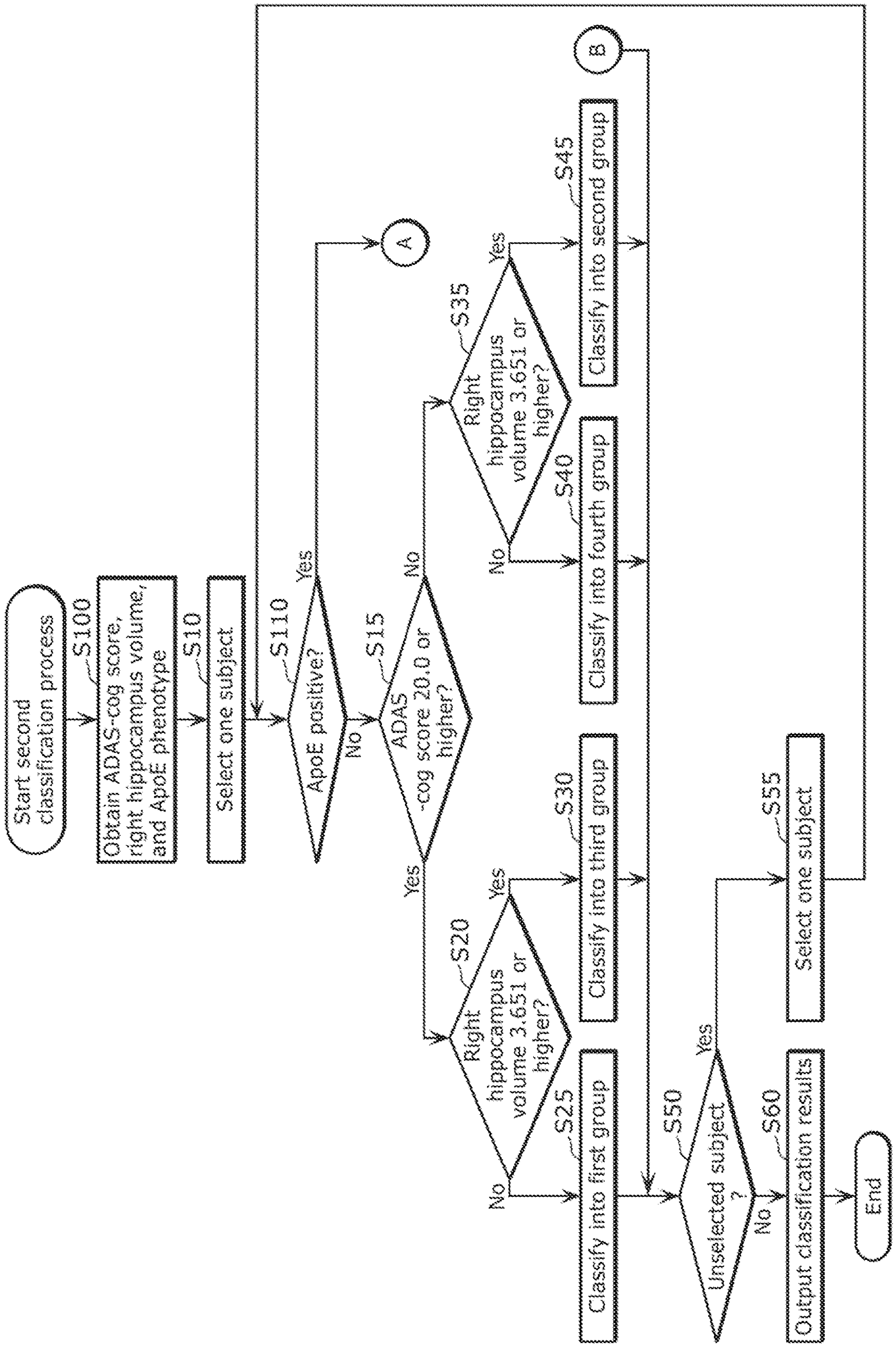
FIG. 8A is a flowchart of the second classification process according to Embodiment 2.
Figure 8B:
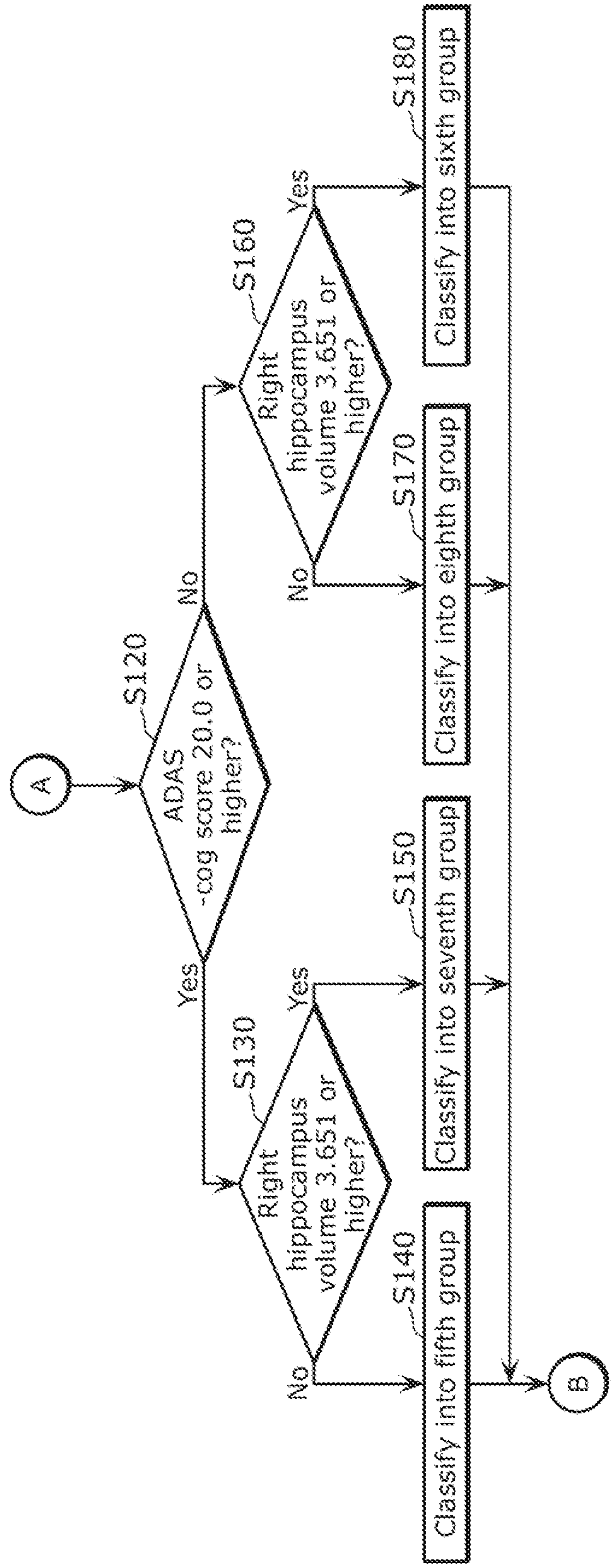
FIG. 8B is a flowchart of the second classification process according to Embodiment 2.

FIG. 8A and FIG. 8B are flowcharts of the second classification process performed by stratification device 10A.

As illustrated in FIG. 8A and FIG. 8B, the second classification process is equivalent to the first classification process added with steps S100 through S180.

Accordingly, the following will focus on the processing of steps S100 through S180.

Once the second classification process is initiated, obtainment unit 20A obtains the ADAS-cog score, the right hippocampus volume, and the ApoE phenotype for each of the plurality of subjects with mild cognitive impairment (step S100).

After the processing of step S100 is completed, processing proceeds to step S10.

When the processing of step S10 is completed and when the processing of step S55 is completed, classification unit 30A checks whether the ApoE phenotype of the selected subject indicates ApoE positive (step S110).

In the process of step S110, if the ApoE phenotype of the selected subject does not indicate ApoE positive (step S110: No), processing proceeds to step S15.

If the ApoE phenotype of the selected subject indicates ApoE positive in step S110 (step S110: Yes), classification unit 30A checks whether the ADAS-cog score of the selected subject is 20.0 or higher (step S120).

If the ADAS-cog score is 20.0 or higher in step S120 (step S120: Yes), classification unit 30A checks whether the right hippocampus volume of the selected subject is 3.651 or higher (step S130).

If the right hippocampus volume is not 3.651 or higher in the process of step S130 (step S130: No), classification unit 30A classifies the selected subject into the fifth group (step S140).

If the right hippocampus volume is 3.651 or higher in the process of step S130 (step S130: Yes), classification unit 30A classifies the selected subject into the seventh group (step S150).

If the ADAS-cog score is not 20.0 or higher in step S120 (step S120: No), classification unit 30A checks whether the right hippocampus volume of the selected subject is 3.651 or higher (step S160).

If the right hippocampus volume is not 3.651 or higher in the process of step S160 (step S160: No), classification unit 30A classifies the selected subject into the eighth group (step S170).

If the right hippocampus volume is 3.651 or higher in the process of step S160 (step S160: Yes), classification unit 30A classifies the selected subject into the sixth group (step S180).

When the processing of step S140 is completed, when the processing of step S150 is completed, when the processing of step S170 is completed, and when the processing of step S180 is completed, processing proceeds to step S50.

After the process of step S60 is completed, stratification device 10A completes its second classification process.

<Observations>

Stratification device 10A configured as described above classifies a plurality of subjects with mild cognitive impairment based on their Alzheimer's disease assessment scale-cognitive subscale scores, their right hippocampus volumes, and additionally, whether they are an apolipoprotein Eε4 gene carrier. This allows stratification device 10A to classify the subject with greater accuracy.

Embodiment 3

Hereinafter, the stratification device according to Embodiment 3 that executes the stratification method according to Embodiment 3 will be described. The stratification device according to Embodiment 3 is equivalent to stratification device 10 according to Embodiment 1 with some changes in the functions. As described in Embodiment 1, stratification device 10 classifies a plurality of subjects with mild cognitive impairment based on their scores obtained as a result of performing the Alzheimer's disease assessment scale-cognitive subscale test, which is a clinical psychological test conducted on the subjects, and their right hippocampus volumes. In contrast, the stratification device according to Embodiment 3 classifies a plurality of subjects with mild cognitive impairment based on preclinical Alzheimer cognitive composite (PACC) scores obtained by performing one or more clinical psychological tests on the subjects, and their right hippocampus volumes. The following description of the stratification device according to Embodiment 3 will focus on the differences from stratification device 10, omitting detailed descriptions of the same elements as those in stratification device 10, as they have already been described.

<Configuration>

Figure 9:
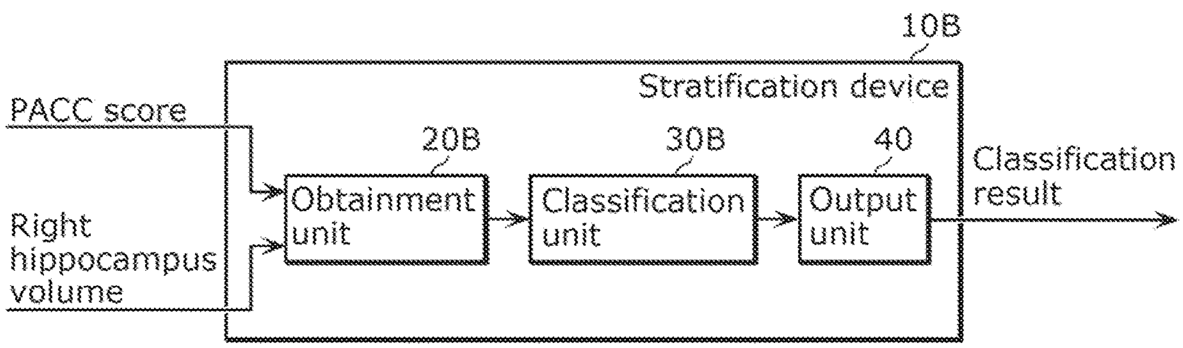
FIG. 9 is a block diagram illustrating one example of the configuration of the stratification method according to Embodiment 3.

FIG. 9 is a block diagram illustrating one example of the configuration of stratification device 10B that implements the stratification method according to Embodiment 3.

As illustrated in FIG. 9, stratification device 10B differs from stratification device 10 according to Embodiment 1 in that obtainment unit 20 has been changed to obtainment unit 20B and classification unit 30 has been changed to classification unit 30B.

For each of a plurality of subjects with mild cognitive impairment, obtainment unit 20B obtains a score obtained as a result of performing several cognitive function tests for preclinical Alzheimer's disease on the subject (hereinafter also referred to as "preclinical Alzheimer's cognitive composite score") and the right hippocampus volume of the subject.

Classification unit 30B classifies the subjects into one of a plurality of groups including at least a first group at a relatively high risk of progressing to Alzheimer's disease in the future and a second group at a relatively low risk of progressing to Alzheimer's disease in the future, based on the preclinical Alzheimer's cognitive composite score and the right hippocampus volume for each of the plurality of subjects. In Embodiment 3, the plurality of groups are exemplified as four groups including a first group, a second group, and further a third group and a fourth group.

Classification unit 30B performs the above classification based on the inventors' findings from a cohort study of a plurality of subjects with mild cognitive impairment.

More specifically, classification unit 30B classifies each of the plurality of subjects into (1) the first group if the preclinical Alzheimer's cognitive composite score is less than a third threshold and the right hippocampus volume is less than a fourth threshold, (2) the second group if the preclinical Alzheimer's cognitive composite score is greater than the third threshold and the right hippocampus volume is greater than the fourth threshold, (3) the third group if the preclinical Alzheimer's cognitive composite score is less than the third threshold and the right hippocampus volume is greater than the fourth threshold, and (4) the fourth group if the preclinical Alzheimer's cognitive composite score is greater than the third threshold and the right hippocampus volume is less than the fourth threshold. Here, classification unit 30B performs the above classification with the fourth threshold set at 0.111 and the fourth threshold set at 3.651 [$cm^3$].

Hereinafter, the findings from a cohort study of a plurality of subjects with mild cognitive impairment performed by the inventors will be described.

In the cohort study, at the start of the follow-up study, the inventors first classified the subjects into two groups: (A) group $\alpha$ of subjects who are not apolipoprotein E$\varepsilon$4 gene carriers and (B) group $\beta$ of subjects who are apolipoprotein E$\varepsilon$4 gene carriers. Then, as the second-stage classification, for each of group $\alpha$ and group $\beta$, (1) subjects with a preclinical Alzheimer's cognitive composite score less than a third threshold and a right hippocampus volume less than a fourth threshold were classified into group A (corresponding to the first group in group $\alpha$, the fifth group in group $\beta$), (2) subjects with a preclinical Alzheimer's cognitive composite score greater than the third threshold and a right hippocampus volume greater than the fourth threshold were classified into group D (corresponding to the second group in group $\alpha$, the sixth group in group $\beta$), (3) subjects with a preclinical Alzheimer's cognitive composite score less than the third threshold and a right hippocampus volume greater than the fourth threshold were classified into group $\beta$ (corresponding to the third group in group $\alpha$, the seventh group in group $\beta$), and (4) subjects with a preclinical Alzheimer's cognitive composite score greater than the third threshold and a right hippocampus volume less than the fourth threshold were classified into group C (corresponding to the fourth group in group $\alpha$, the eighth group in group $\beta$). They then evaluated the Kaplan-Meier curves showing the per-group follow-up results.

Figure 10A:
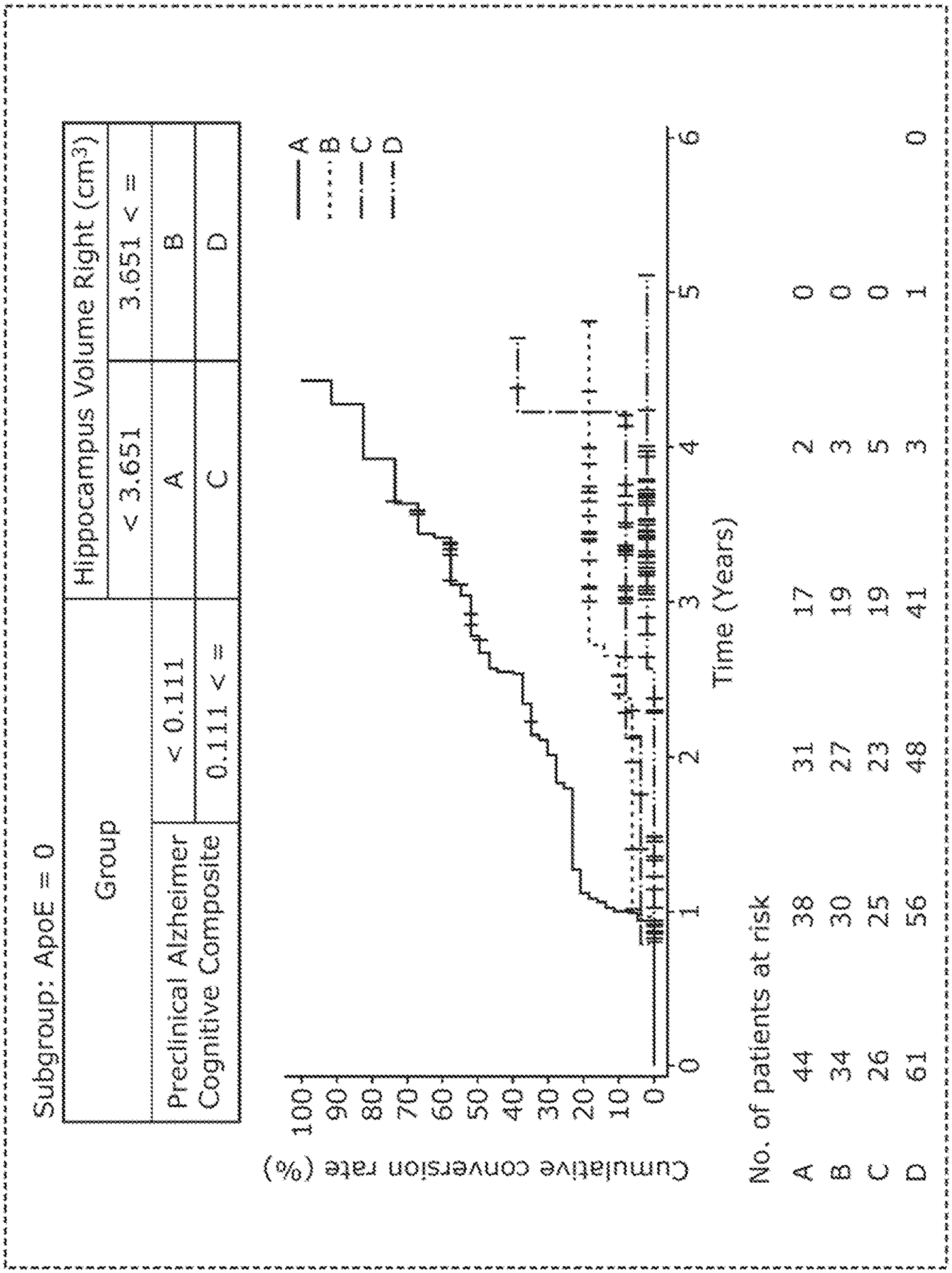
FIG. 10A illustrates Kaplan-Meier curves showing the results of a follow-up study conducted per group by the inventors.
Figure 10B:
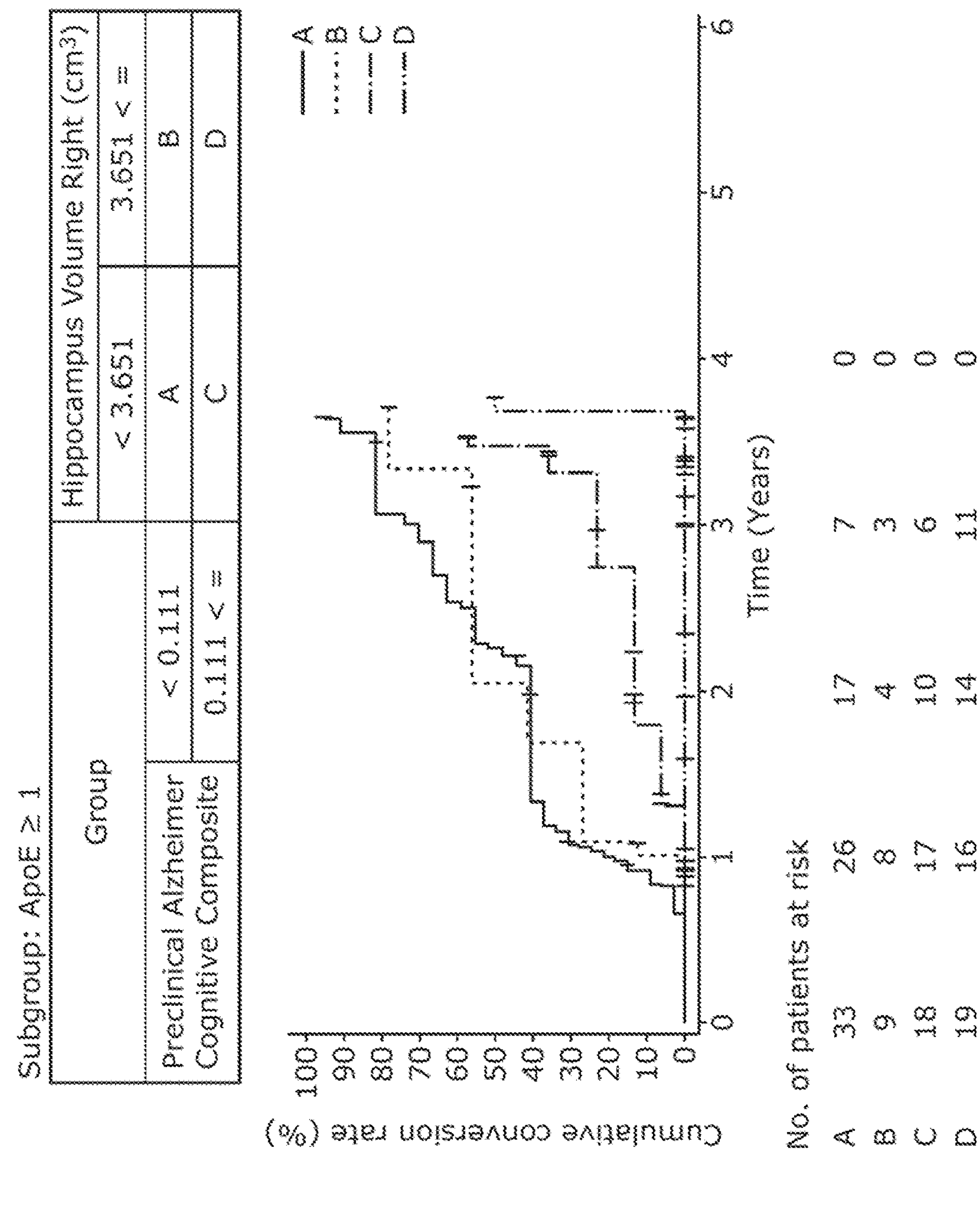
FIG. 10B illustrates Kaplan-Meier curves showing the results of a follow-up study conducted per group by the inventors.

FIG. 10A and FIG. 10B illustrate Kaplan-Meier curves showing the results of a follow-up study conducted per-group by the inventors in a cohort study.

FIG. 10A illustrates Kaplan-Meier curves showing the results of per-group follow-up studies conducted on group $\alpha$, and FIG. 10B illustrates Kaplan-Meier curves showing the results of per-group follow-up studies conducted on group $\beta$.

In the Kaplan-Meier curves illustrated in FIG. 10A and FIG. 10B, the horizontal axis is the time [years] elapsed since the start of the follow-up study and the vertical axis is the cumulative conversion rate [%] of subjects who progressed from mild cognitive impairment to Alzheimer's disease.

The Kaplan-Meier curves illustrated in FIG. 10A and FIG. 10B indicate that, of the first to eighth groups, the first and fifth groups are at a relatively high risk of progressing to Alzheimer's disease in the future at the start of the follow-up study, and the second and sixth groups are at a relatively low risk of progressing to Alzheimer's disease in the future at the start of the follow-up study.

In this way, through a cohort study, the inventors found that by classifying each of the plurality of subjects with mild cognitive impairment into (1) the first group if the preclinical Alzheimer's cognitive composite score is less than a third threshold and the right hippocampus volume is less than a fourth threshold, (2) the second group if the preclinical Alzheimer's cognitive composite score is greater than the third threshold and the right hippocampus volume is greater than the fourth threshold, (3) the third group if the preclinical Alzheimer's cognitive composite score is less than the third threshold and the right hippocampus volume is greater than the fourth threshold, and (4) the fourth group if the preclinical Alzheimer's cognitive composite score is greater than the third threshold and the right hippocampus volume is less than the fourth threshold, it is possible to classify the plurality of subjects with mild cognitive impairment into a plurality of groups (in this case, four groups) including a first group at a relatively high risk of progressing to Alzheimer's disease in the future and a second group at a relatively low risk of progressing to Alzheimer's disease in the future.

The inventors also found through the cohort study that in the above classification, a first threshold value of 0.111±1 SD is preferable and a second threshold value of 3.651±1 SD [$cm^3$] is preferable. Here, the 1 SD of the first threshold is 2.630 and the 1 SD of the second threshold is 0.653 [$cm^3$].

<Operations>

Hereinafter, operations performed by stratification device 10B configured as described above will be described with reference to the drawings.

Figure 11:
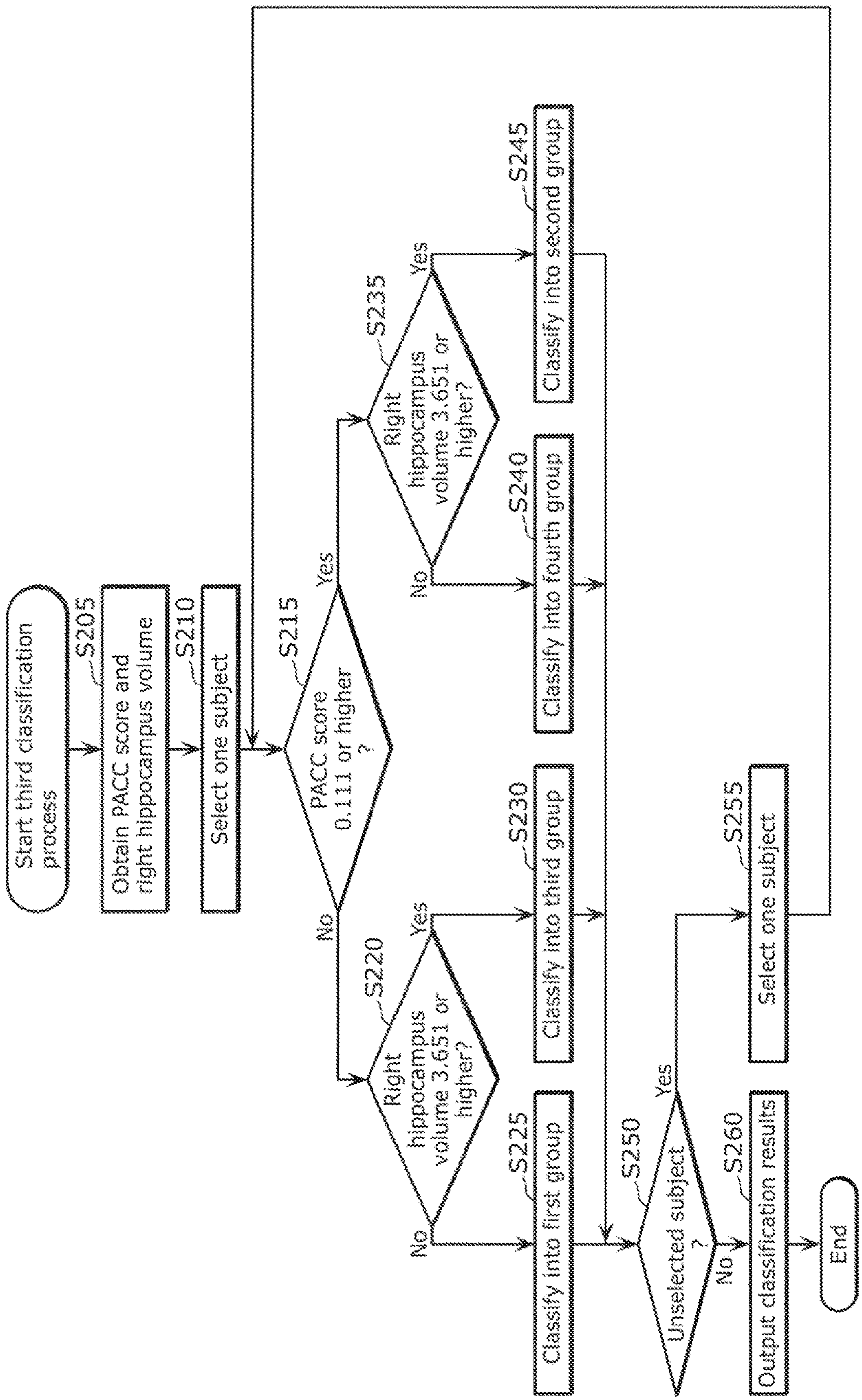
FIG. 11 is a flowchart of the third classification process according to Embodiment 3.

FIG. 11 is a flowchart of the third classification process performed by stratification device 10B. This third classification process classifies the subjects into one of four groups that include at least a first group at a relatively high risk of progressing to Alzheimer's disease in the future and a second group at a relatively low risk of progressing to Alzheimer's disease in the future, based on the preclinical Alzheimer's cognitive composite score and the right hippocampus volume for each of the plurality of subjects.

The third classification process is initiated, for example, when a user of stratification device 10B performs an operation on stratification device 10B to initiate the third classification process.

Once the third classification process is initiated, obtainment unit 20B obtains, for each of the plurality of subjects with mild cognitive impairment, the score obtained as a result of performing the preclinical Alzheimer cognitive composite (PACC) test on the subject (hereinafter also referred to as "PACC score") and the right hippocampus volume of the subject (step S205).

Once the PACC scores and right hippocampus volumes of the plurality of subjects are obtained, classification unit 30B selects one subject from the plurality of subjects (step S210). Classification unit 30B then checks whether the PACC score of the selected subject is 0.111 or higher (step S215).

If the PACC score is not 0.111 or higher in step S215 (step S215: No), classification unit 30B checks whether the right hippocampus volume of the selected subject is 3.651 or higher (step S220).

If the right hippocampus volume is not 3.651 or higher in the process of step S220 (step S220: No), classification unit 30B classifies the selected subject into the first group (step S225).

If the right hippocampus volume is 3.651 or higher in the process of step S220 (step S220: Yes), classification unit 30B classifies the selected subject into the third group (step S230). If the PACC score is 0.111 or higher in step S215 (step S215: Yes), classification unit 30B checks whether the right hippocampus volume of the selected subject is 3.651 or higher (step S235). If the right hippocampus volume is not 3.651 or higher in the process of step S235 (step S235: No), classification unit 30B classifies the selected subject into the fourth group (step S240).

If the right hippocampus volume is 3.651 or higher in the process of step S235 (step S235: Yes), classification unit 30B classifies the selected subject into the second group (step S245).

When the processing of step S225 is completed, when the processing of step S230 is completed, when the processing of step S240 is completed, and when the processing of step S245 is completed, classification unit 30B checks whether there is an unselected subject among the plurality of subjects (step S250). Here, "unselected subject" means a subject who has not yet been selected in the processing of step S210 and has not yet been selected in the processing of step S255 (to be described later) in the loop process that proceeds from the processing of step S215 through the processing of step S250: Yes, and back to the processing of step S215.

If there is an unselected subject in the process of step S250 (step S250: Yes), classification unit 30B selects one subject from the unselected subjects (step S255).

After the processing of step S255 is completed, processing proceeds to step S215.

If there are no unselected subjects in the process of step S250 (step S250: No), output unit 40 outputs the classification results that classification unit 30B has performed for each of the plurality of subjects (step S260).

After the process of step S260 is completed, stratification device 10B completes its third classification process.

<Observations>

With stratification device 10B configured as described above, a plurality of subjects with mild cognitive impairment can be classified into one of a plurality of groups including a first group at a relatively high risk of progressing to Alzheimer's disease in the future and a second group at a relatively low risk of progressing to Alzheimer's disease in the future.

Accordingly, by using stratification device 10B to pre-classify a plurality of subjects with mild cognitive impairment, it is possible to effectively conduct prevention trials, etc., for individuals who progress from mild cognitive impairment to Alzheimer's disease.

With stratification device 10B configured as described above, the above classification can be performed in a manner different from conventional techniques. Stated differently, with stratification device 10B, the above classification does not use the results of beta-amyloid brain PET scans, a relatively expensive test required by conventional techniques.

Accordingly, by using stratification device 10B, the above classification can be performed at a lower cost and more efficiently than when using conventional techniques.

Embodiment 4

Hereinafter, the stratification device according to Embodiment 4 that implements the stratification method according to Embodiment 4 will be described. The stratification device according to Embodiment 4 is equivalent to stratification device 10B according to Embodiment 3 with some changes in the functions. As described in Embodiment 3, stratification device 10B classifies a plurality of subjects with mild cognitive impairment based on their preclinical Alzheimer's cognitive composite scores and their right hippocampus volumes. In contrast, the stratification device according to Embodiment 4 classifies a plurality of subjects with mild cognitive impairment based on their preclinical Alzheimer's cognitive composite scores, their right hippocampus volumes, and additionally, whether they are an apolipoprotein Eε4 gene carrier. The following description of the stratification device according to Embodiment 4 will focus on the differences from stratification device 10B, omitting detailed descriptions of the same elements as those in stratification device 10B, as they have already been described.

<Configuration>

Figure 12:
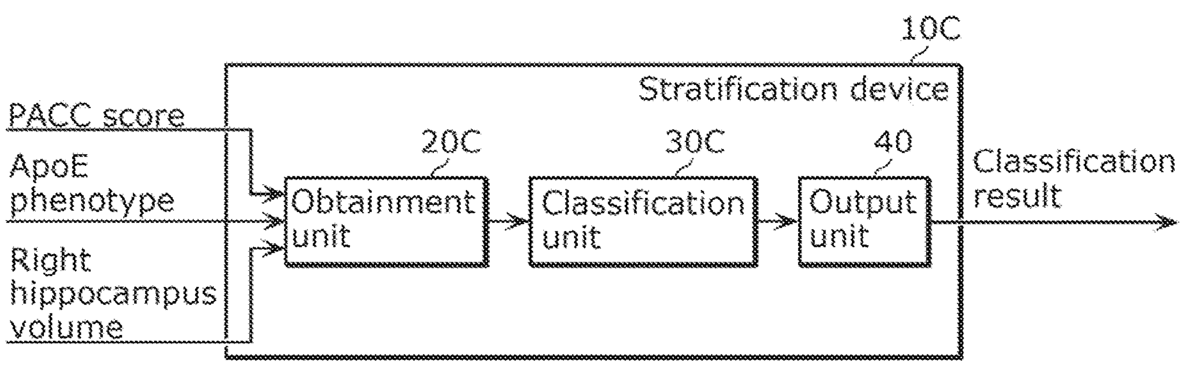
FIG. 12 is a block diagram illustrating one example of the configuration of the stratification method according to Embodiment 4.

FIG. 12 is a block diagram illustrating one example of the configuration of stratification device 10C that implements the stratification method according to Embodiment 4.

As illustrated in FIG. 12, stratification device 10C differs from stratification device 10B according to Embodiment 3 in that obtainment unit 20B has been changed to obtainment unit 20C and classification unit 30B has been changed to classification unit 30C.

For each of a plurality of subjects with mild cognitive impairment, obtainment unit 20C obtains a score obtained as a result of performing the preclinical Alzheimer's cognitive composite test on the subject, the right hippocampus volume of the subject, and the ApoE phenotype.

Classification unit 30C classifies the subjects into one of a plurality of groups including at least a first group at a relatively high risk of progressing to Alzheimer's disease in the future and a second group at a relatively low risk of progressing to Alzheimer's disease in the future, based on the preclinical Alzheimer's cognitive composite score, the right hippocampus volume, and the ApoE phenotype for each of the plurality of subjects. In Embodiment 4, the plurality of groups are exemplified as eight groups including a first group, a second group, and further a third group, a fourth group, a fifth group, a sixth group, a seventh group, and an eighth group.

Classification unit 30C performs the above classification based on the inventors' findings from a cohort study of a plurality of subjects with mild cognitive impairment.

More specifically, classification unit 30C classifies each of the plurality of subjects into (1) the first group if the ApoE phenotype indicates ApoE positive, the preclinical Alzheimer's cognitive composite score is less than a third threshold, and the right hippocampus volume is less than a fourth threshold, (2) the second group if the ApoE phenotype indicates ApoE positive, the preclinical Alzheimer's cognitive composite score is greater than the third threshold, and the right hippocampus volume is greater than the fourth threshold, (3) the third group if the ApoE phenotype indicates ApoE positive, the preclinical Alzheimer's cognitive composite score is less than the third threshold, and the right hippocampus volume is greater than the fourth threshold, (4) the fourth group if the ApoE phenotype indicates ApoE positive, the preclinical Alzheimer's cognitive composite score is greater than the third threshold, and the right hippocampus volume is less than the fourth threshold, (5) the fifth group if the ApoE phenotype indicates ApoE negative, the preclinical Alzheimer's cognitive composite score is less than the third threshold, and the right hippocampus volume is less than the fourth threshold, (6) the sixth group if the ApoE phenotype indicates ApoE negative, the preclinical Alzheimer's cognitive composite score is greater than the third threshold, and the right hippocampus volume is greater than the fourth threshold, (7) the seventh group if the ApoE phenotype indicates ApoE negative, the preclinical Alzheimer's cognitive composite score is less than the third threshold, and the right hippocampus volume is greater than the fourth threshold, and (8) the eighth group if the ApoE phenotype indicates ApoE negative, the preclinical Alzheimer's cognitive composite score is greater than the third threshold, and the right hippocampus volume is less than the fourth threshold. Here, classification unit 30C performs the above classification with the third threshold set at 0.111 and the fourth threshold set at 3.651 [$cm^3$].

Hereinafter, the findings from a cohort study of a plurality of subjects with mild cognitive impairment performed by the inventors will be described.

The Kaplan-Meier curves illustrated in FIG. 10A and FIG. 10B indicate that, of the first to eighth groups, the first group is at a relatively high risk of progressing to Alzheimer's disease in the future at the start of the follow-up study, and the second group is at a relatively low risk of progressing to Alzheimer's disease in the future at the start of the follow-up study.

In this way, through a cohort study, the inventors found that by classifying each of the plurality of subjects with mild cognitive impairment into (1) the first group if the ApoE phenotype indicates ApoE positive, the preclinical Alzheimer's cognitive composite score is less than a third threshold, and the right hippocampus volume is less than a fourth threshold, (2) the second group if the ApoE phenotype indicates ApoE positive, the preclinical Alzheimer's cognitive composite score is greater than the third threshold, and the right hippocampus volume is greater than the fourth threshold, (3) the third group if the ApoE phenotype indicates ApoE positive, the preclinical Alzheimer's cognitive composite score is less than the third threshold, and the right hippocampus volume is greater than the fourth threshold, (4) the fourth group if the ApoE phenotype indicates ApoE positive, the preclinical Alzheimer's cognitive composite score is greater than the third threshold, and the right hippocampus volume is less than the fourth threshold, (5) the fifth group if the ApoE phenotype indicates ApoE negative, the preclinical Alzheimer's cognitive composite score is less than the third threshold, and the right hippocampus volume is less than the fourth threshold, (6) the sixth group if the ApoE phenotype indicates ApoE negative, the preclinical Alzheimer's cognitive composite score is greater than the third threshold, and the right hippocampus volume is greater than the fourth threshold, (7) the seventh group if the ApoE phenotype indicates ApoE negative, the preclinical Alzheimer's cognitive composite score is less than the third threshold, and the right hippocampus volume is greater than the fourth threshold, and (8) the eighth group if the ApoE phenotype indicates ApoE negative, the preclinical Alzheimer's cognitive composite score is greater than the third threshold, and the right hippocampus volume is less than the fourth threshold, it is possible to classify the plurality of subjects with mild cognitive impairment into a plurality of groups (in this case, eight groups) including a first group at a relatively high risk of progressing to Alzheimer's disease in the future and a second group at a relatively low risk of progressing to Alzheimer's disease in the future.

Based on the Kaplan-Meier curves illustrated in FIG. 10A and FIG. 10B, the classification results of the second-stage classification for group α, which consists of subjects who are not an apolipoprotein Eε4 gene carrier, are more accurate than the classification results of the second-stage classification for group β, which consists of subjects who are apolipoprotein Eε4 gene carriers. The results show that it is possible to classify subjects with mild cognitive impairment into one of a plurality of groups including a group at a relatively high risk of progressing to Alzheimer's disease in the future and a group at a relatively low risk of progressing to Alzheimer's disease in the future.

Thus, through a cohort study, the inventors have found that, based on the preclinical Alzheimer's cognitive composite score, the right hippocampus volume, and additionally the ApoE phenotype, subjects can be more accurately classified into one of a plurality of groups including at least a first group at a relatively high risk of progressing to Alzheimer's disease in the future and a second group at a relatively low risk of progressing to Alzheimer's disease in the future.

<Operations>

Hereinafter, operations performed by stratification device 10C configured as described above will be described with reference to the drawings.

Stratification device 10C performs a fourth classification process, some of which has been modified from the third classification process performed by stratification device 10B.

Figure 13A:
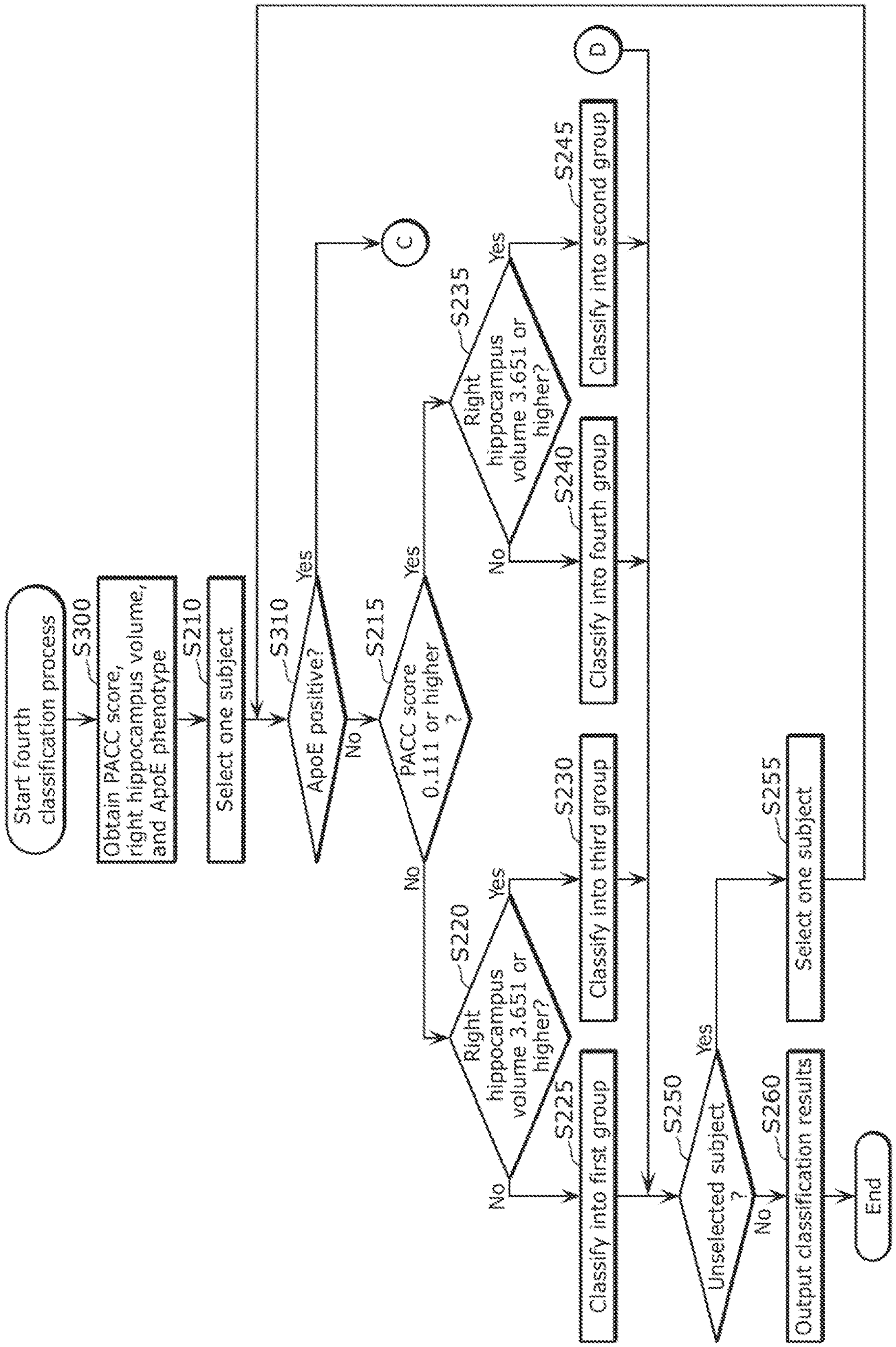
FIG. 13A is a flowchart of the fourth classification process according to Embodiment 4.
Figure 13B:
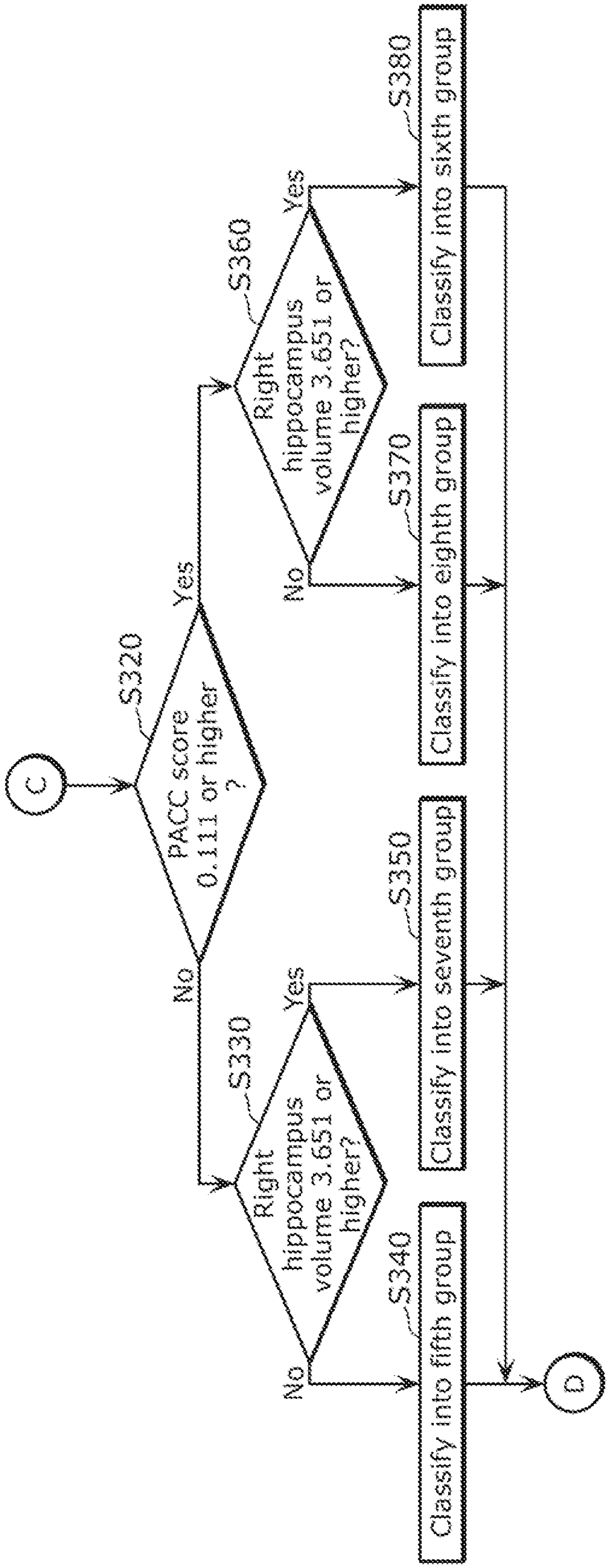
FIG. 13B is a flowchart of the fourth classification process according to Embodiment 4.

FIG. 13A and FIG. 13B are flowcharts of the fourth classification process performed by stratification device 10C.

As illustrated in FIG. 13A and FIG. 13B, the fourth classification process is equivalent to the third classification process added with steps S300 through S380.

Accordingly, the following will focus on the processing of steps S300 through S380.

Once the fourth classification process is initiated, obtainment unit 20C obtains the PACC score, the right hippocampus volume, and the ApoE phenotype for each of the plurality of subjects with mild cognitive impairment (step S300).

After the processing of step S300 is completed, processing proceeds to step S210.

When the processing of step S210 is completed and when the processing of step S255 is completed, classification unit 30C checks whether the ApoE phenotype of the selected subject indicates ApoE positive (step S310).

In the process of step S310, if the ApoE phenotype of the selected subject does not indicate ApoE positive (step S310: No), processing proceeds to step S215.

If the ApoE phenotype of the selected subject indicates ApoE positive in step S310 (step S310: Yes), classification unit 30C checks whether the PACC score of the selected subject is 0.111 or higher (step S320).

If the PACC score is not 0.111 or higher in step S320 (step S320: No), classification unit 30C checks whether the right hippocampus volume of the selected subject is 3.651 or higher (step S330).

If the right hippocampus volume is not 3.651 or higher in the process of step S330 (step S330: No), classification unit 30C classifies the selected subject into the fifth group (step S340).

If the right hippocampus volume is 3.651 or higher in the process of step S330 (step S330: Yes), classification unit 30C classifies the selected subject into the seventh group (step S350).

If the PACC score is 0.111 or higher in step S320 (step S320: Yes), classification unit 30C checks whether the right hippocampus volume of the selected subject is 3.651 or higher (step S360).

If the right hippocampus volume is not 3.651 or higher in the process of step S360 (step S360: No), classification unit 30C classifies the selected subject into the eighth group (step S370).

If the right hippocampus volume is 3.651 or higher in the process of step S360 (step S360: Yes), classification unit 30C classifies the selected subject into the sixth group (step S380).

When the processing of step S340 is completed, when the processing of step S350 is completed, when the processing of step S370 is completed, and when the processing of step S380 is completed, processing proceeds to step S250.

After the process of step S260 is completed, stratification device 10C completes its fourth classification process.

<Observations>

Stratification device 10C configured as described above classifies a plurality of subjects with mild cognitive impairment based on their preclinical Alzheimer's cognitive composite scores, their right hippocampus volumes, and additionally, whether they are an apolipoprotein Eε4 gene carrier. This allows stratification device 10C to classify the subject with greater accuracy.

Embodiment 5

Hereinafter, the stratification device that executes the stratification method according to Embodiment 5 will be described. The stratification device according to Embodiment 5 is equivalent to stratification device 10 according to Embodiment 1 with some changes in the functions. As described in Embodiment 1, stratification device 10 classifies a plurality of subjects with mild cognitive impairment based on their scores obtained as a result of performing the Alzheimer's disease assessment scale-cognitive subscale test and their right hippocampus volumes. In contrast, the stratification method according to Embodiment 5 classifies a plurality of subjects with mild cognitive impairment based on their scores obtained as a result of performing the Alzheimer's disease assessment scale-cognitive subscale test, their right hippocampus volumes, and additionally, their preclinical Alzheimer's cognitive composite scores and whether they are an apolipoprotein Eε4 gene carrier. The following description of the stratification device that implements the stratification method according to Embodiment 5 will focus on the differences from stratification device 10, omitting detailed descriptions of the same elements as those in stratification device 10, as they have already been described.

<Configuration>

Figure 14:
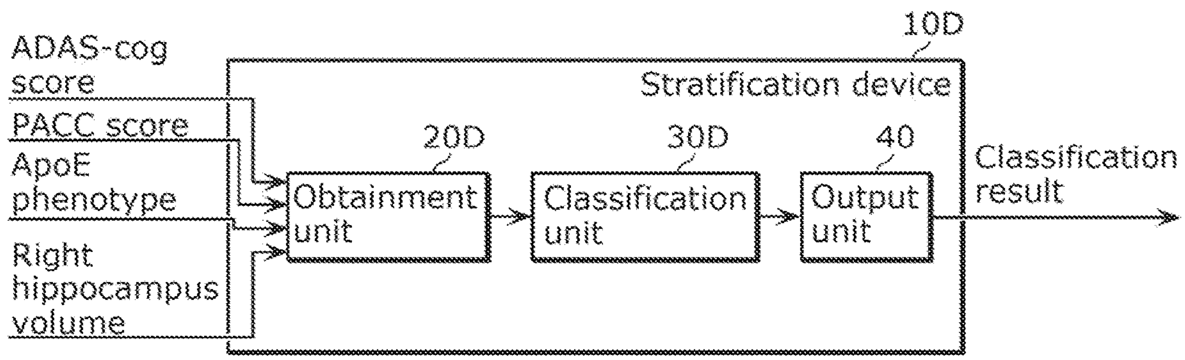
FIG. 14 is a block diagram illustrating one example of the configuration of the stratification method according to Embodiment 5.

FIG. 14 is a block diagram illustrating one example of the configuration of stratification device 10D that executes the stratification method according to Embodiment 5.

As illustrated in FIG. 14, stratification device 10D differs from stratification device 10 according to Embodiment 1 in that obtainment unit 20 has been changed to obtainment unit 20D and classification unit 30 has been changed to classification unit 30D.

For each of a plurality of subjects with mild cognitive impairment, obtainment unit 20D obtains, in addition to the score obtained as a result of performing the Alzheimer's disease assessment scale-cognitive subscale test on the subject and the right hippocampus volume of the subject, a score obtained as a result of performing the preclinical Alzheimer's cognitive composite test on the subject, and information indicating whether the subject is an apolipoprotein Eε4 gene carrier (ApoE phenotype).

Classification unit 30D classifies the subjects into one of a plurality of groups including at least sixth, seventh, and eighth groups at a relatively high risk of progressing to Alzheimer's disease in the future and first and second groups at a relatively low risk of progressing to Alzheimer's disease in the future, based on the Alzheimer's disease assessment scale-cognitive subscale score, the right hippocampus volume, the ApoE phenotype, and the preclinical Alzheimer's cognitive composite score for each of the plurality of subjects. In Embodiment 5, the plurality of groups are exemplified as eight groups including a first group, a second group, a sixth group, a seventh group, an eighth group, and further a third group, a fourth group, and a fifth group.

Classification unit 30D performs the above classification based on the inventors' findings from a cohort study of a plurality of subjects with mild cognitive impairment.

More specifically, classification unit 30D classifies each of the plurality of subjects into (1) the first group if the Alzheimer's disease assessment scale-cognitive subscale score is less than the fifth threshold, the right hippocampus volume is greater than the sixth threshold, and the ApoE phenotype indicates ApoE negative, (2) the second group if the Alzheimer's disease assessment scale-cognitive subscale score is greater than the fifth threshold, the right hippocampus volume is greater than the sixth threshold, and the ApoE phenotype indicates ApoE positive, and the preclinical Alzheimer's cognitive composite score is greater than the seventh threshold, or if the Alzheimer's disease assessment scale-cognitive subscale score is less than the fifth threshold, the right hippocampus volume is greater than the sixth threshold, the ApoE phenotype indicates ApoE positive, and the preclinical Alzheimer's cognitive composite score is greater than the seventh threshold, (3) the third group if the Alzheimer's disease assessment scale-cognitive subscale score is less than the fifth threshold, the right hippocampus volume is less than the sixth threshold, the ApoE phenotype indicates ApoE positive, and the preclinical Alzheimer's cognitive composite score is greater than the seventh threshold, (4) the fourth group if the Alzheimer's disease assessment scale-cognitive subscale score is less than the fifth threshold, the right hippocampus volume is less than the sixth threshold, and the ApoE phenotype indicates ApoE negative, (5) the fifth group if the Alzheimer's disease assessment scale-cognitive subscale score is greater than the fifth threshold, the right hippocampus volume is greater than the sixth threshold, and the ApoE phenotype indicates ApoE negative, (6) the sixth group if the Alzheimer's disease assessment scale-cognitive subscale score is greater than the fifth threshold, the right hippocampus volume is greater than the sixth threshold, the ApoE phenotype indicates ApoE positive, and the preclinical Alzheimer's cognitive composite score is less than the seventh threshold, or if the Alzheimer's disease assessment scale-cognitive subscale score is less than the fifth threshold, the right hippocampus volume is greater than the sixth threshold, the ApoE phenotype indicates ApoE positive, and the preclinical Alzheimer's cognitive composite score is less than the seventh threshold, (7) the seventh group if the Alzheimer's disease assessment scale-cognitive subscale score is greater than the fifth threshold, and the right hippocampus volume is less than the sixth threshold, and (8) the eighth group if the Alzheimer's disease assessment scale-cognitive subscale score is less than the fifth threshold, the right hippocampus volume is less than the sixth threshold, the ApoE phenotype indicates ApoE positive, and the preclinical Alzheimer's cognitive composite score is less than the seventh threshold. Here, classification unit 30D performs the above classification with the fifth threshold set at 20.0, the sixth threshold set at 3.651 [$cm^3$], and the seventh threshold set at 0.111.

Hereinafter, the findings from a cohort study of a plurality of subjects with mild cognitive impairment performed by the inventors will be described.

In the cohort study, the inventors classified each of the plurality of subjects into (1) the first group of subjects with an Alzheimer's disease assessment scale-cognitive subscale score less than the fifth threshold, a right hippocampus volume greater than the sixth threshold, and an ApoE phenotype indicating ApoE negative, (2) the second group of subjects with an Alzheimer's disease assessment scale-cognitive subscale score greater than the fifth threshold, a right hippocampus volume greater than the sixth threshold, an ApoE phenotype indicating ApoE positive, and a preclinical Alzheimer's cognitive composite score greater than the seventh threshold, or subjects with an Alzheimer's disease assessment scale-cognitive subscale score less than the fifth threshold, a right hippocampus volume greater than the sixth threshold, an ApoE phenotype indicating ApoE positive, and a preclinical Alzheimer's cognitive composite score greater than the seventh threshold, (3) the third group of subjects with an Alzheimer's disease assessment scale-cognitive subscale score less than the fifth threshold, a right hippocampus volume less than the sixth threshold, an ApoE phenotype indicating ApoE positive, and a preclinical Alzheimer's cognitive composite score greater than the seventh threshold, (4) the fourth group of subjects with an Alzheimer's disease assessment scale-cognitive subscale score less than the fifth threshold, a right hippocampus volume less than the sixth threshold, and an ApoE phenotype indicating ApoE negative, (5) the fifth group of subjects with an Alzheimer's disease assessment scale-cognitive subscale score greater than the fifth threshold, a right hippocampus volume greater than the sixth threshold, and an ApoE phenotype indicating ApoE negative, (6) the sixth group of subjects with an Alzheimer's disease assessment scale-cognitive subscale score greater than the fifth threshold, a right hippocampus volume greater than the sixth threshold, an ApoE phenotype indicating ApoE positive, and a preclinical Alzheimer's cognitive composite score less than the seventh threshold, or subjects with an Alzheimer's disease assessment scale-cognitive subscale score less than the fifth threshold, a right hippocampus volume greater than the sixth threshold, an ApoE phenotype indicating ApoE positive, and a preclinical Alzheimer's cognitive composite score less than the seventh threshold, (7) the seventh group of subjects with an Alzheimer's disease assessment scale-cognitive subscale score greater than the fifth threshold, and a right hippocampus volume less than the sixth threshold, or (8) the eighth group of subjects with an Alzheimer's disease assessment scale-cognitive subscale score less than the fifth threshold, a right hippocampus volume less than the sixth threshold, an ApoE phenotype indicating ApoE positive, and a preclinical Alzheimer's cognitive composite score less than the seventh threshold, and evaluated the Kaplan-Meier curves showing the follow-up results for each group after classification.

Figure 15A:
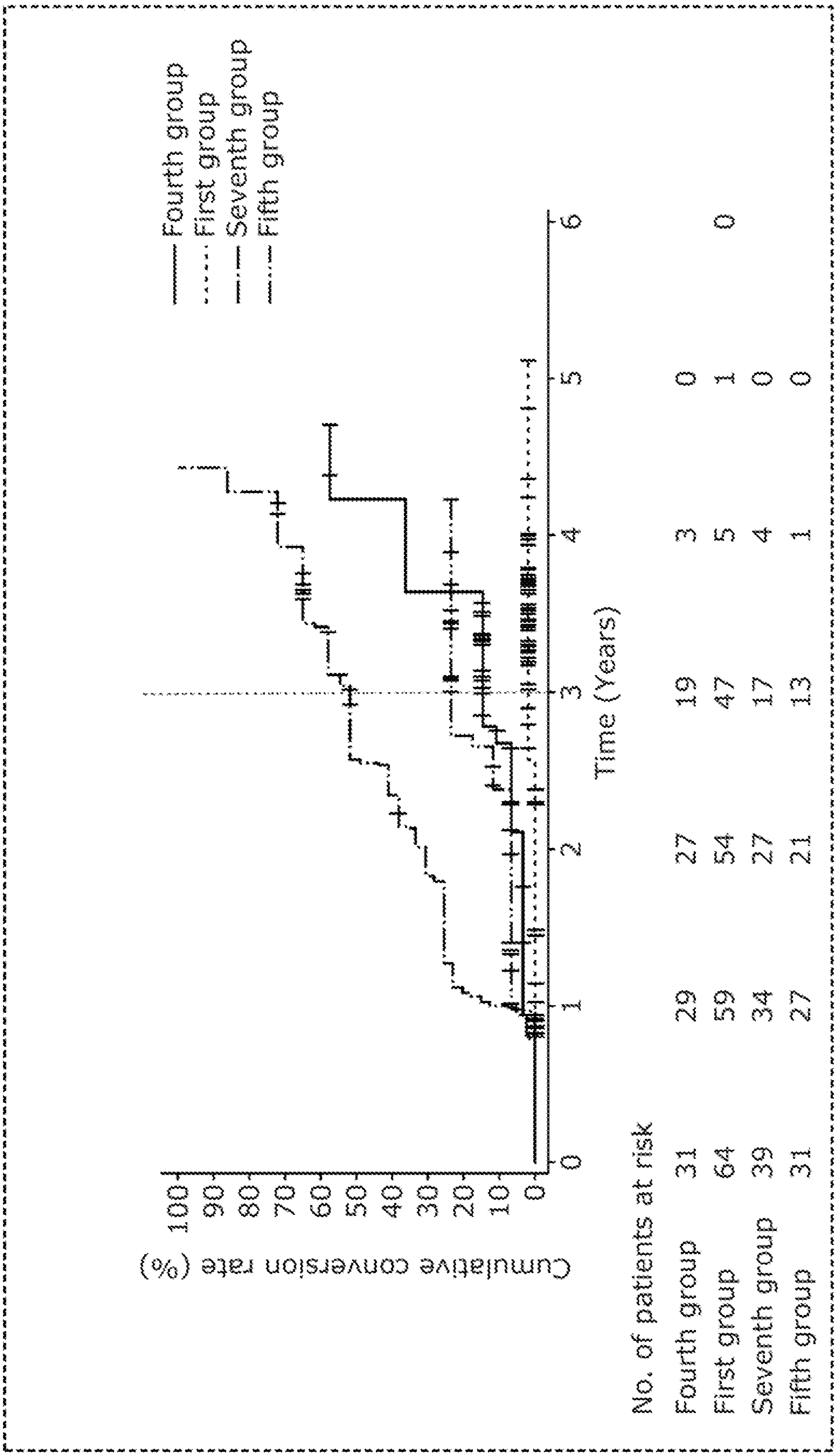
FIG. 15A illustrates Kaplan-Meier curves showing the results of a follow-up study conducted per group by the inventors.
Figure 15B:
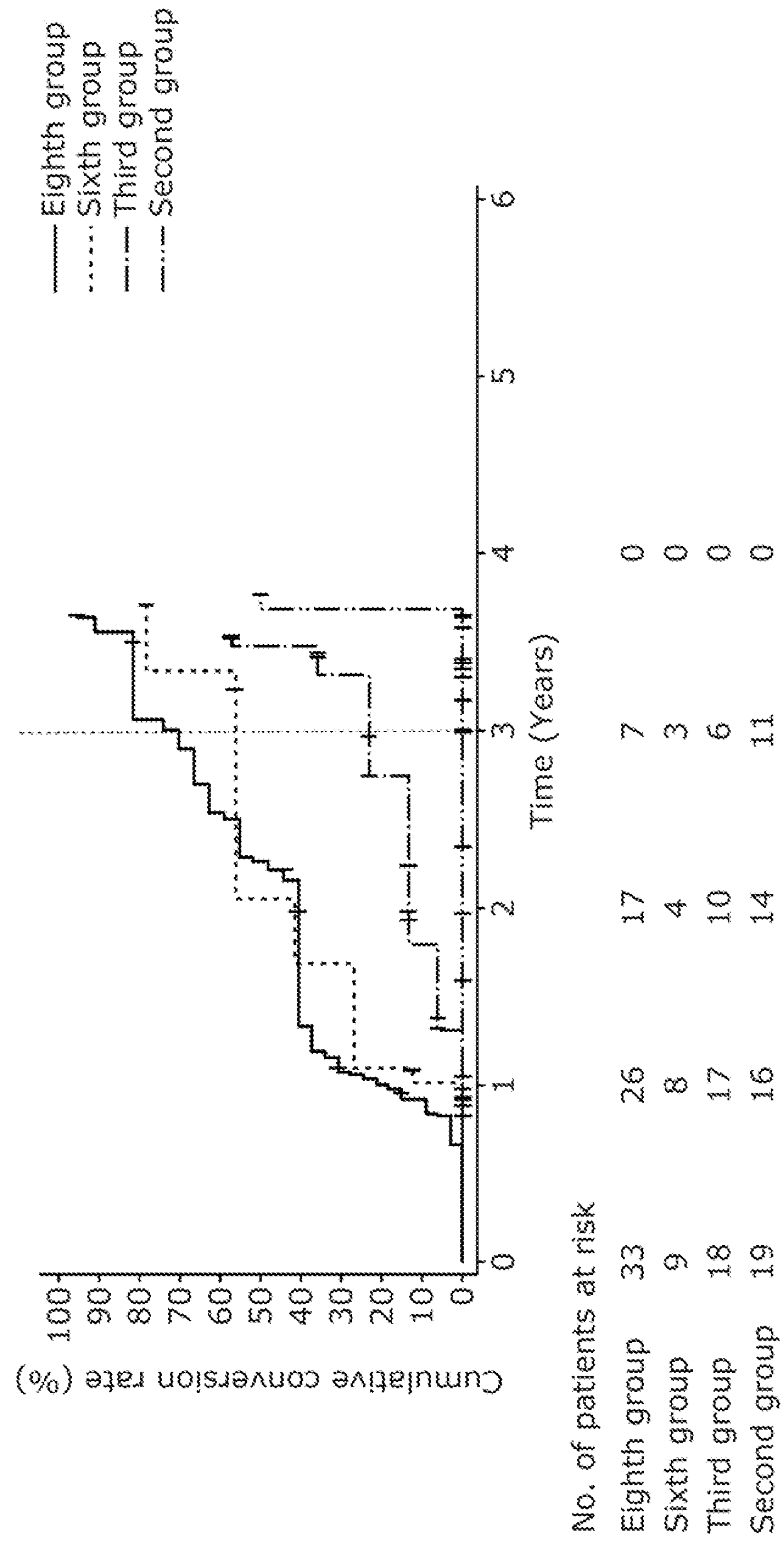
FIG. 15B illustrates Kaplan-Meier curves showing the results of a follow-up study conducted per group by the inventors.

FIG. 15A and FIG. 15B illustrate Kaplan-Meier curves showing the results of a follow-up study conducted per-group by the inventors in a cohort study.

In the Kaplan-Meier curves illustrated in FIG. 15A and FIG. 15B, the horizontal axis is the time [years] elapsed since the start of the follow-up study and the vertical axis is the cumulative conversion rate [%] of subjects who progressed from mild cognitive impairment to Alzheimer's disease.

As can be seen from FIG. 15A and FIG. 15B, the cumulative conversion rate of subjects who progressed from mild cognitive impairment to Alzheimer's disease is less reliable when the time elapsed since the start of the follow-up study exceeds three years because the number of subjects is smaller. For this reason, in the cohort study, discussions are held without using the cumulative conversion rate values for subjects who progressed from mild cognitive impairment to Alzheimer's disease when the time elapsed since the start of the follow-up study exceeded 3 years.

The Kaplan-Meier curves illustrated in FIG. 15A and FIG. 15B indicate that, of the first to eighth groups, the sixth, seventh, and eighth groups are at a relatively high risk of progressing to Alzheimer's disease in the future at the start of the follow-up study, and the first and second groups are at a relatively low risk of progressing to Alzheimer's disease in the future at the start of the follow-up study.

In this way, through a cohort study, the inventors found that by classifying each of the plurality of subjects with mild cognitive impairment into (1) the first group if the Alzheimer's disease assessment scale-cognitive subscale score is less than the fifth threshold, the right hippocampus volume is greater than the sixth threshold, and the ApoE phenotype indicates ApoE negative, (2) the second group if the Alzheimer's disease assessment scale-cognitive subscale score is greater than the fifth threshold, the right hippocampus volume is greater than the sixth threshold, and the ApoE phenotype indicates ApoE positive, and the preclinical Alzheimer's cognitive composite score is greater than the seventh threshold, or if the Alzheimer's disease assessment scale-cognitive subscale score is less than the fifth threshold, the right hippocampus volume is greater than the sixth threshold, the ApoE phenotype indicates ApoE positive, and the preclinical Alzheimer's cognitive composite score is greater than the seventh threshold, (3) the third group if the Alzheimer's disease assessment scale-cognitive subscale score is less than the fifth threshold, the right hippocampus volume is less than the sixth threshold, the ApoE phenotype indicates ApoE positive, and the preclinical Alzheimer's cognitive composite score is greater than the seventh threshold, (4) the fourth group if the Alzheimer's disease assessment scale-cognitive subscale score is less than the fifth threshold, the right hippocampus volume is less than the sixth threshold, and the ApoE phenotype indicates ApoE negative, (5) the fifth group if the Alzheimer's disease assessment scale-cognitive subscale score is greater than the fifth threshold, the right hippocampus volume is greater than the sixth threshold, and the ApoE phenotype indicates ApoE negative, (6) the sixth group if the Alzheimer's disease assessment scale-cognitive subscale score is greater than the fifth threshold, the right hippocampus volume is greater than the sixth threshold, the ApoE phenotype indicates ApoE positive, and the preclinical Alzheimer's cognitive composite score is less than the seventh threshold, or if the Alzheimer's disease assessment scale-cognitive subscale score is less than the fifth threshold, the right hippocampus volume is greater than the sixth threshold, the ApoE phenotype indicates ApoE positive, and the preclinical Alzheimer's cognitive composite score is less than the seventh threshold, (7) the seventh group if the Alzheimer's disease assessment scale-cognitive subscale score is greater than the fifth threshold, and the right hippocampus volume is less than the sixth threshold, and (8) the eighth group if the Alzheimer's disease assessment scale-cognitive subscale score is less than the fifth threshold, the right hippocampus volume is less than the sixth threshold, the ApoE phenotype indicates ApoE positive, and the preclinical Alzheimer's cognitive composite score is less than the seventh threshold, it is possible to classify the plurality of subjects with mild cognitive impairment into a plurality of groups (in this case, eight groups) including sixth, seventh, and eighth groups at a relatively high risk of progressing to Alzheimer's disease in the future and first and second groups at a relatively low risk of progressing to Alzheimer's disease in the future.

The inventors also found through the cohort study that in the above classification, a fifth threshold value of 20.0±1 SD is preferable, a sixth threshold value of 3.651±1 SD [$cm^3$] is preferable, and a seventh threshold of 0.111±1 SD is preferable. Here, the 1 SD of the fifth threshold is 6.3, the 1 SD of the sixth threshold is 0.653 [$cm^3$], and the 1 SD of the seventh threshold is 2.630.

<Operations>

Hereinafter, operations performed by stratification device 10D configured as described above will be described with reference to the drawings.

Figure 16:
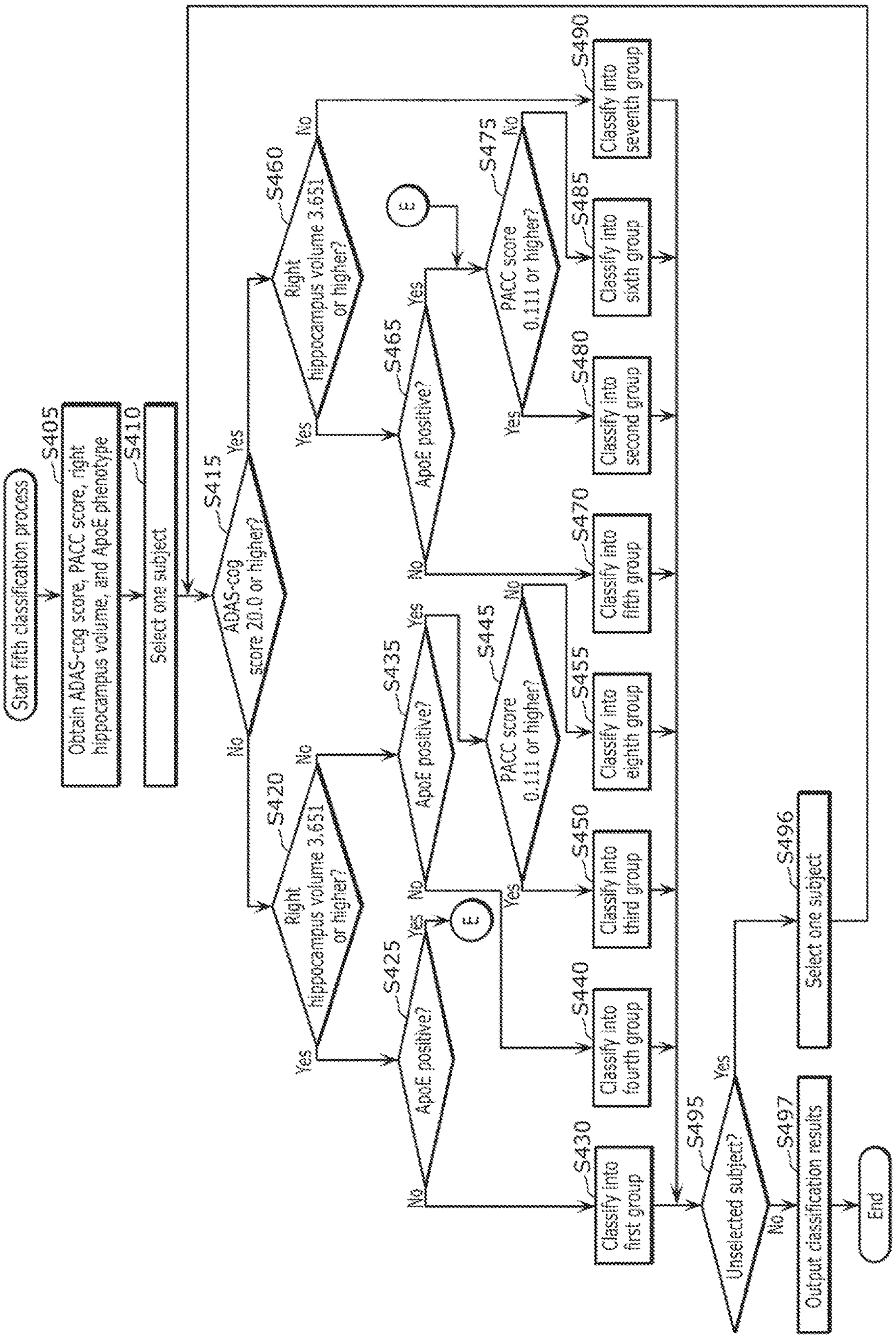
FIG. 16 is a flowchart of the fifth classification process according to Embodiment 5.

FIG. 16 is a flowchart of the fifth classification process performed by stratification device 10D. The fifth classification process classifies the subjects into one of eight groups that include at least the sixth, seventh, and eighth groups at a relatively high risk of progressing to Alzheimer's disease in the future and the first and second groups at a relatively low risk of progressing to Alzheimer's disease in the future, based on the Alzheimer's disease assessment scale-cognitive subscale score, the right hippocampus volume, the ApoE phenotype, and the preclinical Alzheimer's cognitive composite score for each of the plurality of subjects.

The fifth classification process is initiated, for example, when a user of stratification device 10D performs an operation on stratification device 10D to initiate the fifth classification process.

Once the fifth classification process is initiated, obtainment unit 20D obtains, for each of the plurality of subjects with mild cognitive impairment, the score obtained as a result of performing the Alzheimer's disease assessment scale-cognitive subscale (ADAS-cog) test on the subject (ADAS-cog score), the score obtained as a result of performing the preclinical Alzheimer cognitive composite (PACC) test on the subject (PACC score), the right hippocampus volume of the subject, and the ApoE phenotype (step S405).

Once the ADAS-cog scores, the PACC scores, the right hippocampus volumes, and the ApoE phenotypes of the plurality of subjects are obtained, classification unit 30D selects one subject from the plurality of subjects (step S410). Classification unit 30D then checks whether the ADAS-cog score of the selected subject is 20.0 or higher (step S415).

If the ADAS-cog score is not 20.0 or higher in step S415 (step S415: No), classification unit 30D checks whether the right hippocampus volume of the selected subject is 3.651 or higher (step S420).

If the right hippocampus volume is 3.651 or higher in step S420 (step S420: Yes), classification unit 30D checks whether the ApoE phenotype of the selected subject indicates ApoE positive (step S425).

If the ApoE phenotype of the selected subject does not indicate ApoE positive in the process of step S425 (step S425: No), classification unit 30D classifies the selected subject into the first group (step S430).

If the right hippocampus volume is not 3.651 or higher in step S420 (step S420: No), classification unit 30D checks whether the ApoE phenotype of the selected subject indicates ApoE positive (step S435).

If the ApoE phenotype of the selected subject does not indicate ApoE positive in the process of step S435 (step S435: No), classification unit 30D classifies the selected subject into the fourth group (step S440).

If the ApoE phenotype of the selected subject indicates ApoE positive in step S435 (step S435: Yes), classification unit 30D checks whether the PACC score of the selected subject is 0.111 or higher (step S445).

If the PACC score is 0.111 or higher in the process of step S445 (step S445: Yes), classification unit 30D classifies the selected subject into the third group (step S450).

If the PACC score is not 0.111 or higher in the process of step S445 (step S445: No), classification unit 30D classifies the selected subject into the eighth group (step S455).

If the ADAS-cog score is 20.0 or higher in step S415 (step S415: Yes), classification unit 30D checks whether the right hippocampus volume of the selected subject is 3.651 or higher (step S460).

If the right hippocampus volume is 3.651 or higher in step S460 (step S460: Yes), classification unit 30D checks whether the ApoE phenotype of the selected subject indicates ApoE positive (step S465).

If the ApoE phenotype of the selected subject does not indicate ApoE positive in the process of step S465 (step S465: No), classification unit 30D classifies the selected subject into the fifth group (step S470).

When the ApoE phenotype of the selected subject indicates ApoE positive in the process of step S425 (step S425: Yes), and when the ApoE phenotype of the selected subject indicates ApoE positive in the process of step S465 (step S465: Yes), classification unit 30D checks whether the PACC score of the selected subject is 0.111 or higher (step S475).

If the PACC score is 0.111 or higher in the process of step S475 (step S475: Yes), classification unit 30D classifies the selected subject into the second group (step S480).

If the PACC score is not 0.111 or higher in the process of step S475 (step S475: No), classification unit 30D classifies the selected subject into the sixth group (step S485).

If the right hippocampus volume is not 3.651 or higher in the process of step S460 (step S460: No), classification unit 30D classifies the selected subject into the seventh group (step S490).

When the processing of step S430 is completed, when the processing of step S440 is completed, when the processing of step S450 is completed, when the processing of step S455 is completed, when the processing of step S470 is completed, when the processing of step S480 is completed, when the processing of step S485 is completed, and when the processing of step S490 is completed, classification unit 30D checks whether there is an unselected subject among the plurality of subjects (step S495). Here, "unselected subject" means a subject who has not yet been selected in the processing of step S410 and has not yet been selected in the processing of step S496 (to be described later) in the loop process that proceeds from the processing of step S415 through the processing of step S495: Yes, and back to the processing of step S415.

If there is an unselected subject in the process of step S495 (step S495: Yes), classification unit 30D selects one subject from the unselected subjects (step S496).

After the processing of step S496 is completed, processing proceeds to step S415.

If there are no unselected subjects in the process of step S495 (step S495: No), output unit 40 outputs the classification results that classification unit 30D has performed for each of the plurality of subjects (step S497).

After the process of step S497 is completed, stratification device 10D completes its fifth classification process.

<Observations>

Stratification device 10D configured as described above classifies a plurality of subjects with mild cognitive impairment based on their Alzheimer's disease assessment scale-cognitive subscale scores, their right hippocampus volumes, and additionally, their preclinical Alzheimer's cognitive composite scores and whether they are an apolipoprotein Eε4 gene carrier. This allows stratification device 10D to classify the subject with greater accuracy.

Embodiment 6

In order to find a stratification method that would classify, with even higher accuracy, each of a plurality of subjects with mild cognitive impairment into one of a plurality of groups according to their risk of progressing to Alzheimer's disease in the future, the inventors assessed the risk of progressing from mild cognitive impairment to Alzheimer's disease for various factors, specifically for those with positive beta-amyloid brain PET scans. Here, we refer to an individual with a resulting score of a PET scan using AV45 as a tracer of higher than 1.11 as an individual with a positive beta-amyloid brain PET scan.

FIG. 17 is a schematic diagram illustrating one example of the content of a risk assessment conducted by the inventors for various factors, further performed for individuals with a positive beta-amyloid brain PET scan.

The inventors arrived at the stratification method of Embodiment 6 as a result of their study of the contents of the risk assessment illustrated in FIG. 17.

Hereinafter, the stratification device that executes the stratification method according to Embodiment 6 will be described. The stratification device according to Embodiment 6 is equivalent to stratification device 10 according to Embodiment 1 with some changes in the functions. The stratification device according to Embodiment 6 is a device that classifies each of a plurality of subjects with mild cognitive impairment and a positive beta-amyloid brain PET scan into one of a plurality of groups according to the risk of progressing to Alzheimer's disease in the future. The plurality of groups include at least a first group, which is a high-risk group with a relatively high risk of progressing to Alzheimer's disease in the future, and a second group, which is a low-risk group with a relatively low risk of progressing to Alzheimer's disease in the future.

The stratification device according to Embodiment 6 is one example of a device that executes a classification process that reflects findings by the inventors from a cohort study of a plurality of subjects with mild cognitive impairment and a positive beta-amyloid brain PET scan.

The following description of the stratification device according to Embodiment 6 will focus on the differences from stratification device 10, omitting detailed descriptions of the same elements as those in stratification device 10, as they have already been described.

<Configuration>

Figure 18:
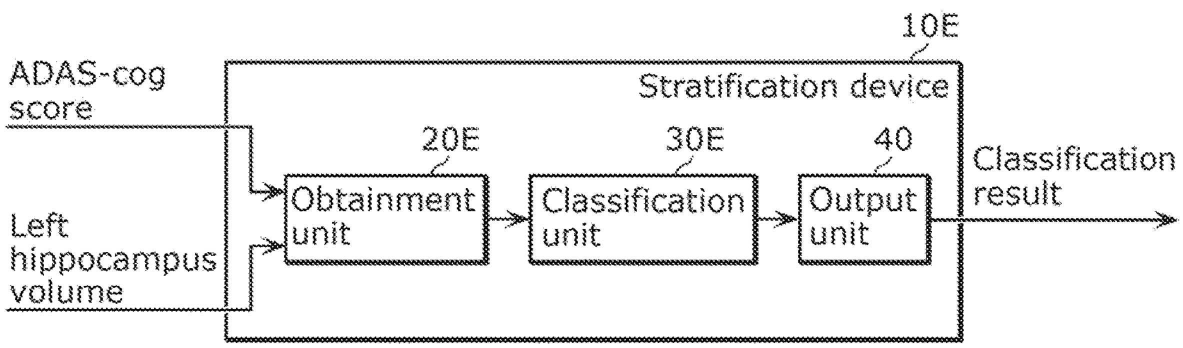
FIG. 18 is a block diagram illustrating one example of the configuration of the stratification method according to Embodiment 6.

FIG. 18 is a block diagram illustrating one example of the configuration of stratification device 10E that executes the stratification method according to Embodiment 6.

As illustrated in FIG. 18, stratification device 10E differs from stratification device 10 according to Embodiment 1 in that obtainment unit 20 has been changed to obtainment unit 20E and classification unit 30 has been changed to classification unit 30E.

For each of a plurality of subjects with mild cognitive impairment and a positive beta-amyloid brain PET scan, obtainment unit 20E obtains a score obtained as a result of performing the Alzheimer's disease assessment scale-cognitive subscale test on the subject and the left hippocampus volume of the subject. Just like the right hippocampus volume, the left hippocampus volume can be measured, for example, by performing an MRI test on the subject and performing image processing on the MRI image of the head obtained as a result of the MRI test.

Classification unit 30E classifies the subjects into one of a plurality of groups including at least a first group at a relatively high risk of progressing to Alzheimer's disease in the future and a second group at a relatively low risk of progressing to Alzheimer's disease in the future, based on the Alzheimer's disease assessment scale-cognitive subscale score and the left hippocampus volume for each of the plurality of subjects. In Embodiment 6, the plurality of groups are exemplified as four groups including a first group, a second group, and further a third group and a fourth group.

Classification unit 30E performs the above classification based on the inventors' findings from a cohort study of a plurality of subjects with mild cognitive impairment and a positive beta-amyloid brain PET scan.

More specifically, classification unit 30E classifies each of the plurality of subjects into (1) the first group if the Alzheimer's disease assessment scale-cognitive subscale score is greater than a first threshold and the left hippocampus volume is less than a second threshold, (2) the second group if the Alzheimer's disease assessment scale-cognitive subscale score is less than the first threshold and the left hippocampus volume is greater than the second threshold, (3) the third group if the Alzheimer's disease assessment scale-cognitive subscale score is greater than the first threshold and the left hippocampus volume is greater than the second threshold, and (4) the fourth group if the Alzheimer's disease assessment scale-cognitive subscale score is less than the first threshold and the left hippocampus volume is less than the second threshold. Here, classification unit 30E performs the above classification with the first threshold set at 14.0 and the second threshold set at 3459 [$mm^3$].

Hereinafter, the findings from a cohort study of a plurality of subjects with mild cognitive impairment and a positive beta-amyloid brain PET scan performed by the inventors will be described.

In the cohort study, the inventors conducted a follow-up study on a plurality of subjects with mild cognitive impairment and a positive beta-amyloid brain PET scan for progression from mild cognitive impairment to Alzheimer's disease.

Figure 19:
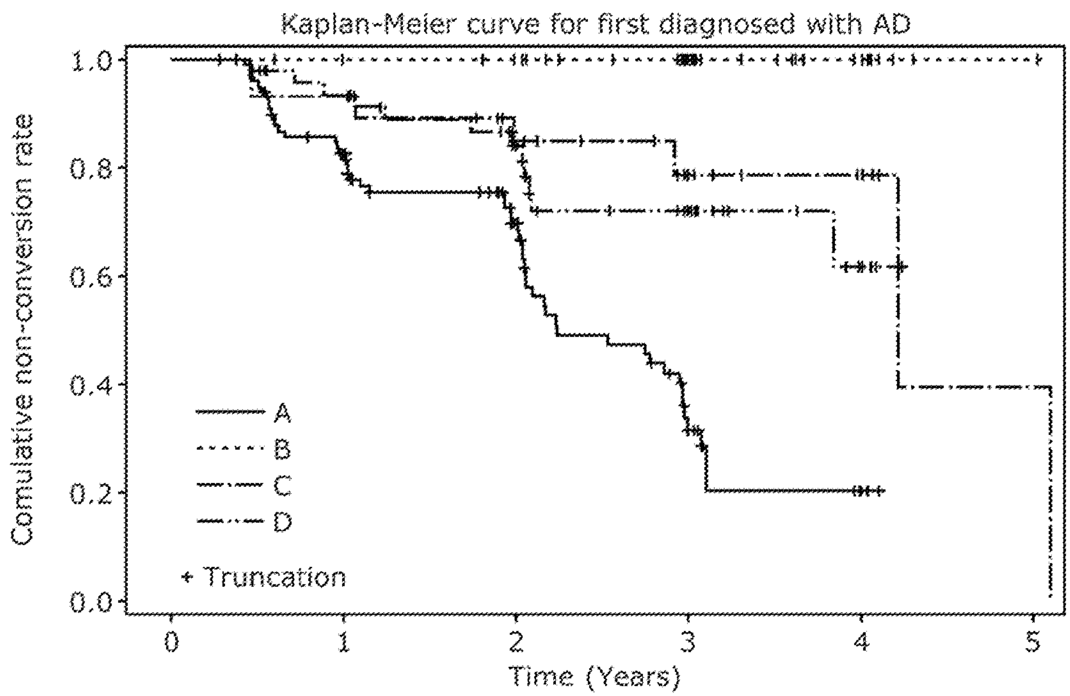
FIG. 19 illustrates one example of survival estimation, using a limit method, showing the results of a follow-up study conducted per group by the inventors.

FIG. 19 illustrates one example of survival estimation, using a product-limit method, showing the results of a follow-up study conducted per group by the inventors in a cohort study.

In the survival estimation according to the product-limit method illustrated in FIG. 19, the horizontal axis is the time [years] elapsed since the start of the follow-up study and the vertical axis is the cumulative ratio of subjects who did not progress from mild cognitive impairment to Alzheimer's disease.

As illustrated in FIG. 19, in the cohort study, the inventors conducted a follow-up study on 220 subjects with mild cognitive impairment and a positive beta-amyloid brain PET scan for approximately five years regarding progression from mild cognitive impairment to Alzheimer's disease. During this approximately five-year period, 70 subjects progressed from mild cognitive impairment to Alzheimer's disease.

In a cohort study, the inventors classified each of the plurality of subjects at the start of the follow-up study into (1) group A (corresponding to the first group) of subjects with an Alzheimer's disease assessment scale-cognitive subscale score greater than a first threshold and a left hippocampus volume less than a second threshold, (2) group β (corresponding to the second group) of subjects with an Alzheimer's disease assessment scale-cognitive subscale score less than the first threshold and a left hippocampus volume greater than the second threshold, (3) group C (corresponding to the third group) of subjects with an Alzheimer's disease assessment scale-cognitive subscale score greater than the first threshold and a left hippocampus volume greater than the second threshold, or (4) group D (corresponding to the fourth group) of subjects with an Alzheimer's disease assessment scale-cognitive subscale score less than the first threshold and a left hippocampus volume less than the second threshold. They then evaluated the survival estimation according to the product-limit method showing the follow-up results per-group after classification.

The survival estimation according to the product-limit method illustrated in FIG. 19 indicates that, of the first to fourth groups, the first group is at a relatively high risk of progressing to Alzheimer's disease in the future at the start of the follow-up study, and the second group is at a relatively low risk of progressing to Alzheimer's disease in the future at the start of the follow-up study.

The inventors also found through the cohort study that in the above classification, a first threshold value of 14.0±1 SD is preferable and a second threshold value of 3459 [$mm^3$]±1 SD is preferable. Here, the 1 SD of the first threshold is 6.9 and the 1 SD of the second threshold is 543.5 [$mm^3$].

It is particularly important to note the inventors found that by setting the first threshold and the second threshold to the above values, the second group can be defined as a group that is not at risk of progressing to Alzheimer's disease in the future.

<Operations>

Hereinafter, operations performed by stratification device 10E configured as described above will be described with reference to the drawings.

Figure 20:
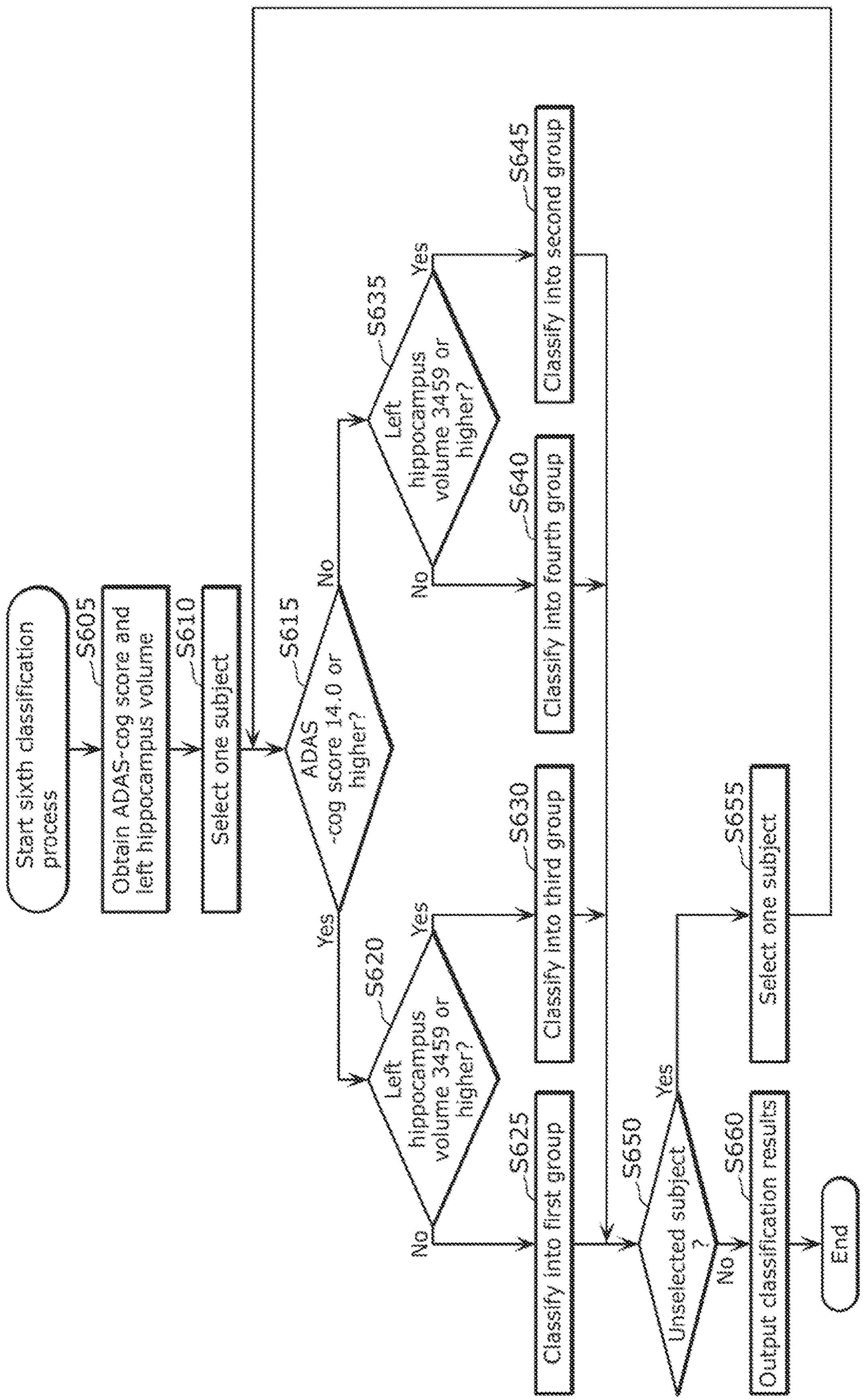
FIG. 20 is a flowchart of the sixth classification process according to Embodiment 6.

FIG. 20 is a flowchart of the sixth classification process performed by stratification device 10E. This sixth classification process classifies the subjects, each with a positive beta-amyloid brain PET scan, into one of four groups that include at least a first group at a relatively high risk of progressing to Alzheimer's disease in the future and a second group at a relatively low risk of progressing to Alzheimer's disease in the future, based on the Alzheimer's disease assessment scale-cognitive subscale score and the left hippocampus volume for each of the plurality of subjects.

The sixth classification process is initiated, for example, when a user of stratification device 10E performs an operation on stratification device 10E to initiate the sixth classification process.

Once the sixth classification process is initiated, obtainment unit 20E obtains, for each of the plurality of subjects with mild cognitive impairment and a positive beta-amyloid brain PET scan, the score obtained as a result of performing the Alzheimer's disease assessment scale-cognitive subscale (ADAS-cog) test on the subject (ADAS-cog score) and the left hippocampus volume of the subject (step S605).

Once the ADAS-cog scores and left hippocampus volumes of the plurality of subjects are obtained, classification unit 30E selects one subject the plurality of subjects (step S610). Classification unit 30E then checks whether the ADAS-cog score of the selected subject is 14.0 or higher (step S615).

If the ADAS-cog score is 14.0 or higher in step S615 (step S615: Yes), classification unit 30E checks whether the left hippocampus volume of the selected subject is 3459 or higher (step S620).

If the left hippocampus volume is not 3459 or higher in the process of step S620 (step S620: No), classification unit 30E classifies the selected subject into the first group (step S625).

If the left hippocampus volume is 3459 or higher in the process of step S620 (step S620: Yes), classification unit 30E classifies the selected subject into the third group (step S630).

If the ADAS-cog score is not 14.0 or higher in step S615 (step S615: No), classification unit 30E checks whether the left hippocampus volume of the selected subject is 3459 or higher (step S635).

If the left hippocampus volume is not 3459 or higher in the process of step S635 (step S635: No), classification unit 30E classifies the selected subject into the fourth group (step S640).

If the left hippocampus volume is 3459 or higher in the process of step S35 (step S635: Yes), classification unit 30E classifies the selected subject into the second group (step S645).

When the processing of step S625 is completed, when the processing of step S630 is completed, when the processing of step S640 is completed, and when the processing of step S645 is completed, classification unit 30E checks whether there is an unselected subject among the plurality of subjects (step S650). Here, "unselected subject" means a subject who has not yet been selected in the processing of step S610 and has not yet been selected in the processing of step S655 (to be described later) in the loop process that proceeds from the processing of step S615 through the processing of step S650: Yes, and back to the processing of step S615.

If there is an unselected subject in the process of step S650 (step S650: Yes), classification unit 30E selects one subject from the unselected subjects (step S655).

After the processing of step S655 is completed, processing proceeds to step S615.

If there are no unselected subjects in the process of step S650 (step S650: No), output unit 40 outputs the classification results that classification unit 30E has performed for each of the plurality of subjects (step S660).

After the process of step S660 is completed, stratification device 10E completes its sixth classification process.

<Observations>

Stratification device 10E configured as described above narrows down a plurality of subjects with mild cognitive impairment to those with a positive beta-amyloid brain PET scan, and classifies the narrowed-down subjects based on their Alzheimer's disease assessment scale-cognitive subscale scores and left hippocampus volumes. This allows stratification device 10E to classify the subject with greater accuracy.

[Variation 1]

The following is a description of the stratification device according to Variation 1, which is realized by changing some of the functions of stratification device 10E according to Embodiment 6. As described in Embodiment 6, stratification device 10E classifies a plurality of subjects with mild cognitive impairment and a positive beta-amyloid brain PET scan based on their Alzheimer's disease assessment scale-cognitive subscale scores and left hippocampus volumes, using a first threshold of 14.0 and a second threshold of 3459 [$mm^3$]. In contrast, the stratification device according to Variation 1 classifies a plurality of subjects with mild cognitive impairment and a positive beta-amyloid brain PET scan based on their Alzheimer's disease assessment scale-cognitive subscale scores and left hippocampus volumes, using a first threshold of 12.0 and a second threshold of 3737 [$mm^3$]. Stated differently, the stratification device according to Variation 1 is equivalent to stratification device 10E with the first threshold changed from 14.0 to 12.0 and the second threshold changed from 3459 [$mm^3$] to 3737 [$mm^3$] in the above classification.

The following description of the stratification device according to Variation 1 will focus on the differences from stratification device 10E, omitting detailed descriptions of the same elements as those in stratification device 10E, as they have already been described.

<Configuration>

Figure 21:
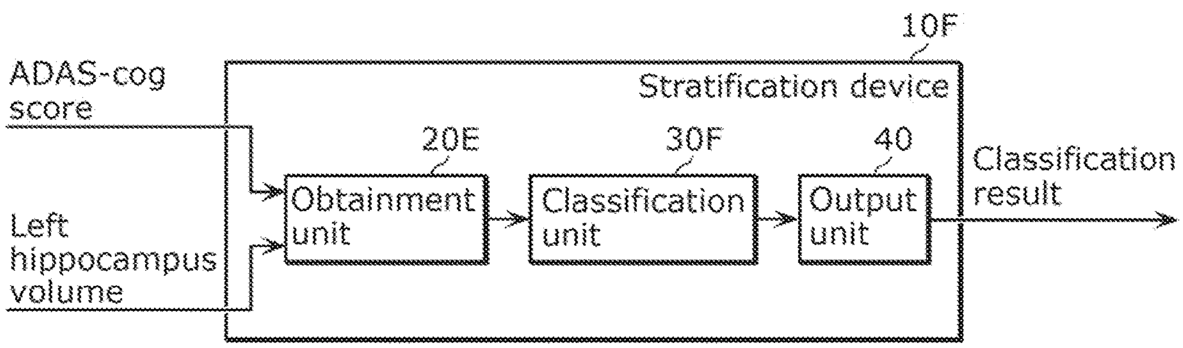
FIG. 21 is a block diagram illustrating one example of the configuration of the stratification method according to Variation 1.

FIG. 21 is a block diagram illustrating one example of the configuration of stratification device 10F that executes the stratification method according to Variation 1.

As illustrated in FIG. 21, stratification device 10F differs from stratification device 10E according to Embodiment 6 in that classification unit 30E has been changed to classification unit 30F. Just like classification unit 30E, classification unit 30F classifies the subjects into one of a plurality of groups including at least a first group at a relatively high risk of progressing to Alzheimer's disease in the future and a second group at a relatively low risk of progressing to Alzheimer's disease in the future, based on the Alzheimer's disease assessment scale-cognitive subscale score and the left hippocampus volume for each of the plurality of subjects. In Variation 1, just like in Embodiment 6, the plurality of groups are exemplified as four groups including a first group, a second group, and further a third group and a fourth group.

Just like classification unit 30E, classification unit 30F performs the above classification based on the inventors' findings from a cohort study of a plurality of subjects with mild cognitive impairment and a positive beta-amyloid brain PET scan.

More specifically, classification unit 30F performs the above classification in the same manner as that performed by classification unit 30E, except that the first threshold is set to 12.0 and the second threshold is set to 3737 [$mm^3$].

Hereinafter, the findings from a cohort study of a plurality of subjects with mild cognitive impairment performed by the inventors will be described.

In the cohort study, the inventors conducted a follow-up study on a plurality of subjects with mild cognitive impairment and a positive beta-amyloid brain PET scan for progression from mild cognitive impairment to Alzheimer's disease.

Figure 22:
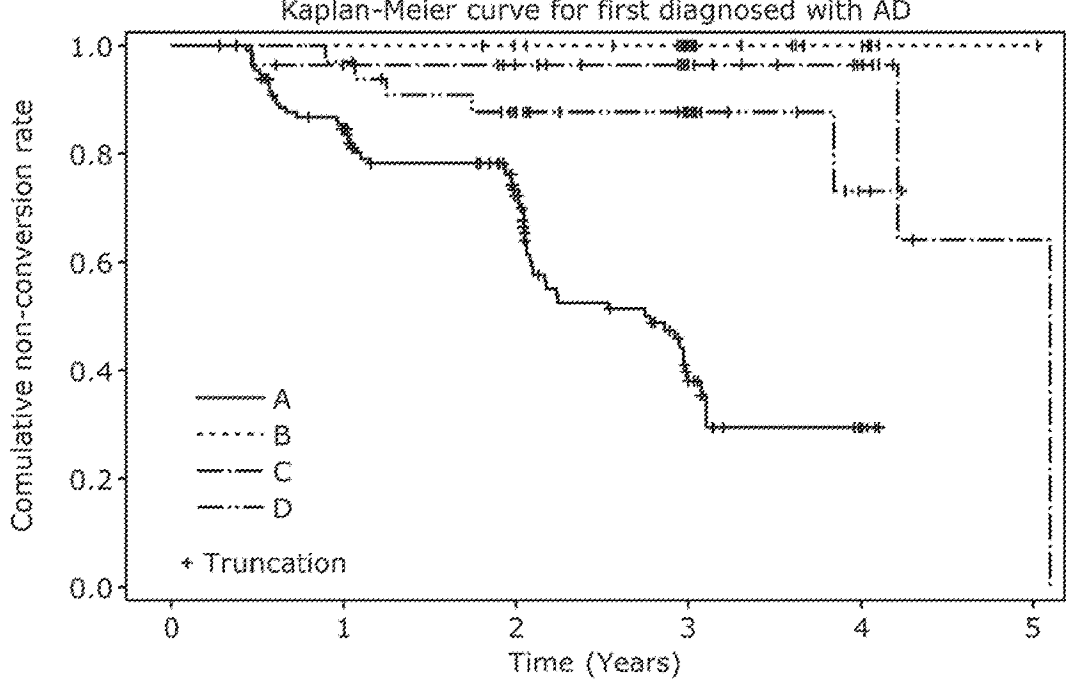
FIG. 22 illustrates one example of survival estimation, using a limit method, showing the results of a follow-up study conducted per group by the inventors.

FIG. 22 illustrates another example of survival estimation, using a product-limit method, showing the results of a follow-up study conducted per group by the inventors in a cohort study.

In the survival estimation according to the product-limit method illustrated in FIG. 22, just as in the survival estimation according to the product-limit method illustrated in FIG. 19, the horizontal axis is the time [years] elapsed since the start of the follow-up study and the vertical axis is the ratio of subjects who did not progress from mild cognitive impairment to Alzheimer's disease.

In a cohort study, the inventors classified each of the plurality of subjects at the start of the follow-up study into (1) group A (corresponding to the first group) of subjects with an Alzheimer's disease assessment scale-cognitive subscale score greater than a first threshold and a left hippocampus volume less than a second threshold, (2) group β (corresponding to the second group) of subjects with an Alzheimer's disease assessment scale-cognitive subscale less than the first threshold and a left hippocampus volume greater than the second threshold, (3) group C (corresponding to the third group) of subjects with an Alzheimer's disease assessment scale-cognitive subscale score greater than the first threshold and a left hippocampus volume greater than the second threshold, or (4) group D (corresponding to the fourth group) of subjects with an Alzheimer's disease assessment scale-cognitive subscale score less than the first threshold and a left hippocampus volume less than the second threshold. They then evaluated the survival estimation according to the product-limit method showing the follow-up results per-group after classification.

The survival estimation according to the product-limit method illustrated in FIG. 22 indicates that, of the first to fourth groups, the first group is at a relatively high risk of progressing to Alzheimer's disease in the future at the start of the follow-up study, and the second group is at a relatively low risk of progressing to Alzheimer's disease in the future at the start of the follow-up study.

The inventors also found through the cohort study that in the above classification, a first threshold value of 12.0 is preferable and a second threshold value of 3737 [$mm^3$] is preferable.

It is particularly important to note the inventors found that by setting the first threshold and the second threshold to the above values, the second group can be defined as a group that is not at risk of progressing to Alzheimer's disease in the future.

<Operations>

Hereinafter, operations performed by stratification device 10E configured as described above will be described with reference to the drawings.

Stratification device 10F performs a seventh classification process instead of the sixth classification process performed by stratification device 10E.

Figure 23:
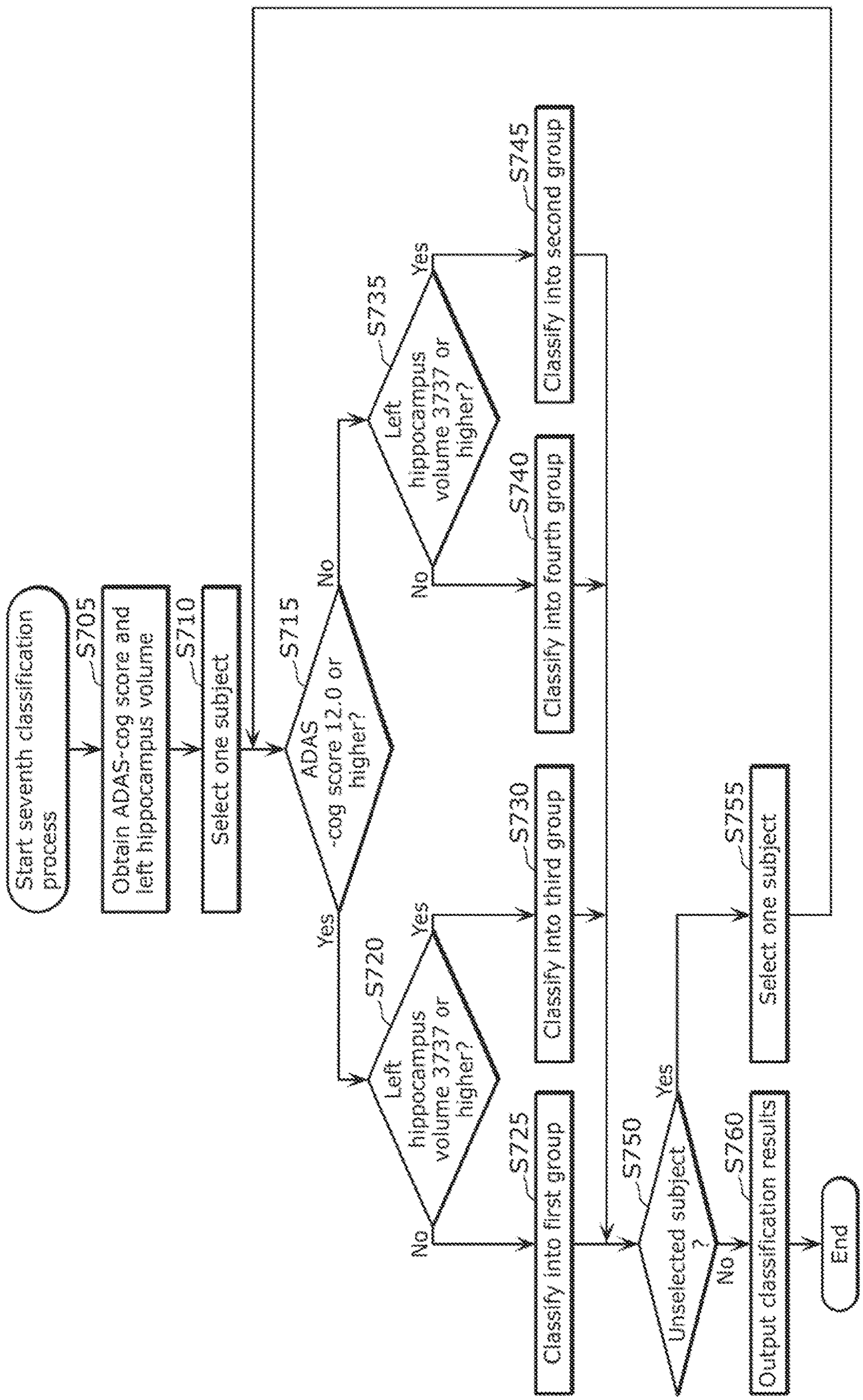
FIG. 23 is a flowchart of the seventh classification process according to Variation 1.

FIG. 23 is a flowchart of the seventh classification process performed by stratification device 10F.

In the seventh classification process, the processing of steps S705 through S710, the processing of steps S725 through S730, and the processing of steps S740 through S760 are respectively equivalent to the processing of steps S605 through S610, steps S625 through S630, and steps S640 through S660 in the sixth classification process according to Embodiment 6, with "classification unit 30E" replaced with "classification unit 30F" and "stratification device 10E" replaced with "stratification device 10F". Accordingly, as these processes have already been described, repeated description here will be omitted, and description will instead focus on the processing of steps S715, S720, and S735.

When the processing of step S710 is completed, classification unit 30F then checks whether the ADAS-cog score of the selected subject is 12.0 or higher (step S715).

If the ADAS-cog score is 12.0 or higher in step S715 (step S715: Yes), classification unit 30F checks whether the left hippocampus volume of the selected subject is 3737 or higher (step S720).

In the process of step S720, if the left hippocampus volume is not 3737 or higher (step S720: No), processing proceeds to step S725.

In the process of step S720, if the left hippocampus volume is 3737 or higher (step S720: Yes), processing proceeds to step S730.

If the ADAS-cog score is not 12.0 or higher in step S715 (step S715: No), classification unit 30F checks whether the left hippocampus volume of the selected subject is 3737 or higher (step S735).

If the left hippocampus volume is not 3737 or higher in the process of step S735 (step S735: No), classification unit 30F classifies the selected subject into the fourth group (step S740).

If the left hippocampus volume is 3737 or higher in the process of step S735 (step S735: Yes), classification unit 30F classifies the selected subject into the second group (step S745).

After the process of step S760 is completed, stratification device 10F completes its seventh classification process.

<Observations>

Just like stratification device 10E, stratification device 10F configured as described narrows down a plurality of subjects with mild cognitive impairment to those with a positive beta-amyloid brain PET scan, and classifies the narrowed-down subjects based on their Alzheimer's disease assessment scale-cognitive subscale scores and left hippocampus volumes. Just like stratification device 10E, this allows stratification device 10F to classify the subject with greater accuracy.

[Variation 2]

The following is a description of the stratification device according to Variation 2, which is realized by changing some of the functions of stratification device 10E according to Embodiment 6. As described in Embodiment 6, stratification device 10E classifies a plurality of subjects with mild cognitive impairment and a positive beta-amyloid brain PET scan based on their Alzheimer's disease assessment scale-cognitive subscale scores and left hippocampus volumes, using a first threshold of 14.0 and a second threshold of 3459 [$mm^3$]. In contrast, the stratification device according to Variation 2 classifies a plurality of subjects with mild cognitive impairment and a positive beta-amyloid brain PET scan based on their Alzheimer's disease assessment scale-cognitive subscale scores and left hippocampus volumes, using a first threshold of 21.0 and a second threshold of 3080 [$mm^3$]. Stated differently, the stratification device according to Variation 2 is equivalent to stratification device 10E with the first threshold changed from 14.0 to 21.0 and the second threshold changed from 3459 [$mm^3$] to 3080 [$mm^3$] in the above classification.

The following description of the stratification device according to Variation 2 will focus on the differences from stratification device 10E, omitting detailed descriptions of the same elements as those in stratification device 10E, as they have already been described.

<Configuration>

Figure 24:
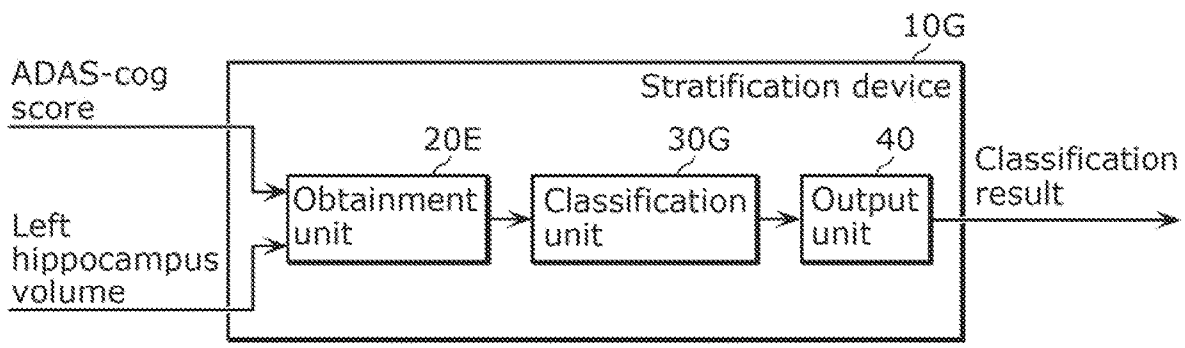
FIG. 24 is a block diagram illustrating one example of the configuration of the stratification method according to Variation 2.

FIG. 24 is a block diagram illustrating one example of the configuration of stratification device 10G that executes the stratification method according to Variation 2.

As illustrated in FIG. 24, stratification device 10G differs from stratification device 10E according to Embodiment 6 in that classification unit 30E has been changed to classification unit 30G.

Just like classification unit 30E, classification unit 30G classifies the subjects into one of a plurality of groups including at least a first group at a relatively high risk of progressing to Alzheimer's disease in the future and a second group at a relatively low risk of progressing to Alzheimer's disease in the future, based on the Alzheimer's disease assessment scale-cognitive subscale score and the left hippocampus volume for each of the plurality of subjects. In Variation 2, just like in Embodiment 6, the plurality of groups are exemplified as four groups including a first group, a second group, and further a third group and a fourth group.

Just like classification unit 30E, classification unit 30G performs the above classification based on the inventors' findings from a cohort study of a plurality of subjects with mild cognitive impairment and a positive beta-amyloid brain PET scan.

More specifically, classification unit 30G performs the above classification in the same manner as that performed by classification unit 30E, except that the first threshold is set to 21.0 and the second threshold is set to 3080 [$mm^3$].

Hereinafter, the findings from a cohort study of a plurality of subjects with mild cognitive impairment performed by the inventors will be described.

In the cohort study, the inventors conducted a follow-up study on a plurality of subjects with mild cognitive impairment and a positive beta-amyloid brain PET scan for progression from mild cognitive impairment to Alzheimer's disease.

Figure 25:
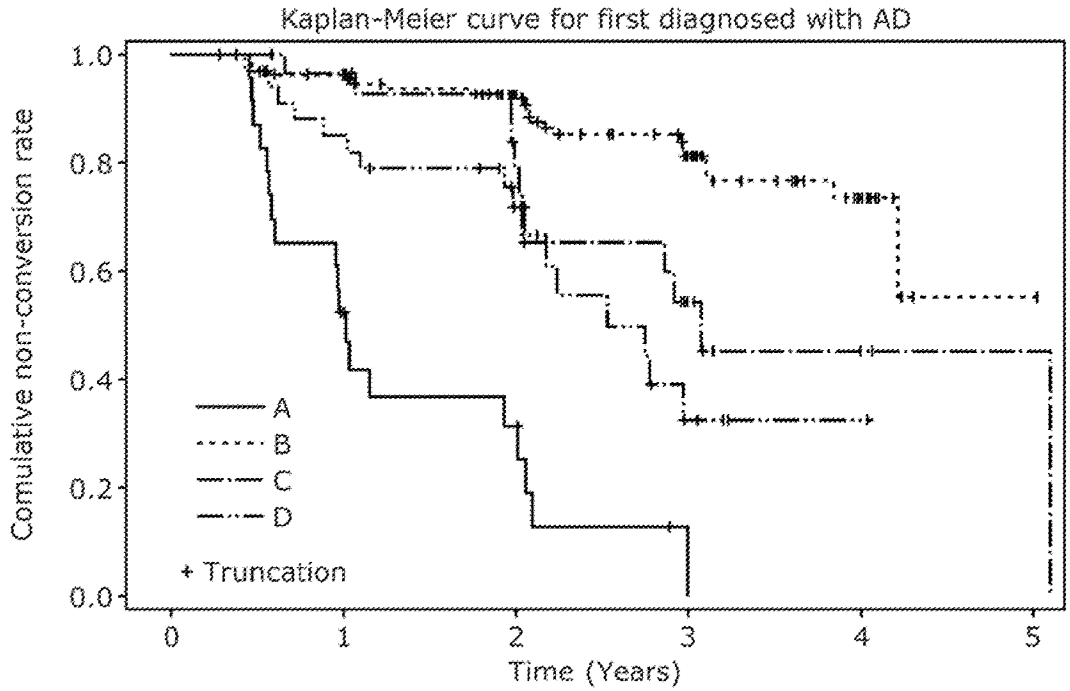
FIG. 25 illustrates one example of survival estimation, using a limit method, showing the results of a follow-up study conducted per group by the inventors.

FIG. 25 illustrates another example of survival estimation, using a product-limit method, showing the results of a follow-up study conducted per group by the inventors in a cohort study.

In the survival estimation according to the product-limit method illustrated in FIG. 25, just as in the survival estimation according to the product-limit method illustrated in FIG. 19, the horizontal axis is the time [years] elapsed since the start of the follow-up study and the vertical axis is the ratio of subjects who did not progress from mild cognitive impairment to Alzheimer's disease.

In a cohort study, the inventors classified each of the plurality of subjects at the start of the follow-up study into (1) group A (corresponding to the first group) of subjects with an Alzheimer's disease assessment scale-cognitive subscale score greater than a first threshold and a left hippocampus volume less than a second threshold, (2) group β (corresponding to the second group) of subjects with an Alzheimer's disease assessment scale-cognitive subscale score less than the first threshold and a left hippocampus volume greater than the second threshold, (3) group C (corresponding to the third group) of subjects with an Alzheimer's disease assessment scale-cognitive subscale score greater than the first threshold and a left hippocampus volume greater than the second threshold, or (4) group D (corresponding to the fourth group) of subjects with an Alzheimer's disease assessment scale-cognitive subscale score less than the first threshold and a left hippocampus volume less than the second threshold. They then evaluated the survival estimation according to the product-limit method showing the follow-up results per-group after classification.

The survival estimation according to the product-limit method illustrated in FIG. 25 indicates that, of the first to fourth groups, the first group is at a relatively high risk of progressing to Alzheimer's disease in the future at the start of the follow-up study, and the second group is at a relatively low risk of progressing to Alzheimer's disease in the future at the start of the follow-up study.

The inventors also found through the cohort study that in the above classification, a first threshold value of 21.0 is preferable and a second threshold value of 3080 [$mm^3$] is preferable.

It is particularly important to note the inventors found that by setting the first threshold and the second threshold to the above values, the first group can be defined as a group that has an extremely high risk of about 80% of progressing to Alzheimer's disease in the future.

<Operations>

Hereinafter, operations performed by stratification device 10G configured as described above will be described with reference to the drawings.

Stratification device 10G performs an eighth classification process instead of the sixth classification process performed by stratification device 10E.

Figure 26:
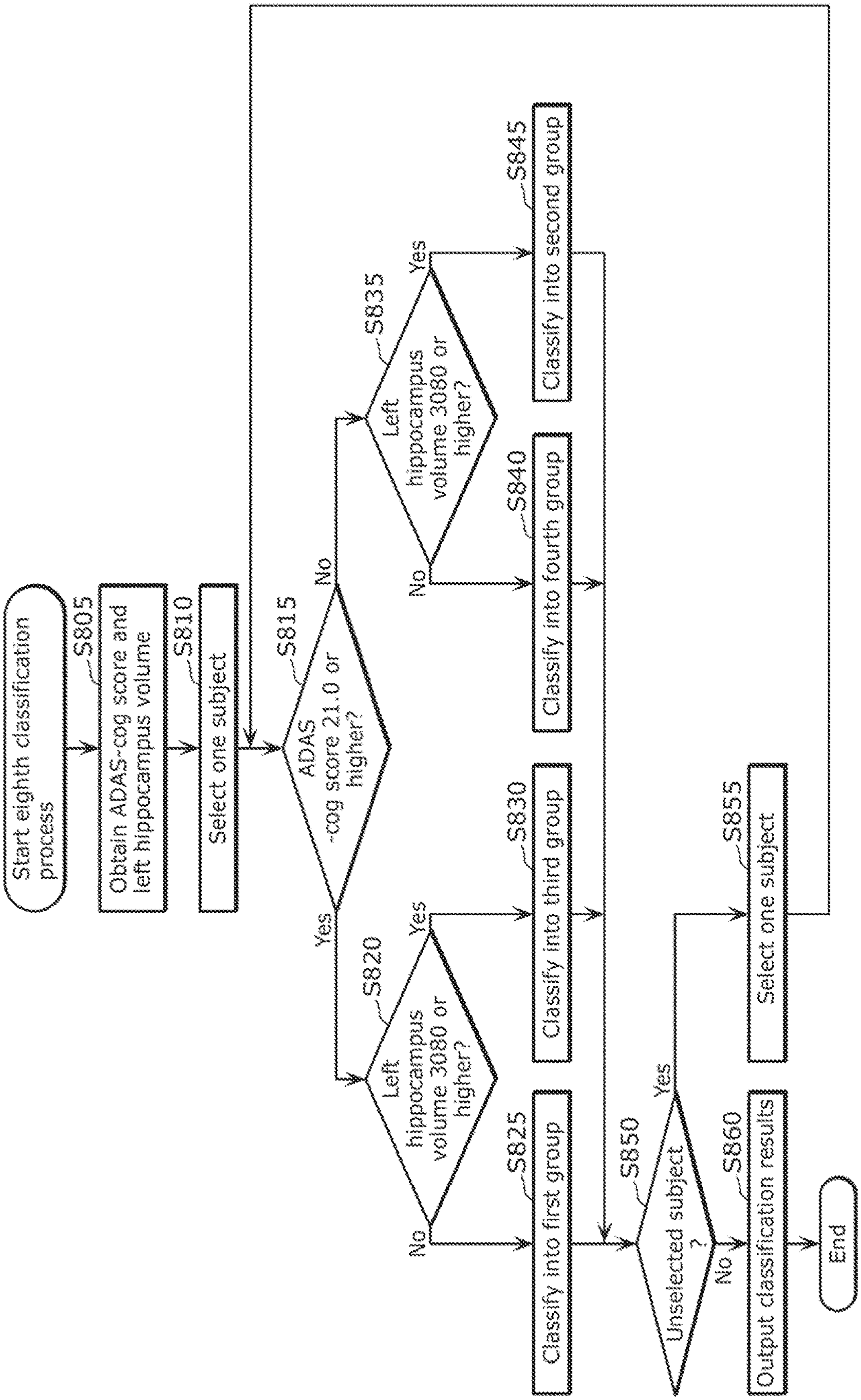
FIG. 26 is a flowchart of the eighth classification process according to Variation 2.

FIG. 26 is a flowchart of the eighth classification process performed by stratification device 10G.

In the eighth classification process, the processing of steps S805 through S810, the processing of steps S825 through S830, and the processing of steps S840 through S860 are respectively equivalent to the processing of steps S605 through S610, steps S625 through S630, and steps S640 through S660 in the sixth classification process according to Embodiment 6, with "classification unit 30E" replaced with "classification unit 30G" and "stratification device 10E" replaced with "stratification device 10G". Accordingly, as these processes have already been described, repeated description here will be omitted, and description will instead focus on the processing of steps S815, S820, and S835.

When the processing of step S810 is completed, classification unit 30G then checks whether the ADAS-cog score of the selected subject is 21.0 or higher (step S815).

If the ADAS-cog score is 21.0 or higher in step S815 (step S815: Yes), classification unit 30G checks whether the left hippocampus volume of the selected subject is 3080 or higher (step S820).

In the process of step S820, if the left hippocampus volume is not 3080 or higher (step S820: No), processing proceeds to step S825.

In the process of step S820, if the left hippocampus volume is 3080 or higher (step S820: Yes), processing proceeds to step S830.

If the ADAS-cog score is not 21.0 or higher in step S815 (step S815: No), classification unit 30G checks whether the left hippocampus volume of the selected subject is 3080 or higher (step S835).

If the left hippocampus volume is not 3080 or higher in the process of step S835 (step S835: No), classification unit 30G classifies the selected subject into the fourth group (step S840).

If the left hippocampus volume is 3080 or higher in the process of step S835 (step S835: Yes), classification unit 30G classifies the selected subject into the second group (step S845).

After the process of step S860 is completed, stratification device 10G completes its eighth classification process.

<Observations>

Just like stratification device 10E, stratification device 10G configured as described above narrows down a plurality of subjects with mild cognitive impairment to those with a positive beta-amyloid brain PET scan, and classifies the narrowed-down subjects based on their Alzheimer's disease assessment scale-cognitive subscale scores and left hippocampus volumes. Just like stratification device 10E, this allows stratification device 10G to classify the subject with greater accuracy.

[Variation 3]

The following is a description of the stratification device according to Variation 3, which is realized by changing some of the functions of stratification device 10E according to Embodiment 6. As described in Embodiment 6, stratification device 10E classifies a plurality of subjects with mild cognitive impairment and a positive beta-amyloid brain PET scan based on their Alzheimer's disease assessment scale-cognitive subscale scores and left hippocampus volumes, using a first threshold of 14.0 and a second threshold of 3459 [$mm^3$]. In contrast, the stratification device according to Variation 3 classifies a plurality of subjects with mild cognitive impairment and a positive beta-amyloid brain PET scan based on their Alzheimer's disease assessment scale-cognitive subscale scores and left hippocampus volumes, using a first threshold of 24.0 and a second threshold of 2751 [$mm^3$]. Stated differently, the stratification device according to Variation 2 is equivalent to stratification device 10E with the first threshold changed from 14.0 to 24.0 and the second threshold changed from 3459 [$mm^3$] to 2751 [$mm^3$] in the above classification.

The following description of the stratification device according to Variation 3 will focus on the differences from stratification device 10E, omitting detailed descriptions of the same elements as those in stratification device 10E, as they have already been described.

<Configuration>

Figure 27:
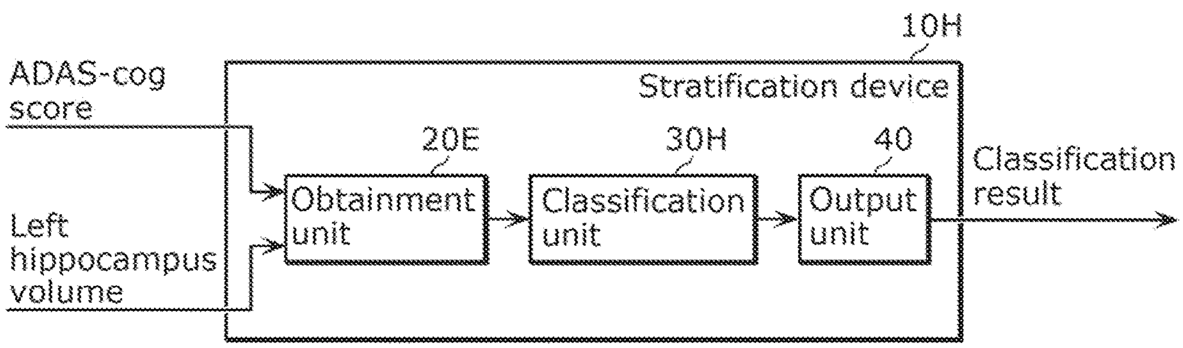
FIG. 27 is a block diagram illustrating one example of the configuration of the stratification method according to Variation 3.

FIG. 27 is a block diagram illustrating one example of the configuration of stratification device 10H that executes the stratification method according to Variation 3.

As illustrated in FIG. 27, stratification device 10H differs from stratification device 10E according to Embodiment 6 in that classification unit 30E has been changed to classification unit 30H. Just like classification unit 30E, classification unit 30H classifies the subjects into one of a plurality of groups including at least a first group at a relatively high risk of progressing to Alzheimer's disease in the future and a second group at a relatively low risk of progressing to Alzheimer's disease in the future, based on the Alzheimer's disease assessment scale-cognitive subscale score and the left hippocampus volume for each of the plurality of subjects. In Variation 2, just like in Embodiment 6, the plurality of groups are exemplified as four groups including a first group, a second group, and further a third group and a fourth group.

Just like classification unit 30E, classification unit 30H performs the above classification based on the inventors' findings from a cohort study of a plurality of subjects with mild cognitive impairment and a positive beta-amyloid brain PET scan.

More specifically, classification unit 30H performs the above classification in the same manner as that performed by classification unit 30E, except that the first threshold is set to 24.0 and the second threshold is set to 2751 [$mm^3$].

Hereinafter, the findings from a cohort study of a plurality of subjects with mild cognitive impairment performed by the inventors will be described.

In the cohort study, the inventors conducted a follow-up study on a plurality of subjects with mild cognitive impairment and a positive beta-amyloid brain PET scan for progression from mild cognitive impairment to Alzheimer's disease.

Figure 28:
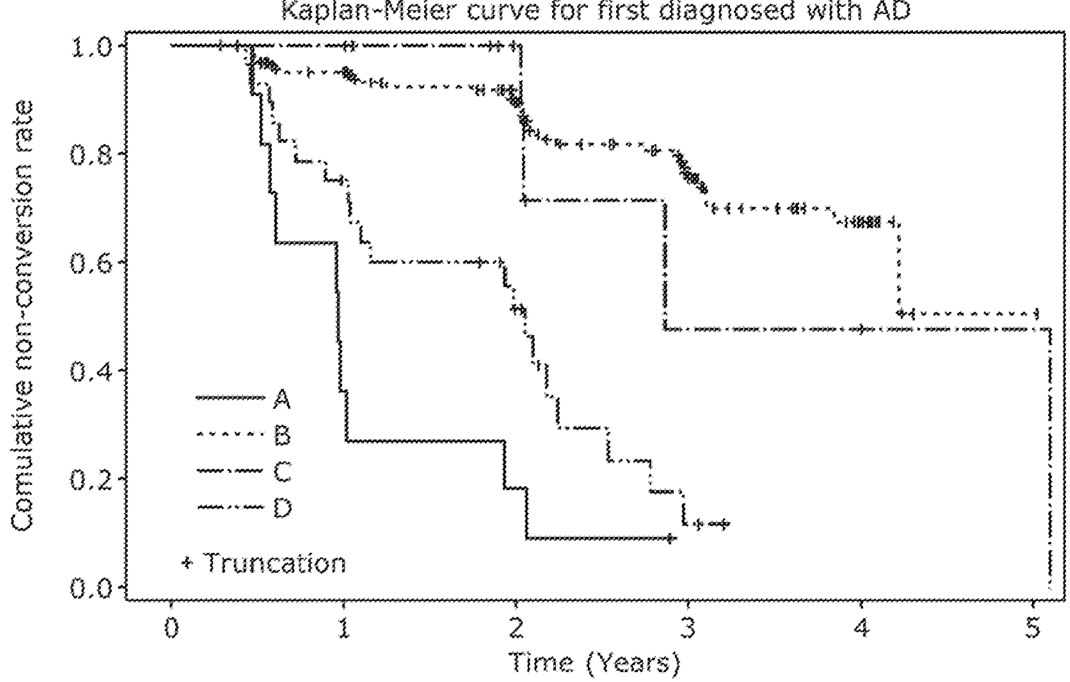
FIG. 28 illustrates one example of survival estimation, using a limit method, showing the results of a follow-up study conducted per group by the inventors.

FIG. 28 illustrates another example of survival estimation, using a product-limit method, showing the results of a follow-up study conducted per group by the inventors in a cohort study.

In the survival estimation according to the product-limit method illustrated in FIG. 28, just as in the survival estimation according to the product-limit method illustrated in FIG. 19, the horizontal axis is the time [years] elapsed since the start of the follow-up study and the vertical axis is the ratio of subjects who did not progress from mild cognitive impairment to Alzheimer's disease.

In a cohort study, the inventors classified each of the plurality of subjects at the start of the follow-up study into (1) group A (corresponding to the first group) of subjects with an Alzheimer's disease assessment scale-cognitive subscale score greater than a first threshold and a hippocampus volume less than a second threshold, (2) group β (corresponding to the second group) of subjects with an Alzheimer's disease assessment scale-cognitive subscale score less than the first threshold and a left hippocampus volume greater than the second threshold, (3) group C (corresponding to the third group) of subjects with an Alzheimer's disease assessment scale-cognitive subscale score greater than the first threshold and a left hippocampus volume greater than the second threshold, or (4) group D (corresponding to the fourth group) of subjects with an Alzheimer's disease assessment scale-cognitive subscale score less than the first threshold and a left hippocampus volume less than the second threshold. They then evaluated the survival estimation according to the product-limit method showing the follow-up results per-group after classification.

The survival estimation according to the product-limit method illustrated in FIG. 28 indicates that, of the first to fourth groups, the first group is at a relatively high risk of progressing to Alzheimer's disease in the future at the start of the follow-up study, and the second group is at a relatively low risk of progressing to Alzheimer's disease in the future at the start of the follow-up study.

The inventors also found through the cohort study that in the above classification, a first threshold value of 24.0 is preferable and a second threshold value of 2751 [$mm^3$] is preferable.

It is particularly important to note the inventors found that by setting the first threshold and the second threshold to the above values, the first group can be defined as a group that has an extremely high risk of about 91% of progressing to Alzheimer's disease in the future.

<Operations>

Hereinafter, operations performed by stratification device 10H configured as described above will be described with reference to the drawings.

Stratification device 10H performs a ninth classification process instead of the sixth classification process performed by stratification device 10E.

Figure 29:
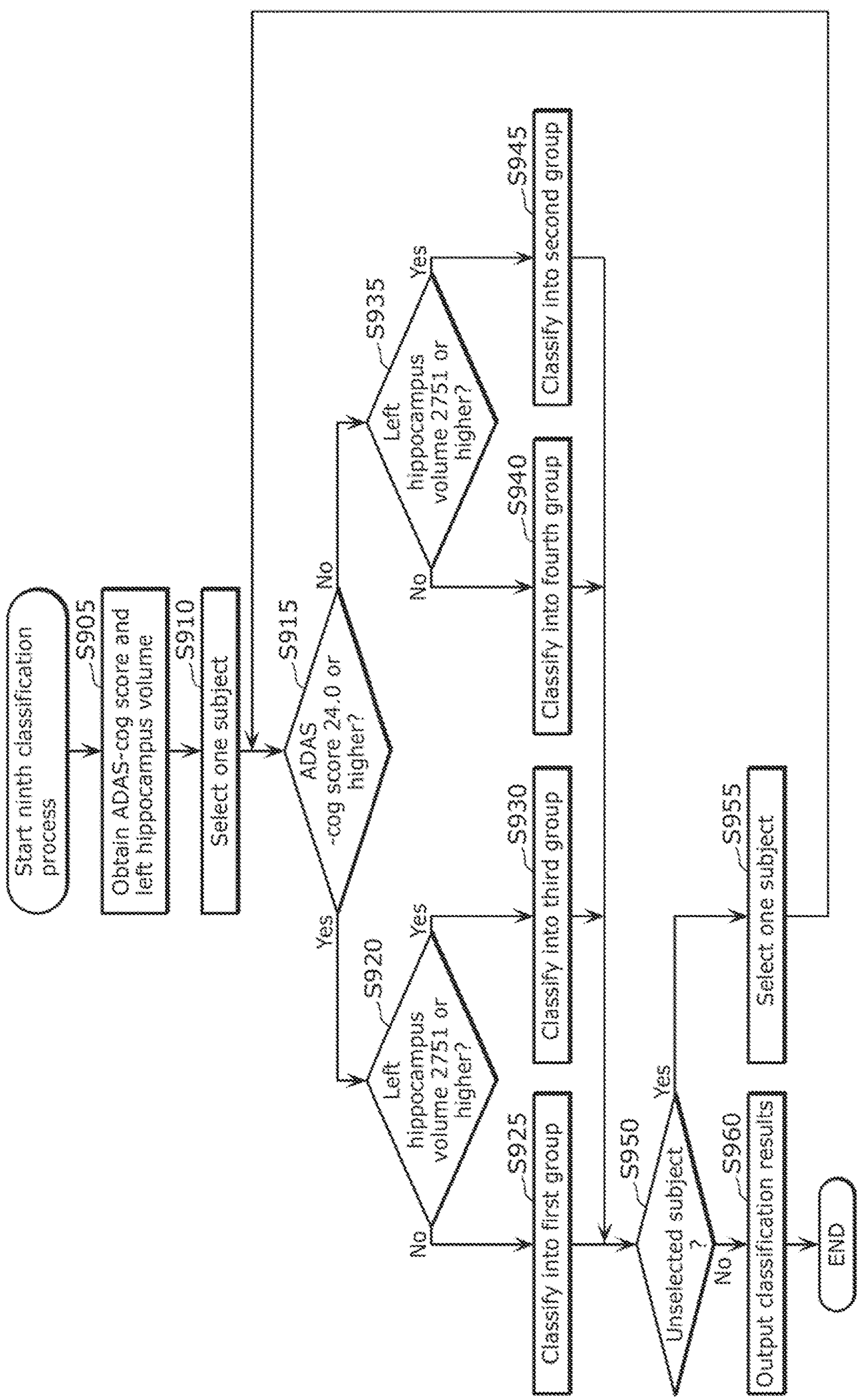
FIG. 29 is a flowchart of the ninth classification process according to Variation 3.

FIG. 29 is a flowchart of the ninth classification process performed by stratification device 10H.

In the ninth classification process, the processing of steps S905 through S910, the processing of steps S925 through S930, and the processing of steps S940 through S960 are respectively equivalent to the processing of steps S605 through S610, steps S625 through S630, and steps S640 through S660 in the sixth classification process according to Embodiment 6, with "classification unit 30E" replaced with "classification unit 30H" and "stratification device 10E" replaced with "stratification device 10H". Accordingly, as these processes have already been described, repeated description here will be omitted, and description will instead focus on the processing of steps S915, S920, and S935.

When the processing of step S910 is completed, classification unit 30H then checks whether the ADAS-cog score of the selected subject is 24.0 or higher (step S915).

If the ADAS-cog score is 24.0 or higher in step S915 (step S915: Yes), classification unit 30H checks whether the left hippocampus volume of the selected subject is 2751 or higher (step S920).

In the process of step S920, if the left hippocampus volume is not 2751 or higher (step S920: No), processing proceeds to step S925.

In the process of step S920, if the left hippocampus volume is 2751 or higher (step S920: Yes), processing proceeds to step S930.

If the ADAS-cog score is not 24.0 or higher in step S915 (step S915: No), classification unit 30H checks whether the left hippocampus volume of the selected subject is 2751 or higher (step S935).

If the left hippocampus volume is not 2751 or higher in the process of step S935 (step S935: No), classification unit 30H classifies the selected subject into the fourth group (step S940).

If the left hippocampus volume is 2751 or higher in the process of step S935 (step S935: Yes), classification unit 30H classifies the selected subject into the second group (step S945).

After the process of step S960 is completed, stratification device 10H completes its ninth classification process.

<Observations>

Just like stratification device 10E, stratification device 10H configured as described above narrows down a plurality of subjects with mild cognitive impairment to those with a positive beta-amyloid brain PET scan, and classifies the narrowed-down subjects based on their Alzheimer's disease assessment scale-cognitive subscale scores and left hippocampus volumes. Just like stratification device 10E, this allows stratification device 10H to classify the subject with greater accuracy.

Embodiment 7

The inventors further examined the risk assessment illustrated in FIG. 17 and found a new variable for classifying each of a plurality of subjects with mild cognitive impairment into one of a plurality of groups according to their risk of progressing to Alzheimer's disease in the future.

Stated differently, the inventors found that the above classification can be performed even more accurately by using the subject's volume score value (Cog_Vol), which indicates the ratio between the subject's left hippocampus volume and subject's ADAS-cog score.

In the following example, the volume score value (Cog_Vol) is the ratio of the left hippocampus volume [$mm^3$] to the ADAS-cog score, i.e., the value obtained by dividing the subject's left hippocampus volume [$mm^3$] by the subject's ADAS-cog score.

In other words, in the following example, the volume score value (Cog_Vol) is specifically calculated using the following formula.

$$\text{Cog\_Vol} = \text{left hippocampus volume } [mm^3]/\text{ADAS-cog score}$$

Hereinafter, the stratification device that executes the stratification method according to Embodiment 7 will be described. The stratification device according to Embodiment 7 is equivalent to stratification device 10E according to Embodiment 6 with some changes in the functions. Just like stratification device 10E, the stratification device according to Embodiment 7 is a device that classifies each of a plurality of subjects with mild cognitive impairment and a positive beta-amyloid brain PET scan into one of a plurality of groups according to the risk of progressing to Alzheimer's disease in the future. The plurality of groups include at least a first group, which is a high-risk group with a relatively high risk of progressing to Alzheimer's disease in the future, and a second group, which is a low-risk group with a relatively low risk of progressing to Alzheimer's disease in the future.

The stratification device according to Embodiment 7 is one example of a device that executes a classification process using the volume score value (Cog_Vol) found by the inventors.

The following description of the stratification device according to Embodiment 7 will focus on the differences from stratification device 10E, omitting detailed descriptions of the same elements as those in stratification device 10E, as they have already been described.

<Configuration>

Figure 30:
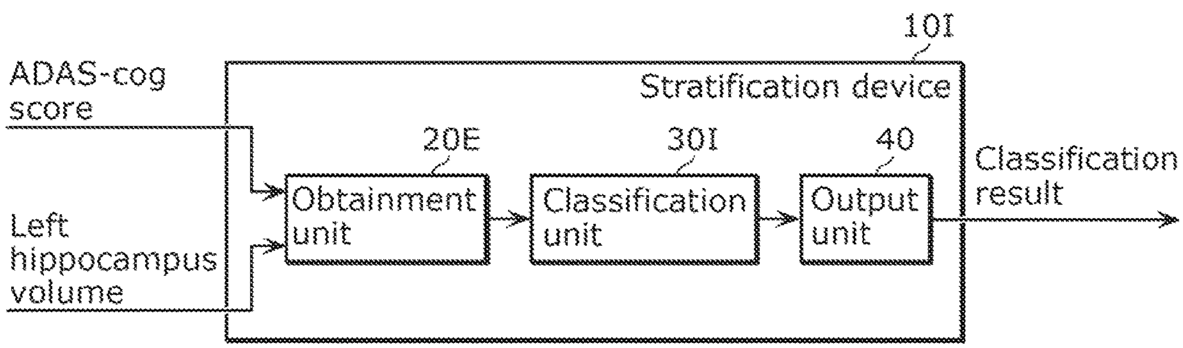
FIG. 30 is a block diagram illustrating one example of the configuration of the stratification method according to Embodiment 7.

FIG. 30 is a block diagram illustrating one example of the configuration of stratification device 10I that executes the stratification method according to Embodiment 7.

As illustrated in FIG. 30, stratification device 10I differs from stratification device 10E according to Embodiment 6 in that classification unit 30E has been changed to classification unit 30I.

Just like classification unit 30E, classification unit 30I classifies the subjects into one of a plurality of groups including at least a first group at a relatively high risk of progressing to Alzheimer's disease in the future and a second group at a relatively low risk of progressing to Alzheimer's disease in the future, based on the Alzheimer's disease assessment scale-cognitive subscale score and the left hippocampus volume for each of the plurality of subjects. In Embodiment 7, the plurality of groups are exemplified as two groups including a first group and a second group.

Classification unit 30I performs the above classification based on the inventors' findings from a cohort study of a plurality of subjects with mild cognitive impairment and a positive beta-amyloid brain PET scan.

More specifically, for each of the plurality of subjects, classification unit 30I performs the above classification based on the volume score value (Cog_Vol) newly found by the inventors through the cohort study. Here, classification unit 30I classifies the subject into the first group when the volume score value (Cog_Vol) is less than 101, and into the second group when the volume score value (Cog_Vol) is not less than 101.

Hereinafter, the volume score value (Cog_Vol) newly found by the inventors through the cohort study will be described.

FIG. 31 is a correspondence table showing the relationship between volume score values (Cog_Vol) and the number of subjects who progressed from mild cognitive impairment to Alzheimer's disease.

Figure 32:
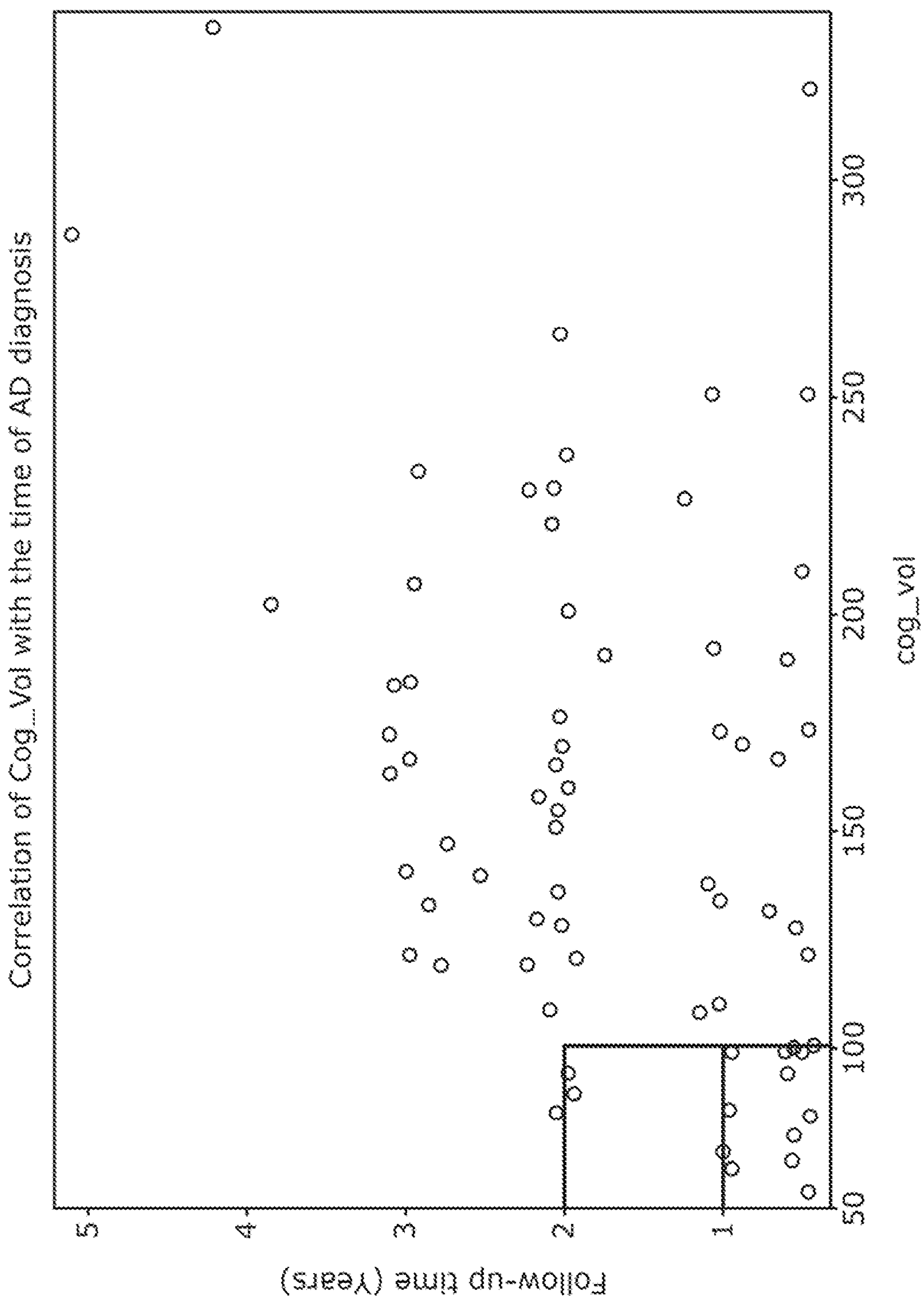
FIG. 32 is a correlation chart showing the relationship between volume score value (Cog_Vol) and the duration it took to progress from mild cognitive impairment to Alzheimer's disease.

FIG. 32 is a correlation chart illustrating the relationship between volume score value (Cog_Vol) and the time from the calculation of the volume score value (Cog_Vol) to progressing to Alzheimer's disease in individuals with a positive beta-amyloid brain PET scan.

In the correlation chart illustrated in FIG. 32, the horizontal axis is the volume score value (Cog_Vol) and the vertical axis is the time [years] from when the volume score value (Cog_Vol) was calculated until progressing to Alzheimer's disease.

As illustrated in FIG. 31 and FIG. 32, 16 of the 17 subjects (i.e., 94.14%) with mild cognitive impairment, a positive beta-amyloid brain PET scan, and a volume score value (Cog_Vol) of less than 101 progressed from the mild cognitive impairment to Alzheimer's disease.

As illustrated in FIG. 32, 13 of the 17 subjects progressed from mild cognitive impairment to Alzheimer's disease within one year.

Thus, the inventors have found a new variable, the volume score value (Cog_Vol), which can classify a plurality of subjects with mild cognitive impairment and a positive beta-amyloid brain PET scan into a group at a very high risk, about 94%, of progressing to Alzheimer's disease in the future.

The inventors found that by setting a plurality of thresholds for the volume score value (Cog_Vol), each of a plurality of subjects with mild cognitive impairment and a positive beta-amyloid brain PET scan can be further narrowly classified into one of a plurality of groups according to the risk of progressing to Alzheimer's disease in the future.

FIG. 33 is a correspondence table showing, for subjects with a positive beta-amyloid brain PET scan among those having mild cognitive impairment, the relationship between the volume score value (Cog_Vol), the plurality of thresholds found by the inventors, and the number of subjects who progressed from mild cognitive impairment to Alzheimer's disease.

Figure 34:
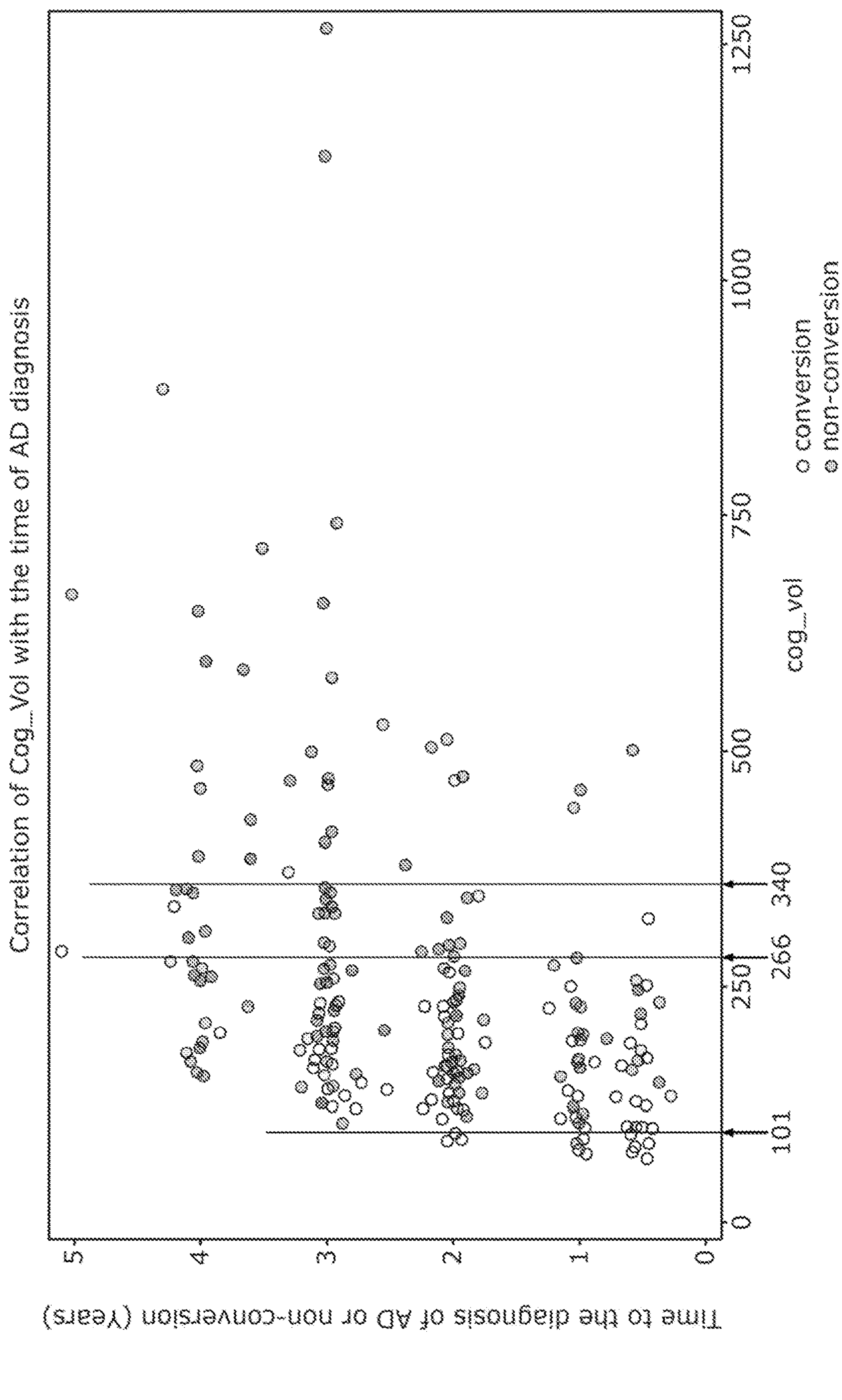
FIG. 34 is a correlation chart showing the relationship between volume score value (Cog_Vol), the duration it took to progress from mild cognitive impairment to Alzheimer's disease or the duration that passed without progressing to Alzheimer's disease.

FIG. 34 is a correlation chart illustrating the relationship between volume score value (Cog_Vol) and the time from the calculation of the volume score value (Cog_Vol) to progressing to Alzheimer's disease, or the time elapsed without progressing to Alzheimer's disease, in individuals with a positive beta-amyloid brain PET scan.

In the correlation chart illustrated in FIG. 34, the horizontal axis is the volume score value (Cog_Vol) and the vertical axis is the time [years] from when the volume score value (Cog_Vol) was calculated until progressing to Alzheimer's disease, or the time [years] that passed without progressing to Alzheimer's disease.

FIG. 35 is a correspondence table showing, for subjects with a positive beta-amyloid brain PET scan among those having mild cognitive impairment, the relationship between the volume score value (Cog_Vol), the plurality of thresholds found by the inventors, and the change in the ratio of subjects who progressed from mild cognitive impairment to Alzheimer's disease.

As illustrated in FIG. 33 to FIG. 35, the inventors found that by classifying each of the subjects with a positive beta-amyloid brain PET scan among those having mild cognitive impairment into (1) the first group if the volume score value (Cog_Vol) is less than the first threshold of 101, (2) the second group if the volume score value (Cog_Vol) is the first threshold of 101 and less than or equal to the second threshold of 142, (3) the third group if the volume score value (Cog_Vol) is greater than the second threshold of 142 and less than or equal to the third threshold of 266, (4) the fourth group if the volume score value (Cog_Vol) is greater than the third threshold of 266 and less than or equal to the fourth threshold of 340, and (5) the fifth group if the volume score value (Cog_Vol) is greater than the fourth threshold of 340, it is possible to classify the first group as a group with a 94.1% rate of progressing to Alzheimer's disease in the future, the second group as a group with a 60.0% rate of progressing to Alzheimer's disease in the future, the third group as a group with a 32.6% rate of progressing to Alzheimer's disease in the future, the fourth group as a group with a 10.4% rate of progressing to Alzheimer's disease in the future, and the fifth group as a group with a 0% rate of progressing to Alzheimer's disease in the future.

In this case, the inventors found that the subjects classified in the first group had an incidence rate of Alzheimer's disease of 70.5% within 1 year, 88.2% within 2 years, and 94.1% within 3 years, subjects classified in the second group had an incidence rate of Alzheimer's disease of 10.0% within 1 year, 26.6% within 2 years, 60.0% within 3 years, and 60.0% within 4 years, subjects classified in the third group had an incidence rate of Alzheimer's disease of 5.9% within 1 year, 13.9% within 2 years, 28.7% within 3 years, and 32.7% within 4 years, and subjects classified in the fourth or fifth group had an incidence rate of Alzheimer's disease of 1.4% within 1 year, 1.4% within 2 years, 1.4% within 3 years, and 4.16% within 4 years.

Thus, the greater the volume score value (Cog_Vol), the lower the incidence rate of Alzheimer's disease.

The inventors found that by setting a plurality of thresholds for the volume score value (Cog_Vol), regardless of whether the subjects had a positive beta-amyloid brain PET scan, each of the plurality of subjects with mild cognitive impairment can be classified into one of a plurality of groups according to the risk of progressing to Alzheimer's disease in the future.

FIG. 36 is a correspondence table showing, for subjects with mild cognitive impairment-regardless of whether they had a positive beta-amyloid brain PET scan—the relationship between the volume score value (Cog_Vol), the plurality of thresholds found by the inventors, and the number of subjects who progressed from mild cognitive impairment to Alzheimer's disease.

Figure 37:
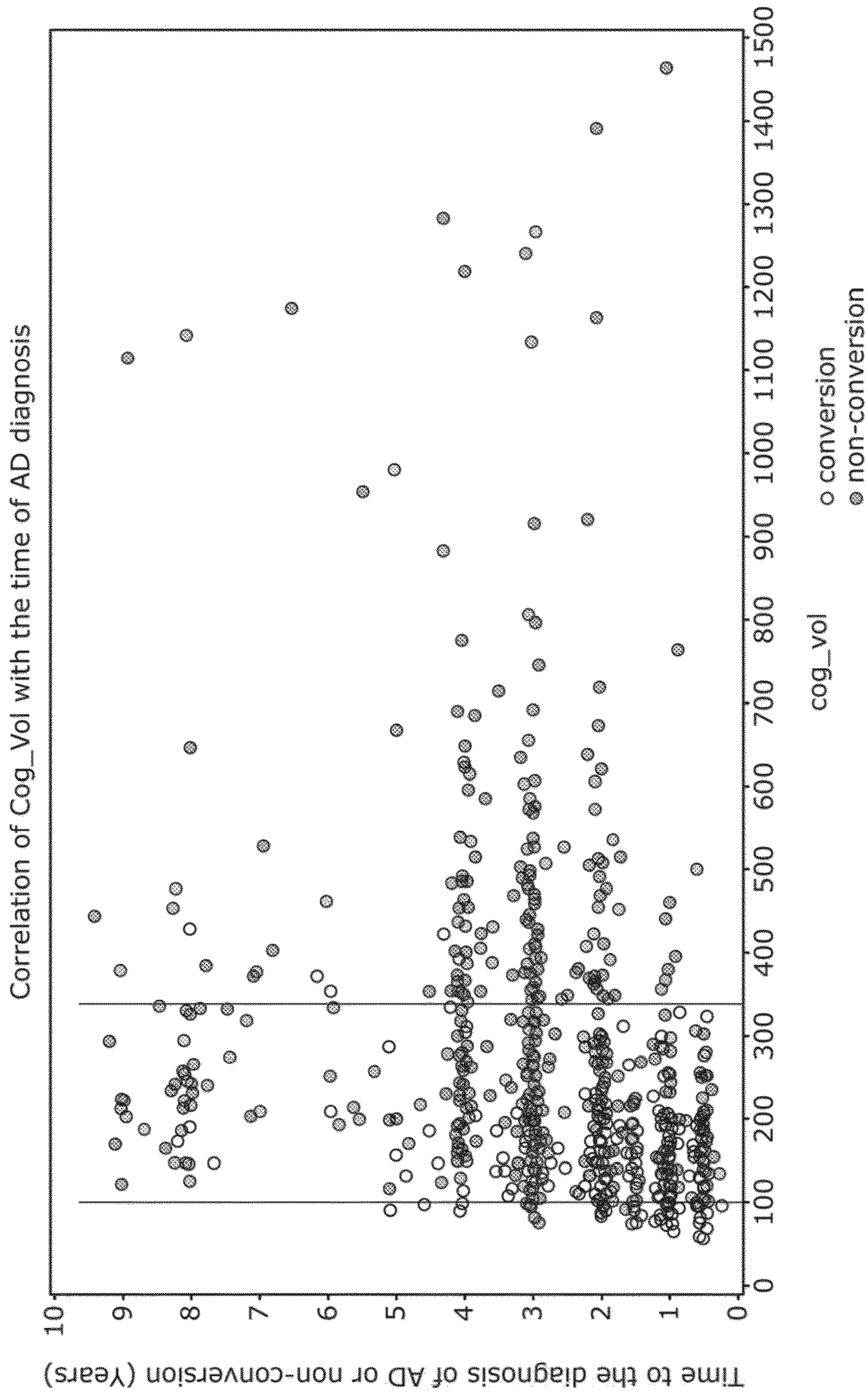
FIG. 37 is a correlation chart showing the relationship between volume score value (Cog_Vol), the duration it took to progress from mild cognitive impairment to Alzheimer's disease or the duration that passed without progressing to Alzheimer's disease.

FIG. 37 is a correlation chart illustrating the relationship between volume score value (Cog_Vol) and the time from the calculation of the volume score value (Cog_Vol) to progressing to Alzheimer's disease, or the time elapsed without progressing to Alzheimer's disease, in individuals regardless of whether they had a positive beta-amyloid brain PET scan.

In the correlation chart illustrated in FIG. 37, the horizontal axis is the volume score value (Cog_Vol) and the vertical axis is the time [years] from when the volume score value (Cog_Vol) was calculated until progressing to Alzheimer's disease, or the time [years] that passed without progressing to Alzheimer's disease.

As illustrated in FIG. 36 and FIG. 37, the inventors found that by classifying each of the subjects with mild cognitive impairment, regardless of whether they have a positive amyloid brain PET scan, into (1) the first group if the volume score value (Cog_Vol) is less than the first threshold of 101, (2) the second group if the volume score value (Cog_Vol) is greater than or equal to the first threshold of 101 and less than or equal to the second threshold of 142, (3) the third group if the volume score value (Cog_Vol) is greater than the second threshold of 142 and less than or equal to the third threshold of 266, (4) the fourth group if the volume score value (Cog_Vol) is greater than the third threshold of 266 and less than or equal to the fourth threshold of 340, and (5) the fifth group if the volume score value (Cog_Vol) is greater than the fourth threshold of 340, it is possible to classify the first group as a group with a 78.1% rate of progressing to Alzheimer's disease in the future, the second group as a group with a 60.3% rate of progressing to Alzheimer's disease in the future, the third group as a group with a 34.6% rate of progressing to Alzheimer's disease in the future, the fourth group as a group with a 10.3% rate of progressing to Alzheimer's disease in the future, and the fifth group as a group with a 3.2% rate of progressing to Alzheimer's disease in the future.

The inventors found that by setting a plurality of thresholds for the volume score value (Cog_Vol) for subjects with mild cognitive impairment and with a positive beta-amyloid brain PET scan, a negative beta-amyloid brain PET scan, or with no information on whether they have a positive or negative beta-amyloid brain PET scan, each of the plurality of subjects can be classified into one of a plurality of groups according to the risk of progressing to Alzheimer's disease in the future.

FIG. 38 is a correspondence table showing, for subjects with mild cognitive impairment and with a positive beta-amyloid brain PET scan, a negative beta-amyloid brain PET scan, or with no information on whether they have a positive or negative beta-amyloid brain PET scan, the relationship between the volume score value (Cog_Vol), the plurality of thresholds found by the inventors, and the change in the ratio of subjects who progressed from mild cognitive impairment to Alzheimer's disease.

As illustrated in FIG. 38, the inventors found that by classifying each of the subjects with mild cognitive impairment and with a positive beta-amyloid brain PET scan, a negative beta-amyloid brain PET scan, or with no information on whether they have a positive or negative beta-amyloid brain PET scan, into (1) the first group if the volume score value (Cog_Vol) is less than the first threshold of 101, (2) the second group if the volume score value (Cog_Vol) is greater than the first threshold of 101 and less than or equal to the second threshold of 142, (3) the third group if the volume score value (Cog_Vol) is greater than the second threshold of 142 and less than or equal to the third threshold of 266, (4) the fourth group if the volume score value (Cog_Vol) is greater than the third threshold of 266 and less than or equal to the fourth threshold of 340, and (5) the fifth group if the volume score value (Cog_Vol) is greater than the fourth threshold of 340, it is possible to classify the first group as a group with a 79.4% rate of progressing to Alzheimer's disease in the future, the second group as a group with a 61.6% rate of progressing to Alzheimer's disease in the future, the third group as a group with a 36.4% rate of progressing to Alzheimer's disease in the future, the fourth group as a group with a 10.8% rate of progressing to Alzheimer's disease in the future, and the fifth group as a group with a 0.6% rate of progressing to Alzheimer's disease in the future.

In this case, the inventors found that the subjects classified in the first group had an incidence rate of Alzheimer's disease of 34.9% within 1 year, 55.5% within 2 years, 60.3% within 3 years, 63.5% within 4 years, 68.3% within 5 years, and 79.4% within 6 years, subjects classified in the second group had an incidence rate of Alzheimer's disease of 15.0% within 1 year, 30.1% within 2 years, 45.9% within 3 years, 53.4% within 4 years, 54.9% within 5 years, and 61.6% within 6 years, subjects classified in the third group had an incidence rate of Alzheimer's disease of 6.4% within 1 year, 16.0% within 2 years, 25.4% within 3 years, 29.3% within 4 years, 31.5% within 5 years, and 36.4% within 6 years, subjects classified in the fourth group had an incidence rate of Alzheimer's disease of 3.2% within 1 year, 5.4% within 2 years, 6.5% within 3 years, 7.6% within 4 years, 8.7% within 5 years, and 10.8% within 6 years, and subjects classified in the fifth group had an incidence rate of Alzheimer's disease of 0% within 1 year, 0% within 2 years, 0.6% within 3 years, 0.6% within 4 years, 1.7% within 5 years, and 3.4% within 6 years.

Thus, the greater the volume score value (Cog_Vol), the lower the incidence rate of Alzheimer's disease.

The inventors conducted a further cohort study of subjects with mild cognitive impairment who were known to have either a positive or negative beta-amyloid brain PET scan result.

As a result, the inventors found that, using a threshold different from the threshold illustrated in FIG. 33, each of the plurality of subjects with mild cognitive impairment and with either a positive or negative beta-amyloid brain PET scan result can be further classified with high accuracy into one of a plurality of groups according to their risk of progressing to Alzheimer's disease in the future.

FIG. 39 is a correspondence table showing, for subjects with mild cognitive impairment who were known to have either a positive or negative beta-amyloid brain PET scan result, the relationship between the volume score value (Cog_Vol_ab), the plurality of thresholds found by the inventors, and the change in the ratio of subjects who progressed from mild cognitive impairment to Alzheimer's disease.

In FIG. 39, the volume score value (Cog_Vol_ab) is calculated in the same manner as the volume score value (Cog_Vol) illustrated in FIG. 33, but as mentioned above, in addition to the two parameters of the volume score value (Cog_Vol) in FIG. 33, a third parameter, whether or not a beta-amyloid brain PET scan result is known, is used to restrict the calculation to subjects with a known beta-amyloid brain PET scan result. Since the volume score value (Cog_Vol_ab) illustrated in FIG. 39 is a value used in classification performed using a threshold different than the threshold illustrated in FIG. 33, it is expressed here as volume score value (Cog_Vol_ab) to distinguish it from the volume score value (Cog_Vol) illustrated in FIG. 33.

As illustrated in FIG. 39, the inventors found that by classifying each of the subjects with mild cognitive impairment who are known to have either a positive or negative beta-amyloid brain PET scan result into (1) the first group if the volume score value (Cog_Vol_ab) is less than the first threshold of 67, (2) the second group if the volume score value (Cog_Vol_ab) is greater than the first threshold of 67 and less than or equal to the second threshold of 135, (3) the third group if the volume score value (Cog_Vol_ab) is greater than the second threshold of 135 and less than or equal to the third threshold of 177, (4) the fourth group if the volume score value (Cog_Vol_ab) is greater than the third threshold of 177 and less than or equal to the fourth threshold of 392, and (5) the fifth group if the volume score value (Cog_Vol_ab) is greater than the fourth threshold of 392, it is possible to classify the first group as a group with 94.1% rate of progressing to Alzheimer's disease in the future, the second group as a group with 43.3% rate of progressing to Alzheimer's disease in the future, the third group as a group with a 27.8% rate of progressing to Alzheimer's disease in the future, the fourth group as a group with 5.1% rate of progressing to Alzheimer's disease in the future, and the fifth group as a group with a 0% rate of progressing to Alzheimer's disease in the future.

In this case, the inventors found that the subjects classified in the first group had an incidence rate of Alzheimer's disease of 64.7% within 1 year, 82.4% within 2 years, 88.2% within 3 years, and 94.1% within 6 years, subjects classified in the second group had an incidence rate of Alzheimer's disease of 11.1% within 1 year, 13.3% within 2 years, 34.4% within 3 years, 38.8% within 4 years, 38.8% within 5 years, and 43.3% within 6 years, subjects classified in the third group had an incidence rate of Alzheimer's disease of 7.4% within 1 year, 13.0% within 2 years, 24.0% within 3 years, 25.9% within 4 years, 25.9% within 5 years, and 27.8% within 6 years, subjects classified in the fourth group had an incidence rate of Alzheimer's disease of 1.3% within 1 year, 2.5% within 2 years, 3.2% within 3 years, 3.2% within 4 years, 3.8% within 5 years, and 5.1% within 6 years, and subjects classified in the fifth group had an incidence rate of Alzheimer's disease of 0% within 6 years.

Thus, the greater the volume score value (Cog_Vol_ab), the lower the incidence rate of Alzheimer's disease.

<Operations>

Hereinafter, operations performed by stratification device 10I configured as described above will be described with reference to the drawings.

Stratification device 10I performs a tenth classification process instead of the sixth classification process performed by stratification device 10E.

Figure 40:
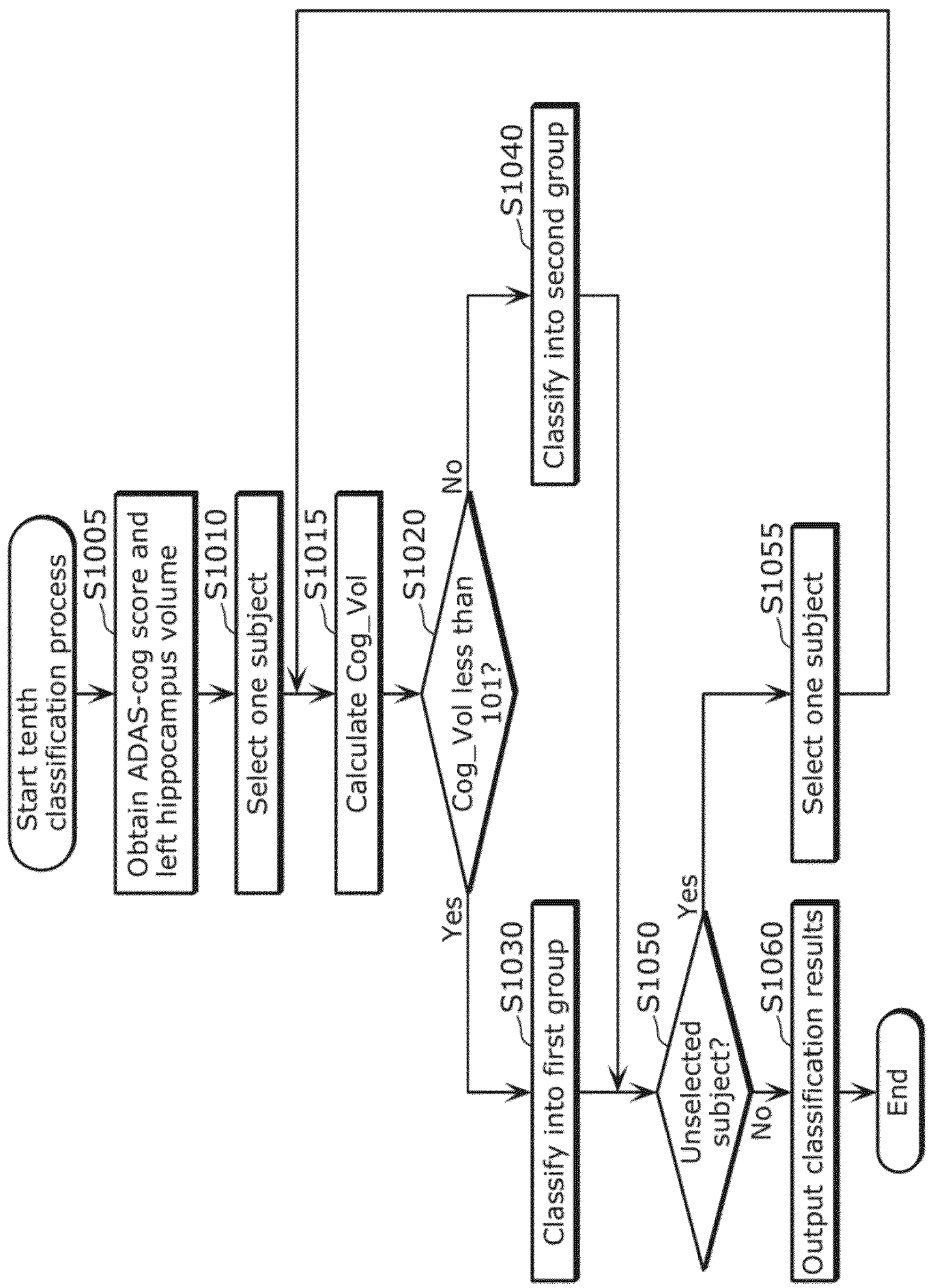
FIG. 40 is a flowchart of the tenth classification process according to Embodiment 7.

FIG. 40 is a flowchart of the tenth classification process performed by stratification device 10I.

In the tenth classification process, the processing of steps S1005 through S1010 and the processing of steps S1050 through S1060 are respectively equivalent to the processing of steps S605 through S610 and the processing of steps S650 through S660 in the sixth classification process according to Embodiment 6, with "classification unit 30E" replaced with "classification unit 30I" and "stratification device 10E" replaced with "stratification device 10I". Accordingly, as these processes have already been described, repeated description here will be omitted, and description will instead focus on the processing of steps S1015 to S1040.

After the process of step S1010 is completed, classification unit 30I calculates the volume score value (Cog_Vol) by dividing the left hippocampus volume of the selected subject by the ADAS-cog score of the selected subject (step S1015).

Classification unit 30I then checks whether the calculated volume score value (Cog_Vol) is less than 101 (step S1020).

If the volume score value (Cog_Vol) is less than 101 or higher in the process of step S1020 (step S1020: Yes), classification unit 30I classifies the selected subject into the first group (step S1030).

If the volume score value (Cog_Vol) is not less than 101 in the process of step S1020 (step S1020: No), classification unit 30I classifies the selected subject into the second group (step S1040).

After the processing of step S1030 is completed, or after the processing of step S1040 is completed, processing proceeds to step S1050.

After the process of step S1060 is completed, stratification device 10I completes its tenth classification process.

<Observations>

Just like stratification device 10E, stratification device 10I configured as described above narrows down a plurality of subjects with mild cognitive impairment to those with a positive beta-amyloid brain PET scan, and classifies the narrowed-down subjects based on their Alzheimer's disease assessment scale-cognitive subscale scores and left hippocampus volumes. Just like stratification device 10E, this allows stratification device 10I to classify the subject with greater accuracy.

(Additional Comments)

The above description is based on Embodiment 1 through Embodiment 7 and Variations 1 through 3 presented as examples of the techniques disclosed in the present application. However, present invention is not limited to these embodiments and variations. Various modifications of the exemplary embodiments as well as embodiments resulting from arbitrary combinations of elements of different exemplary embodiments that may be conceived by those skilled in the art are intended to be included within the scope of one or more aspects of the present invention as long as they do not depart from the essence of the present invention.

In one aspect, the present invention may be realized as a stratification method including, in addition to stratification device 10 through stratification device 10I themselves, the characteristic elements included in stratification device 10 through stratification device 10I, implemented as steps. In one aspect, the present invention may be realized as a computer program that causes a computer to execute each of the characteristic steps included in the stratification method. In one aspect, the present invention may be realized as a non-transitory computer-readable recording medium on which such a computer program is recorded.

The stratification method according to one aspect of the present invention is useful in Alzheimer's disease prevention development.

INDUSTRIAL APPLICABILITY

The present invention can be widely used in stratification methods and the like that classify each of a plurality of subjects with mild cognitive impairment into one of a plurality of groups according to the risk of progressing to Alzheimer's disease in the future.

The invention claimed is:

1. A stratification method comprising:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, wherein the hippocampus volume of each of the plurality of subjects is a right hippocampus volume of each of the plurality of subjects, the clinical psychological test is an Alzheimer's disease assessment scale-cognitive subscale test, in the classifying, for each of the plurality of subjects, the subject is classified into the first group if the score of the subject is greater than a first threshold and the right hippocampus volume of the subject is less than a second threshold, and classified into the second group if the score of the subject is less than the first threshold and the right hippocampus volume of the subject is greater than the second threshold, the first threshold is 20.0±1 SD, the second threshold is 3.651±1 SD [$cm^3$], the 1 SD of the first threshold is 6.3, and the 1 SD of the second threshold is 0.653 [$cm^3$].

2. The stratification method according to claim 1, wherein the obtaining includes further obtaining, for each of the plurality of subjects, information indicating whether the subject is an apolipoprotein Eε4 gene carrier, and in the classifying, each of the plurality of subjects is classified into one of the plurality of groups further based on the information.

3. A stratification method comprising:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, wherein the hippocampus volume of each of the plurality of subjects is a right hippocampus volume of each of the plurality of subjects, the clinical psychological test is a preclinical Alzheimer's cognitive composite test, in the classifying, for each of the plurality of subjects, the subject is classified into the first group if the score of the subject is less than a first threshold and the right hippocampus volume of the subject is less than a second threshold, and classified into the second group if the score of the subject is greater than the first threshold and the right hippocampus volume of the subject is greater than the second threshold, the first threshold is 0.111±1 SD, the second threshold is 3.651±1 SD [$cm^3$], the 1 SD of the first threshold is 2.630, and the 1 SD of the second threshold is 0.653 [$cm^3$].

4. The stratification method according to claim 3, wherein the obtaining includes further obtaining, for each of the plurality of subjects, information indicating whether the subject is an apolipoprotein Eε4 gene carrier, and in the classifying, each of the plurality of subjects is classified into one of the plurality of groups further based on the information.

5. A stratification method comprising:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, wherein the hippocampus volume of each of the plurality of subjects is a right hippocampus volume of each of the plurality of subjects, the clinical psychological test includes an Alzheimer's disease assessment scale-cognitive subscale test and a preclinical Alzheimer's cognitive composite test, the obtaining includes further obtaining, for each of the plurality of subjects, information indicating whether the subject is an apolipoprotein Eε4 gene carrier, in the classifying, for each of the plurality of subjects, the subject is classified into the first group in any of the following cases:

(1) if a first score obtained as a result of the Alzheimer's disease assessment scale-cognitive subscale test performed on the subject is less than a first threshold, the right hippocampus volume of the subject is greater than a second threshold, the information indicates the subject is an apolipoprotein Eε4 gene carrier, and a second score obtained as a result of the preclinical Alzheimer's cognitive composite test performed on the subject is less than a third threshold, the first score being the score;

(2) if the first score of the subject is greater than the first threshold, the right hippocampus volume of the subject is greater than the second threshold, the information indicates the subject is an apolipoprotein Eε4 gene carrier, and the second score of the subject is less than the third threshold;

(3) if the first score of the subject is greater than the first threshold and the right hippocampus volume of the subject is less than the second threshold; or (4) if the first score of the subject is less than the first threshold, the right hippocampus volume of the subject is less than the second threshold, the information indicates the subject is an apolipoprotein Eε4 gene carrier, and the second score of the subject is less than the third threshold, and classified into the second group in any of the following cases:

(5) if the first score of the subject is less than the first threshold, the right hippocampus volume of the subject is greater than the second threshold, the information indicates the subject is an apolipoprotein Eε4 gene carrier, and the second score of the subject is greater than the third threshold;

(6) if the first score of the subject is greater than the first threshold, the right hippocampus volume of the subject is greater than the second threshold, the information indicates the subject is an apolipoprotein Eε4 gene carrier, and the second score of the subject is greater than the third threshold; or (7) if the first score of the subject is less than the first threshold, the right hippocampus volume of the subject is greater than the second threshold, and the information indicates the subject is not an apolipoprotein Eε4 gene carrier, the first threshold is 20.0±1 SD, the second threshold is 3.651±1 SD [$cm^3$], the third threshold is 0.111±1 SD, the 1 SD of the first threshold is 6.3, the 1 SD of the second threshold is 0.653 [$cm^3$], and the 1 SD of the third threshold is 2.630.

6. A stratification method comprising:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, wherein each of the plurality of subjects has a positive beta-amyloid brain PET scan, the hippocampus volume of each of the plurality of subjects is a left hippocampus volume of each of the plurality of subjects, the clinical psychological test is an Alzheimer's disease assessment scale-cognitive subscale test, in the classifying, for each of the plurality of subjects, the subject is classified into the first group if the score of the subject is greater than a first threshold and the left hippocampus volume of the subject is less than a second threshold, and classified into the second group if the score of the subject is less than the first threshold and the left hippocampus volume of the subject is greater than the second threshold, the first threshold is 14.0±1 SD, the second threshold is 3.459±1 SD [$cm^3$], the 1 SD of the first threshold is 6.9, and the 1 SD of the second threshold is 0.5435 [$cm^3$].

7. A stratification method comprising:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, wherein each of the plurality of subjects has a positive beta-amyloid brain PET scan, the hippocampus volume of each of the plurality of subjects is a left hippocampus volume of each of the plurality of subjects, the clinical psychological test is an Alzheimer's disease assessment scale-cognitive subscale test, in the classifying, for each of the plurality of subjects, the subject is classified into the first group if the score of the subject is greater than a first threshold and the left hippocampus volume of the subject is less than a second threshold, and classified into the second group if the score of the subject is less than the first threshold and the left hippocampus volume of the subject is greater than the second threshold, the first threshold is 12.0, and the second threshold is 3.737 [$cm^3$].

8. A stratification method comprising:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, wherein each of the plurality of subjects has a positive beta-amyloid brain PET scan, the hippocampus volume of each of the plurality of subjects is a left hippocampus volume of each of the plurality of subjects, the clinical psychological test is an Alzheimer's disease assessment scale-cognitive subscale test, in the classifying, for each of the plurality of subjects, the subject is classified into the first group if the score of the subject is greater than a first threshold and the left hippocampus volume of the subject is less than a second threshold, and classified into the second group if the score of the subject is less than the first threshold and the left hippocampus volume of the subject is greater than the second threshold, the first threshold is 21.0, and the second threshold is 3.080 [$cm^3$].

9. A stratification method comprising:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, wherein each of the plurality of subjects has a positive beta-amyloid brain PET scan, the hippocampus volume of each of the plurality of subjects is a left hippocampus volume of each of the plurality of subjects, the clinical psychological test is an Alzheimer's disease assessment scale-cognitive subscale test, in the classifying, for each of the plurality of subjects, the subject is classified into the first group if the score of the subject is greater than a first threshold and the left hippocampus volume of the subject is less than a second threshold, and classified into the second group if the score of the subject is less than the first threshold and the left hippocampus volume of the subject is greater than the second threshold, the first threshold is 24.0, and the second threshold is 2.751 [$cm^3$].

10. A stratification method comprising:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, wherein each of the plurality of subjects has a positive beta-amyloid brain PET scan, the hippocampus volume of each of the plurality of subjects is a left hippocampus volume of each of the plurality of subjects, the clinical psychological test is an Alzheimer's disease assessment scale-cognitive subscale test, and in the classifying, for each of the plurality of subjects, a volume score value indicating a ratio between the left hippocampus volume of the subject and the score of the subject is calculated, and each of the plurality of subjects is classified into one of the plurality of groups based on the calculated volume score value.

11. The stratification method according to claim 10, wherein the volume score value is a ratio of the left hippocampus volume [$mm^3$] to the score, and in the classifying, for each of the plurality of subjects, the subject is classified into the first group if the volume score value of the subject is less than 101.

12. A stratification method comprising:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, wherein the hippocampus volume of each of the plurality of subjects is a left hippocampus volume of each of the plurality of subjects, the clinical psychological test is an Alzheimer's disease assessment scale-cognitive subscale test, and in the classifying, for each of the plurality of subjects, a volume score value indicating a ratio between the left hippocampus volume of the subject and the score of the subject is calculated, and each of the plurality of subjects is classified into one of the plurality of groups based on the calculated volume score value.

13. The stratification method according to claim 12, wherein the volume score value is a ratio of the left hippocampus volume [$mm^3$] to the score, and in the classifying, for each of the plurality of subjects, the subject is classified into the first group if the volume score value of the subject is less than 101.

14. A stratification device comprising:

a processor; and memory storing a program, wherein when executed by the processor, the program causes the processor to perform:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, the hippocampus volume of each of the plurality of subjects is a right hippocampus volume of each of the plurality of subjects, the clinical psychological test is an Alzheimer's disease assessment scale-cognitive subscale test, the classifying includes, for each of the plurality of subjects, classifying the subject into the first group if the score of the subject is greater than a first threshold and the right hippocampus volume of the subject is less than a second threshold, and classifying the subject into the second group if the score of the subject is less than the first threshold and the right hippocampus volume of the subject is greater than the second threshold, the first threshold is 20.0±1 SD, the second threshold is 3.651±1 SD [$cm^3$], the 1 SD of the first threshold is 6.3, and the 1 SD of the second threshold is 0.653 [$cm^3$].

15. The stratification device according to claim 14, wherein the obtaining includes obtaining, for each of the plurality of subjects, information indicating whether the subject is an apolipoprotein Eε4 gene carrier, and in the classifying, each of the plurality of subjects is classified into one of the plurality of groups further based on the information.

16. A stratification device comprising:

a processor; and memory storing a program, wherein when executed by the processor, the program causes the processor to perform:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, the clinical psychological test is a preclinical Alzheimer's cognitive composite test, the classifying included, for each of the plurality of subjects, classifying the subject into the first group if the score of the subject is less than a first threshold and a right hippocampus volume of the subject is less than a second threshold, and classifying the subject into the second group if the score of the subject is greater than the first threshold and the right hippocampus volume of the subject is greater than the second threshold, the first threshold is 0.111±1 SD, the second threshold is 3.651±1 SD [$cm^3$], the 1 SD of the first threshold is 2.630, and the 1 SD of the second threshold is 0.653 [$cm^3$].

17. The stratification device according to claim 16, wherein the obtaining includes obtaining, for each of the plurality of subjects, information indicating whether the subject is an apolipoprotein Eε4 gene carrier, and in the classifying, each of the plurality of subjects is classified into one of the plurality of groups further based on the information.

18. A stratification device comprising:

a processor; and memory storing a program, wherein when executed by the processor, the program causes the processor to perform:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, the hippocampus volume of each of the plurality of subjects is a right hippocampus volume of each of the plurality of subjects, the clinical psychological test includes an Alzheimer's disease assessment scale-cognitive subscale test and a preclinical Alzheimer's cognitive composite test, the obtaining includes obtaining, for each of the plurality of subjects, information indicating whether the subject is an apolipoprotein Eε4 gene carrier, and the classifying includes, for each of the plurality of subjects, classifying the subject into the first group in any of the following cases:

(1) if a first score obtained as a result of the Alzheimer's disease assessment scale-cognitive subscale test performed on the subject is less than a first threshold, the right hippocampus volume of the subject is greater than a second threshold, the information indicates the subject is an apolipoprotein Eε4 gene carrier, and a second score obtained as a result of the preclinical Alzheimer's cognitive composite test performed on the subject is less than a third threshold, the first score being the score;

(2) if the first score of the subject is greater than the first threshold, the right hippocampus volume of the subject is greater than the second threshold, the information indicates the subject is an apolipoprotein Eε4 gene carrier, and the second score of the subject is less than the third threshold;

(3) if the first score of the subject is greater than the first threshold and the right hippocampus volume of the subject is less than the second threshold; or (4) if the first score of the subject is less than the first threshold, the right hippocampus volume of the subject is less than the second threshold, the information indicates the subject is an apolipoprotein Eε4 gene carrier, and the second score of the subject is less than the third threshold, and classifying the subject into the second group in any of the following cases:

(5) if the first score of the subject is less than the first threshold, the right hippocampus volume of the subject is greater than the second threshold, the information indicates the subject is an apolipoprotein Eε4 gene carrier, and the second score of the subject is greater than the third threshold;

(6) if the first score of the subject is greater than the first threshold, the right hippocampus volume of the subject is greater than the second threshold, the information indicates the subject is an apolipoprotein Eε4 gene carrier, and the second score of the subject is greater than the third threshold; or (7) if the first score of the subject is less than the first threshold, the right hippocampus volume of the subject is greater than the second threshold, and the information indicates the subject is not an apolipoprotein Eε4 gene carrier, the first threshold is 20.0±1 SD, the second threshold is 3.651±1 SD [$cm^3$], the third threshold is 0.111±1 SD, the 1 SD of the first threshold is 6.3, and the 1 SD of the second threshold is 0.653 [$cm^3$], and the 1 SD of the third threshold is 2.630.

19. A stratification device comprising:

a processor; and memory storing a program, wherein when executed by the processor, the program causes the processor to perform:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, each of the plurality of subjects has a positive beta-amyloid brain PET scan, the hippocampus volume of each of the plurality of subjects is a left hippocampus volume of each of the plurality of subjects, the clinical psychological test is an Alzheimer's disease assessment scale-cognitive subscale test, the classifying includes, for each of the plurality of subjects, classifying the subject into the first group if the score of the subject is greater than a first threshold and the left hippocampus volume of the subject is less than a second threshold, and classifying the subject into the second group if the score of the subject is less than the first threshold and the left hippocampus volume of the subject is greater than the second threshold, the first threshold is 14.0±1 SD, the second threshold is 3.459±1 SD [$cm^3$], the 1 SD of the first threshold is 6.9, and the 1 SD of the second threshold is 0.5435 [$cm^3$].

20. A stratification device comprising:

a processor; and memory storing a program, wherein when executed by the processor, the program causes the processor to perform:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, each of the plurality of subjects has a positive beta-amyloid brain PET scan, the hippocampus volume of each of the plurality of subjects is a left hippocampus volume of each of the plurality of subjects, the clinical psychological test is an Alzheimer's disease assessment scale-cognitive subscale test, the classifying includes, for each of the plurality of subjects, classifying the subject into the first group if the score of the subject is greater than a first threshold and the left hippocampus volume of the subject is less than a second threshold, and classifying the subject into the second group if the score of the subject is less than the first threshold and the left hippocampus volume of the subject is greater than the second threshold, the first threshold is 12.0, and the second threshold is 3.737 [$cm^3$].

21. A stratification device comprising:

a processor; and memory storing a program, wherein when executed by the processor, the program causes the processor to perform:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, each of the plurality of subjects has a positive beta-amyloid brain PET scan, the hippocampus volume of each of the plurality of subjects is a left hippocampus volume of each of the plurality of subjects, the clinical psychological test is an Alzheimer's disease assessment scale-cognitive subscale test, the classifying includes, for each of the plurality of subjects, classifying the subject into the first group if the score of the subject is greater than a first threshold and the left hippocampus volume of the subject is less than a second threshold, and classifying the subject into the second group if the score of the subject is less than the first threshold and the left hippocampus volume of the subject is greater than the second threshold, the first threshold is 21.0, and the second threshold is 3.080 [$cm^3$].

22. A stratification device comprising:

a processor; and memory storing a program, wherein when executed by the processor, the program causes the processor to perform:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, each of the plurality of subjects has a positive beta-amyloid brain PET scan, the hippocampus volume of each of the plurality of subjects is a left hippocampus volume of each of the plurality of subjects, the clinical psychological test is an Alzheimer's disease assessment scale-cognitive subscale test, the classifying includes, for each of the plurality of subjects, classifying the subject into the first group if the score of the subject is greater than a first threshold and the left hippocampus volume of the subject is less than a second threshold, and classifying the subject into the second group if the score of the subject is less than the first threshold and the left hippocampus volume of the subject is greater than the second threshold, the first threshold is 24.0, and the second threshold is 2.751 [$cm^3$].

23. A stratification device comprising:

a processor; and memory storing a program, wherein when executed by the processor, the program causes the processor to perform:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, each of the plurality of subjects has a positive beta-amyloid brain PET scan, the hippocampus volume of each of the plurality of subjects is a left hippocampus volume of each of the plurality of subjects, the clinical psychological test is an Alzheimer's disease assessment scale-cognitive subscale test, and the classifying includes, for each of the plurality of subjects, calculating a volume score value indicating a ratio between the left hippocampus volume of the subject and the score of the subject, and classifying each of the plurality of subjects into one of the plurality of groups based on the calculated volume score value.

24. The stratification device according to claim 23, wherein the volume score value is a ratio of the left hippocampus volume [$mm^3$] to the score, and in the classifying, for each of the plurality of subjects, the subject is classified into the first group if the volume score value of the subject is less than 101.

25. A stratification device comprising:

a processor; and memory storing a program, wherein when executed by the processor, the program causes the processor to perform:

obtaining, for each of a plurality of subjects with mild cognitive impairment, a score of a result of a clinical psychological test performed on the subject and a hippocampus volume of the subject, the hippocampus volume of the subject being obtained by performing a Magnetic Resonance Imaging (MRI) test on the subject to obtain to an MRI image of the subject, and measuring the hippocampus volume of the subject using the MRI image of the subject;

classifying each of the plurality of subjects into one of a plurality of groups based on the score of the subject and the hippocampus volume of the subject, the plurality of groups including at least a first group at a relatively high risk of future progression to Alzheimer's disease and a second group at a relatively low risk of future progression to Alzheimer's disease; and outputting a classification result of the classifying, the hippocampus volume of each of the plurality of subjects is a left hippocampus volume of each of the plurality of subjects, the clinical psychological test is an Alzheimer's disease assessment scale-cognitive subscale test, and the classifying includes, for each of the plurality of subjects, calculating a volume score value indicating a ratio between the left hippocampus volume of the subject and the score of the subject, and classifying each of the plurality of subjects into one of the plurality of groups based on the calculated volume score value.

26. The stratification device according to claim 25, wherein the volume score value is a ratio of the left hippocampus volume [$mm^3$] to the score, and in the classifying, for each of the plurality of subjects, the subject is classified into the first group if the volume score value of the subject is less than 101.

* * * * *